United States Patent
Strano et al.

(10) Patent No.: US 11,474,102 B2
(45) Date of Patent: Oct. 18, 2022

(54) PROTEIN CORONA PHASE MOLECULAR RECOGNITION

(71) Applicant: Massachusetts Institute of Technology, Cambridge, MA (US)

(72) Inventors: Michael S. Strano, Lexington, MA (US); Gili H. Bisker Raviv, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 307 days.

(21) Appl. No.: 15/778,222

(22) PCT Filed: Nov. 22, 2016

(86) PCT No.: PCT/US2016/063430
§ 371 (c)(1),
(2) Date: May 22, 2018

(87) PCT Pub. No.: WO2017/091631
PCT Pub. Date: Jun. 1, 2017

(65) Prior Publication Data
US 2018/0356414 A1   Dec. 13, 2018

Related U.S. Application Data

(60) Provisional application No. 62/259,046, filed on Nov. 23, 2015.

(51) Int. Cl.
*G01N 33/543* (2006.01)
*B82Y 15/00* (2011.01)
(Continued)

(52) U.S. Cl.
CPC ........ *G01N 33/54346* (2013.01); *B82Y 15/00* (2013.01); *G01N 33/531* (2013.01);
(Continued)

(58) Field of Classification Search
None
See application file for complete search history.

(56) References Cited

U.S. PATENT DOCUMENTS 6,087,462 A * 7/2000 Bowers ................. C08F 246/00
526/277
6,120,751 A * 9/2000 Unger ................ A61K 41/0028
264/4
(Continued)

FOREIGN PATENT DOCUMENTS

WO    2015/191389    12/2015

OTHER PUBLICATIONS

Webb et al, Biochim. Biophys. Acta, vol. 1372, pp. 272-282, published 1998.*
(Continued)

*Primary Examiner* — Robert T. Crow
(74) *Attorney, Agent, or Firm* — Honigman, LLP

(57) ABSTRACT

Corona Phase Molecular Recognition (CoPhMoRe) utilizing a heteropolymer adsorbed onto and templated by a nanoparticle surface to recognize a specific target analyte can be used for macromolecular analytes, including proteins. A variant of a CoPhMoRe screening procedure of single walled carbon nanotubes (SWCNT) can be used against a panel of human blood proteins, revealing a specific corona phase that recognizes fibrinogen and insulin, respectively, with high selectivity.

18 Claims, 65 Drawing Sheets

Specification includes a Sequence Listing.

(51) Int. Cl.
   *G01N 33/53* (2006.01)
   *G01N 33/531* (2006.01)
   *G01N 33/74* (2006.01)

(52) U.S. Cl.
   CPC ......... *G01N 33/5308* (2013.01); *G01N 33/74* (2013.01); *G01N 2333/62* (2013.01)

(56) References Cited

U.S. PATENT DOCUMENTS

| | | | | |
|---|---|---|---|---|
| 8,460,608 | B2* | 6/2013 | Strano | .................... B82Y 30/00 422/82.07 |
| 8,486,709 | B2* | 7/2013 | Strano | .............. G01N 33/54373 436/116 |
| 8,670,808 | B2 | 3/2014 | Glezer et al. | |
| 8,765,488 | B2* | 7/2014 | Strano | .................... G01N 33/66 436/529 |
| 8,778,269 | B2 | 7/2014 | Joshi et al. | |
| 9,664,677 | B2 | 5/2017 | Strano et al. | |
| 9,901,295 | B2* | 2/2018 | Iverson | ................. B82Y 15/00 |
| 9,980,668 | B2* | 5/2018 | Strano | .................. G01N 33/542 |
| 2007/0065359 | A1* | 3/2007 | Sengupta | ........... A61K 51/1244 424/1.11 |
| 2009/0166560 | A1* | 7/2009 | Dai | ...................... C01B 32/156 250/492.1 |
| 2011/0105335 | A1 | 5/2011 | Glezer et al. | |
| 2011/0257033 | A1 | 10/2011 | Strano et al. | |
| 2012/0018301 | A1 | 1/2012 | Joshi et al. | |

OTHER PUBLICATIONS

"Poly(ethylene glycol) and Poly(ethylene oxide)," sigmaaldrich.com [retrieved on Aug. 5, 2020], Retrieved from the Internet:<URL: www.sigmaaldrich.com/materials-science/material-science-products.html?TablePage=20204110>.*

Pubchem.ncbi.nlm.nih.gov [retrieved on Jan. 4, 2020]. Retrieved from the Internet: <URL: pubchem.ncbi.nlm.nih.gov/compound/1_2-Distearoyl-sn-glycero-3-phosphoethanolamine>.*

Jain et al, Biotechnol. J. vol. 10, pp. 447-459, published Feb. 13, 2015.*

Cha et al, ACS Nano, vol. 5, pp. 4236-4244, published online Apr. 26, 2011.*

Notification Concerning Transmittal of International Preliminary Report on Patentability dated Jun. 7, 2018 for PCT/US2016/063430.

International Search Report and Written Opinion dated Mar. 31, 2017 for PCT/US2016/063430.

* cited by examiner

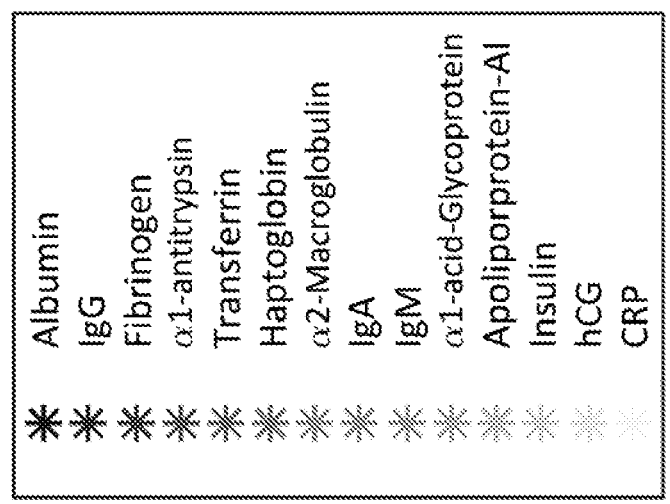
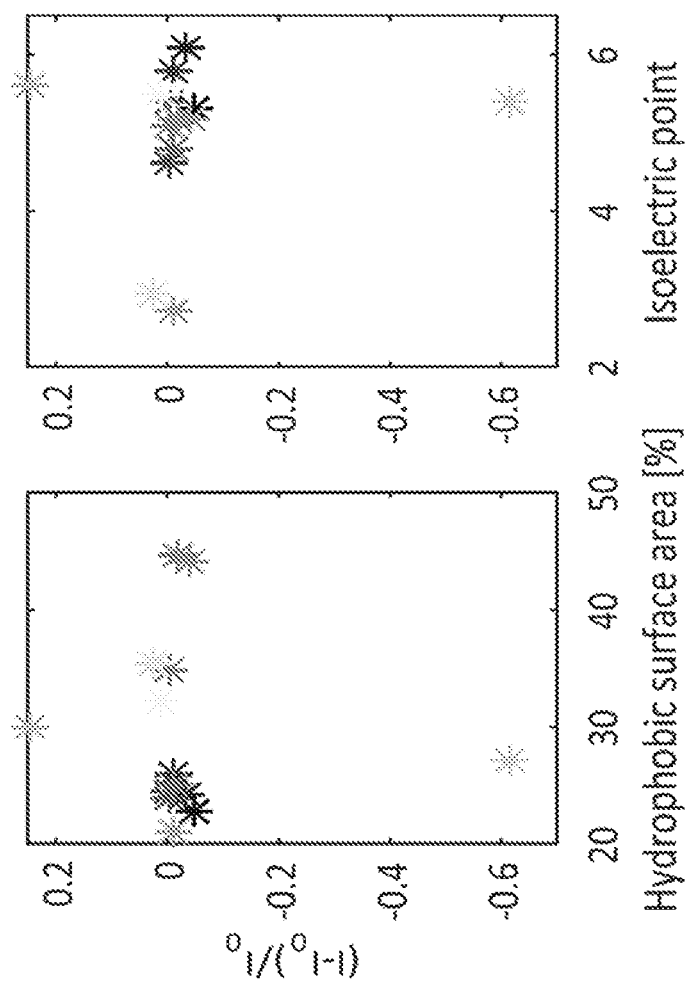
FIG. 19D
FIG. 19E

SEQUENCE LISTING

```
<160> NUMBER OF SEQ ID NOS: 24

<210> SEQ ID NO 1
<211> LENGTH: 30
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 1
gtgtgtgtgt gtgtgtgtgt gtgtgtgtgt                                   30

<210> SEQ ID NO 2
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
gugugugugu gugugugugu gugugugugu                                   30

<210> SEQ ID NO 3
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3 atatatat atatatat atatatat atatatat atatatat atatatat              60

<210> SEQ ID NO 4
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gcgcgcgcgc gcgcgcgcgc gcgcgcgcgc gcgcgcgcgc gcgcgcgcgc gcgcgcgcgc   60

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5 atatatat atatatat atatatat                                         30

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
aaataaataa ataaataaat aaataaat                                     28

<210> SEQ ID NO 7
<211> LENGTH: 28
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 7
atttatttat ttatttattt atttattt                                          28

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gggtgggtgg gtgggtgggt gggtgggt                                          28

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gtttgtttgt ttgtttgttt gtttgttt                                          28

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Cys Val Glu Glu Ala Ser
1               5

<210> SEQ ID NO 11
<211> LENGTH: 7
<212> TYPE: PRT
<213> ORGANISM: Homo sapiens

<400> SEQUENCE: 11

Gly Ile Val Glu Gln Cys Cys
1               5

<210> SEQ ID NO 12
<211> LENGTH: 7
<212> TYPE: PRT
<213> ORGANISM: Homo sapiens

<400> SEQUENCE: 12

Thr Ser Ile Cys Ser Leu Tyr
1               5

<210> SEQ ID NO 13
<211> LENGTH: 7
<212> TYPE: PRT
<213> ORGANISM: Homo sapiens

<400> SEQUENCE: 13

Gln Leu Glu Asn Tyr Cys Asn
```

```
1               5

<210> SEQ ID NO 14
<211> LENGTH: 7
<212> TYPE: PRT
<213> ORGANISM: Homo sapiens

<400> SEQUENCE: 14

Phe Val Asn Gln His Leu Cys
1               5

<210> SEQ ID NO 15
<211> LENGTH: 7
<212> TYPE: PRT
<213> ORGANISM: Homo sapiens

<400> SEQUENCE: 15

Gly Ser His Leu Val Glu Ala
1               5

<210> SEQ ID NO 16
<211> LENGTH: 7
<212> TYPE: PRT
<213> ORGANISM: Homo sapiens

<400> SEQUENCE: 16

Leu Tyr Leu Val Cys Gly Glu
1               5

<210> SEQ ID NO 17
<211> LENGTH: 7
<212> TYPE: PRT
<213> ORGANISM: Homo sapiens

<400> SEQUENCE: 17

Arg Gly Phe Phe Tyr Thr Pro
1               5

<210> SEQ ID NO 18
<211> LENGTH: 7
<212> TYPE: PRT
<213> ORGANISM: Homo sapiens

<400> SEQUENCE: 18

Phe Phe Tyr Thr Pro Lys Thr
1               5

<210> SEQ ID NO 19
<211> LENGTH: 7
<212> TYPE: PRT
<213> ORGANISM: Homo sapiens

<400> SEQUENCE: 19

Leu Val Glu Ala Leu Tyr Leu
1               5

<210> SEQ ID NO 20
<211> LENGTH: 6
<212> TYPE: PRT
<213> ORGANISM: Homo sapiens

<400> SEQUENCE: 20

Arg Gly Phe Phe Tyr Thr
1               5
```

```
<210> SEQ ID NO 21
<211> LENGTH: 13
<212> TYPE: PRT
<213> ORGANISM: Homo sapiens

<400> SEQUENCE: 21

Gly Ile Val Glu Gln Cys Cys Thr Ser Ile Cys Ser Leu
1               5                   10

<210> SEQ ID NO 22
<211> LENGTH: 15
<212> TYPE: PRT
<213> ORGANISM: Homo sapiens

<400> SEQUENCE: 22

Ser His Leu Val Glu Ala Leu Tyr Leu Val Cys Gly Glu Arg Gly
1               5                   10                  15

<210> SEQ ID NO 23
<211> LENGTH: 21
<212> TYPE: PRT
<213> ORGANISM: Homo sapiens

<400> SEQUENCE: 23

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 24
<211> LENGTH: 30
<212> TYPE: PRT
<213> ORGANISM: Homo sapiens

<400> SEQUENCE: 24

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30
```

PROTEIN CORONA PHASE MOLECULAR RECOGNITION

This application claims the benefit under 35 USC 371 to International Application No. PCT/US2016/0063430, filed Nov. 22, 2016, which claims the benefit of prior U.S. Provisional Application No. 62/259,046, filed Nov. 23, 2015, each of which is incorporated by reference in its entirety.

SEQUENCE LISTING

The instant application contains a Sequence Listing which has been submitted electronically in ASCII format and is hereby incorporated by reference in its entirety. Said ASCII copy, created on Jul. 30, 2020, is named 14952_0507_SL.txt and is 4,819 bytes in size.

TECHNICAL FIELD

This invention relates to a polymer-nanostructure composition for selective molecular recognition.

BACKGROUND

Molecular recognition and signal transduction are two of the main challenges in sensor design. Molecular recognition can occur when a folded and constrained heteropolymer, orientated in three dimensional space creates a binding pocket or surface that can be identified by a specific counterpart. Nature generally offers few ways to enable molecular recognition, including antibodies and aptamers. Scientists and engineers can borrow from nature to gain analyte specificity and sensitivity, using natural antibodies as vital components of the sensor. However, antibodies can be expensive, fragile, and unstable, easily losing biological activity upon modification, such as immobilization, and exhibit batch-dependent variation. These characteristics can limit their use in widespread applications. Moreover, certain molecules of interest do not have a naturally existing antibody, including toxins, drugs and explosives.

Even with a solution for molecular recognition, measuring the analyte binding event can remain a challenge. For fluorescence-based sensors, a common method has been through Förster resonance energy transfer (FRET) between acceptor and donor fluorophores; however, such sensors usually require labeling. In certain circumstances, fluorescence based sensors can utilize fluorophores that photobleach over time, significantly limiting their capability for long-term continuous monitoring. Consequently, improved systems and methods for molecular recognition and detection are needed.

SUMMARY

A composition can include a complex, wherein the complex includes a nanostructure; and a polymer, the polymer adsorbed on the nanostructure and the polymer being free from selective binding to an analyte in the absence of being adsorbed on the nanostructure, wherein the polymer is a heteropolymer including a hydrophobic region and a hydrophilic region, and a selective binding site associated with the complex.

In one aspect, the nanostructure can be a photoluminescent nanostructure. In certain embodiments, the photoluminescent nanostructure can be a nanotube, a carbon nanotube, or a single-walled carbon nanotube.

In another aspect, the polymer can include a polysaccharide. In certain embodiments, the polysaccharide can include dextran, a functionalized dextran, phenoxy functionalized dextran, or boronic acid functionalized phenoxy dextran.

In another aspect, the polymer can include a polynucleotide. In certain embodiments, the polynucleotide can have an ordered sequence, or can be poly(AT), poly(GU), poly (GT), poly(CT), poly(AG), poly(GC), poly(AC), poly (AAAT), poly(ATTT), poly(GGGT), or poly(GTTT).

In another aspect, the polymer can include a polypeptide. In certain embodiments, the polypeptide can include a mastoparan, mastoparan 7, or mastoparan X.

In another aspect, the polymer can include a polylipid. In certain embodiments, the composition of claim 10, wherein the polylipid can include a phospholipid, a palmitoyl phospholipid, 1,2-dipalmitoyl-sn-glycero-3-phosphoethanolamine-N-(lauroyl), dipalmitoyl-phosphatidyletanolamine, dimyristoyl-phosphatidyletanolamine or distearoyl-phosphatidyletanolamine.

In another aspect, the polymer can include polyvinylpyrrolidone, poly(ethylene oxide)-poly(propylene oxide)-poly (ethyleneo oxide) block co-polymer, a poly(ethylene oxide), poly(N-isopropyl acrylamide), polyethyleneimine, polyacrylamide, polyvinyl alcohol or collagen.

In another aspect, the polymer can include a dye conjugate or a branched polymer.

In another aspect, the polymer can include a phospholipid and a poly(ethylene oxide). In certain embodiments, the phospholipid can be dipalmitoyl-phosphatidyletanolamine, dimyristoyl-phosphatidyletanolamine or distearoyl-phosphatidyletanolamine.

In another aspect, the analyte can be a monosaccharide, a polysaccharide, an amino acid, a nucleotide, an oligonucleotide, a lipid, a polylipid, a steroid, a peptide, a protein, riboflavin, or nitric oxide. In certain embodiments, the analyte can be 17-α-estradiol, 2,4-dinitrophenol, acetylcholine chloride, α-tocopherol, adenosine, adenosine-5'-triphosphate, cyclic adenosine monophosphate, creatinine, cytidine, D-aspartic acid, D-fructose, D-galactose, D-glucose, D-mannose, dopamine, glycine, guanosine, histamine, L-ascorbic acid, L-citrulline, L-histidine, L-thyroxine, melatonin, NADH, quinine, salicylic acid, serotonin, sodium azide, sodium pyruvate, sucrose, thymidine, tryptophan, tyramin or urea. In certain embodiments, the analyte can be fibrinogen. In certain embodiments, the analyte can be insulin.

In another aspect, the heteropolymer can be ceramide-$C_{16}$-PEG(2000 kDa).

In another aspect, the heteropolymer can be dipalmitoyl-phosphatidyletanolamine (DPPE)-PEG(5000).

The composition can further comprise an amount of the analyte.

In certain embodiments, the analyte can be a therapeutic.

A method for analyzing a sample for an analyte can include providing a composition including a complex, wherein the complex includes a nanostructure, and a polymer, the polymer adsorbed on the nanostructure and the polymer being free from selective binding to an analyte in the absence of being adsorbed on the nanostructure wherein the polymer is a heteropolymer including a hydrophobic region and a hydrophilic region; and a selective binding site associated with the complex, exposing the composition to a sample, monitoring a property of the composition, and determining a presence of an analyte in the sample based on the property.

In one aspect, the nanostructure can be a photoluminescent nanostructure. In certain embodiments, the photoluminescent nanostructure can be a nanotube, a carbon nanotube, or a single-walled carbon nanotube.

In another aspect, the polymer can include a polysaccharide. In certain embodiments, the polysaccharide can include dextran, a functionalized dextran, phenoxy functionalized dextran, or boronic acid functionalized phenoxy dextran.

In another aspect, the polymer can include a polynucleotide. In certain embodiments, the polynucleotide can have an ordered sequence, or can be poly(AT), poly(GU), poly(GT), poly(CT), poly(AG), poly(GC), poly(AC), poly(AAAT), poly(ATTT), poly(GGGT), or poly(GTTT).

In another aspect, the polymer can include a polypeptide. In certain embodiments, the polypeptide can include a mastoparan, mastoparan 7, or mastoparan X.

In another aspect, the polymer can include a polylipid. In certain embodiments, the composition of claim 10, wherein the polylipid can include a phospholipid, a palmitoyl phospholipid, 1,2-dipalmitoyl-sn-glycero-3-phosphoethanolamine-N-(lauroyl), dipalmitoyl-phosphatidyletanolamine, dimyristoyl-phosphatidyletanolamine or distearoyl-phosphatidyletanolamine.

In another aspect, the polymer can include polyvinylpyrrolidone, poly(ethylene oxide)-poly(propylene oxide)-poly(ethyleneo oxide) block co-polymer, a poly(ethylene oxide), poly(N-isopropyl acrylamide), polyethyleneimine, polyacrylamide, polyvinyl alcohol or collagen.

In another aspect, the polymer can include a dye conjugate or a branched polymer.

In another aspect, the polymer can include a phospholipid and a poly(ethylene oxide). In certain embodiments, the phospholipid can be dipalmitoyl-phosphatidyletanolamine, dimyristoyl-phosphatidyletanolamine or distearoyl-phosphatidyletanolamine.

In another aspect, the analyte can be a monosaccharide, a polysaccharide, an amino acid, a nucleotide, an oligonucleotide, a lipid, a polylipid, a steroid, a peptide, a protein, riboflavin, or nitric oxide. In certain embodiments, the analyte can be 17-α-estradiol, 2,4-dinitrophenol, acetylcholine chloride, α-tocopherol, adenosine, adenosine-5'-triphosphate, cyclic adenosine monophosphate, creatinine, cytidine, D-aspartic acid, D-fructose, D-galactose, D-glucose, D-mannose, dopamine, glycine, guanosine, histamine, L-ascorbic acid, L-citrulline, L-histidine, L-thyroxine, melatonin, NADH, quinine, salicylic acid, serotonin, sodium azide, sodium pyruvate, sucrose, thymidine, tryptophan, tyramin or urea. In certain embodiments, the analyte can be fibrinogen. In certain embodiments, the analyte can be insulin.

In another aspect, the heteropolymer can be ceramide-$C_{16}$-PEG(2000 kDa).

In another aspect, the heteropolymer can be dipalmitoyl-phosphatidyletanolamine (DPPE)-PEG(5000).

The composition can further comprise an amount of the analyte.

In certain embodiments, the analyte can be a therapeutic.

In certain embodiments, the sample can include a gas, a liquid or a solid. In certain embodiments, the sample can be a biological fluid.

In certain embodiments, the property can be an emission, emission intensity, or an emission wavelength.

In certain embodiments, exposing the composition to a sample can include inserting the composition into an animal, a plant, or a fungus.

In certain embodiments, exposing the composition to a sample can include incubating the composition with a microorganism, a virus, a cell line, or an in vitro model system.

In certain embodiments, determining the presence of an analyte can include determining the absence of the analyte, or determining the concentration of the analyte.

In certain embodiments, monitoring a property of the composition can be performed using a high-throughput system.

In certain embodiments, the composition can be exposed to a sample in a well in a well plate array.

A method for analyzing samples in a high-throughput system can include providing an array including a plurality of compositions, wherein each composition includes a complex, wherein the complex includes a nanostructure, and a polymer, the polymer adsorbed on the nanostructure and the polymer being free from selective binding to an analyte in the absence of being adsorbed on the nanostructure, wherein the polymer is a heteropolymer including a hydrophobic region and a hydrophilic region; and a selective binding site associated with the complex, exposing each composition to at least one sample, monitoring a property of each composition, and determining a presence of an analyte in the sample based on the property.

In certain embodiments, the polymer can include a phospholipid and a poly(ethylene oxide).

In certain embodiments, the phospholipid can be dipalmitoyl-phosphatidyletanolamine, dimyristoyl-phosphatidyletanolamine or distearoyl-phosphatidyletanolamine.

In certain embodiments, the analyte can be fibrinogen. In certain embodiments, the analyte can be insulin.

In another aspect, the heteropolymer can be ceramide-$C_{16}$-PEG(2000 kDa).

In another aspect, the heteropolymer can be dipalmitoyl-phosphatidyletanolamine (DPPE)-PEG(5000).

A system can include a complex, wherein the complex includes a photoluminescent nanostructure; and a polymer, the polymer adsorbed on the nanostructure and the polymer being free from selective binding to an analyte in the absence of being adsorbed on the nanostructure, wherein the polymer is a heteropolymer including a hydrophobic region and a hydrophilic region, and a selective binding site associated with the complex, an electromagnetic radiation source having an excitation wavelength directed at the composition, and a detector configured to receive an emission wavelength from the composition.

In certain embodiments, the photoluminescent nanostructure can be a nanotube, a carbon nanotube, or a single-walled carbon nanotube.

In certain embodiments, the polymer can include a polysaccharide, a polynucleotide, a polypeptide or a polylipid.

In certain embodiment, the polymer can include poly(ethylene oxide), poly(vinyl alcohol), dextran, phenoxy functionalized dextran, boronic acid functionalized phenoxy dextran, poly(AT), poly(GU), poly(GT), poly(CT), poly(AG), poly(GC), poly(AC), poly(AAAT), poly(ATTT), poly(GGGT), or poly(GTTT), a mastoparan, mastoparan 7, mastoparan X, 1,2-dipalmitoyl-sn-glycero-3-phosphoethanolamine-N-(lauroyl), dipalmitoyl-phosphatidyletanolamine, dimyristoyl-phosphatidyletanolamine, distearoyl-phosphatidyletanolamine, or any combinations thereof.

Other aspects, embodiments, and features will be apparent from the following description, the drawings, and the claims.

BRIEF DESCRIPTION OF THE DRAWINGS

FIG. 1A shows the structure of the phospholipid-PEG constructs used in this study to suspend the SWCNT. (i) Dipalmitoyl-phosphatidyletanolamine (DPPE)-PEG(5000), (ii) Dimyristoyl-phosphatidyletanolamine (DMPE)-PEG(5000), (iii) distearoyl-phosphatidyletanolamine (DSPE)-PEG(5000), (iv) DSPE-PEG(2000), (v) DSPE-PEG(2000)-Cyanur, (vi) DSPE-PEG(2000)-carboxylic acid (CA), (vii) DSPE-PEG(2000)-Maleimide, (viii) DSPE-PEG(2000)-[3-(2-Pyridyldithio)-propionyl] (PDP), (ix) DSPE-PEG(2000)-Amine, (x) DSPE-PEG(2000)-Biotin, (xi) DSPE-PEG(350). The number in parentheses is the molecular weight of the PEG chain in Daltons. FIG. 1B shows the solvatochromic shift as a function of the SWCNT diameter to the power of negative 4 ($d^{-4}$, blue dots) and its linear fit (solid red curve), and the fluorescent emission intensity for each wrapping (dashed black curve). FIG. 1C shows the relative surface coverage of the polymer wrappings ranked in descending order. FIGS. 1B and 1C disclose "$(GT)_{15}$" as SEQ ID NO: 1, "$(GU)_{15}$" as SEQ ID NO: 2, "$(AT)_{30}$" as SEQ ID NO: 3, "$(GC)_{30}$" as SEQ ID NO: 4, "$(AT)_{15}$" as SEQ ID NO: 5, "$(AAAT)_7$" as SEQ ID NO: 6, "$(ATTT)_7$" as SEQ ID NO: 7, "$(GGGT)_7$" as SEQ ID NO: 8 and "$(GTTT)_7$" as SEQ ID NO: 9.

FIG. 2A shows heat-map of the normalized response of the joint peak of the (9,4) and (7,6) SWCNT chiralities to the various proteins. The SWCNT and proteins concentrations were 1 mg $L^{-1}$ and 0.2 µg $ml^{-1}$, respectively. FIG. 2B shows the normalized emission intensity response $(I-I_0)/I_0$, where I and $I_0$ are the final and initial fluorescent intensities, respectively, of DPPE-PEG(5000)-SWCNT versus the protein parameters: molecular weight, relative hydrophobic surface area, and isoelectric point. The black arrows point to the fibrinogen data points. FIG. 2C shows the normalized emission intensity response of the various SWCNT suspensions to fibrinogen versus the relative surface coverage. The black arrow points to the DPPE-PEG(5000) data point. Each value represents the average of three replicates. FIG. 2D shows illustration of the possible fibrinogen—SWCNT interaction. The fibrinogen surface is colored according to the hydrophobicity of each amino acid ranging from white (hydrophilic) to red (hydrophobic). FIGS. 2A and 2C disclose "$(GT)_{15}$" as SEQ ID NO: 1, "$(GU)_{15}$" as SEQ ID NO: 2, "$(AT)_{30}$" as SEQ ID NO: 3, "$(GC)_{30}$" as SEQ ID NO: 4, "$(AT)_{15}$" as SEQ ID NO: 5, "$(AAAT)_7$" as SEQ ID NO: 6, "$(ATTT)_7$" as SEQ ID NO: 7, "$(GGGT)_7$" as SEQ ID NO: 8 and "$(GTTT)_7$" as SEQ ID NO: 9.

FIG. 3A shows relative fluorescent response of DPPE-PEG(5000)-SWCNT (1 mg $L^{-1}$) sensor to fibrinogen fragments (20 µg $ml^{-1}$). FIG. 3B shows fluorescent emission spectra of DPPE-PEG(5000)-SWCNT with 0, $10^{-4}$, $2 \times 10^{-4}$, $4 \times 10^{-4}$, $8 \times 10^{-4}$, $1.2 \times 10^{-3}$, $1.6 \times 10^{-3}$, $2 \times 10^{-3}$, $4 \times 10^{-3}$, $8 \times 10^{-3}$, $1.2 \times 10^{-2}$, $1.6 \times 10^{-2}$, $2 \times 10^{-2}$, $4 \times 10^{-2}$, $8 \times 10^{-2}$, and 0.2 mg $ml^{-1}$ fibrinogen show substantial decrease in emission intensity with increasing protein concentration. Inset: absorption spectra of DPPE-PEG(5000)-SWCNT suspension before (solid black curve) and after (dashed red curve) the addition of 0.02 mg $ml^{-1}$ fibrinogen. FIG. 3C shows excitation-emission profile of the DPPE-PEG(5000)-SWCNT solution before the addition of 0.02 mg $ml^{-1}$ fibrinogen. FIG. 3D shows excitation-emission profile of the DPPE-PEG(5000)-SWCNT solution after the addition of 0.02 mg $ml^{-1}$ fibrinogen. FIG. 3E shows the normalized fluorescent response of the various chiralities in the DPPE-PEG(5000)-SWCNT suspension to the addition of different concentrations of fibrinogen (dots). The fit according to the model described in the text is plotted as solid lines. FIG. 3F shows the parameters of the model used for data fitting in FIG. 3D and their 95% confidence intervals. Dashed lines are guides to the eye. Top panel: the proportional parameter β used to fit the normalized fluorescent response model. Bottom panel: the parameters $K_{d1}$, and $(K_{d23})^{1/2}$ used to fit the normalized fluorescent response model (blue squares, and red circles, respectively). FIG. 3G shows wavelength redshift of the (6,5) fluorescent emission peak of the DPPE-PEG(5000)-SWCNT suspension to the addition of different concentrations of fibrinogen (dots). The fit according to the model described in the text is plotted as a solid line. FIG. 3H shows sensor performance in a complex environment: Relative fluorescent response of DPPE-PEG(5000)-SWCNT suspension following a two-step analyte addition. First, either albumin (columns 1-3), fibrinogen (columns 4-6), or an equal mixture of both (columns 7-9) was added to the solution to a final concentration of 20 µg $ml^{-1}$ and incubated for an hour. Then either PBS (columns 1, 4, 7), albumin (columns 2, 5, 8), or fibrinogen (columns 3, 6, 9) was added to a final protein concentration of 40 µg $ml^{-1}$. The fluorescent response was measured after an additional one hour incubation. FIG. 3I shows relative fluorescent response of DPPE-PEG(5000)-SWCNT (5 mg $L^{-1}$) sensor to fibrinogen (0.05, 0.5, and 5 mg $ml^{-1}$) in serum. Error bars represent the standard deviations between three replicate experiments.

FIG. 4A shows fluorescent emission spectra of 1 mg $L^{-1}$ DPPE-PEG(5000)-SWCNT, to which either PBS (top) or 0.02 mg $ml^{-1}$ fibrinogen (bottom) was added 10 seconds after the beginning of the experiment. Since laser excitation was turned off while adding the solutions, the time point of the PBS or fibrinogen addition appears as a horizontal line with zero intensity. FIG. 4B shows the (10,2) chirality fluorescent emission peak over time of 1 mg $L^{-1}$ DPPE-PEG(5000)-SWCNT, to which either PBS (control) or 0.02 mg $ml^{-1}$ fibrinogen was added. Data taken from FIG. 4A. FIG. 4C shows illustration of solution phase experiment. FIG. 4D shows fluorescent emission over time of immobilized DPPE-PEG(5000)-SWCNT in agarose hydrogel, to which either PBS (control) or 0.02 mg $ml^{-1}$ fibrinogen was added. FIG. 4E shows illustration of hydrogel phase experiment. FIG. 4F shows single DPPE-PEG(5000)-SWCNT fluorescence recorded by a 2D nIR camera before the addition of fibrinogen. FIG. 4G shows single DPPE-PEG(5000)-SWCNT fluorescence after the addition of fibrinogen. FIG. 4H shows corresponding intensity time traces of the 4 diffraction limited single SWCNT spots marked in panels FIG. 4F and FIG. 4G. The dotted line represent the time point at which fibrinogen was added. FIG. 4I shows frequency change (dashed blue curve) and layer thickness (solid orange curve) as measured by quartz crystal microbalance with dissipation (QCM-D), and calculated by the Voigt viscoelastic model, respectively, for a fibrinogen layer deposited on top of a DPPE-PEG(5000)-SWCNT layer, and FIG. 4J is for fibrinogen layer deposited directly on top of the gold coated quartz crystal.

FIG. 5A shows AFM image of fibrinogen molecules on MICA surface. Scale bar is 200 nm. FIG. 5B shows height profiles along the lines in the AFM images. FIG. 5C shows AFM of DPPE-PEG(5000)-SWCNT with fibrinogen on a silicon wafer. Scale bar is 200 nm. FIG. 5D shows illustration of the SWCNT (blue lines) and fibrinogen molecules (green dumbbells) in panel FIG. 5C. FIG. 5E shows cryo-TEM image of DPPE-PEG(5000)-

SWCNT with fibrinogen, showing individually suspended SWCNT and no bundling. The dark spheres are catalyst particles. Scale bar is 50 nm.

Figure 6A:
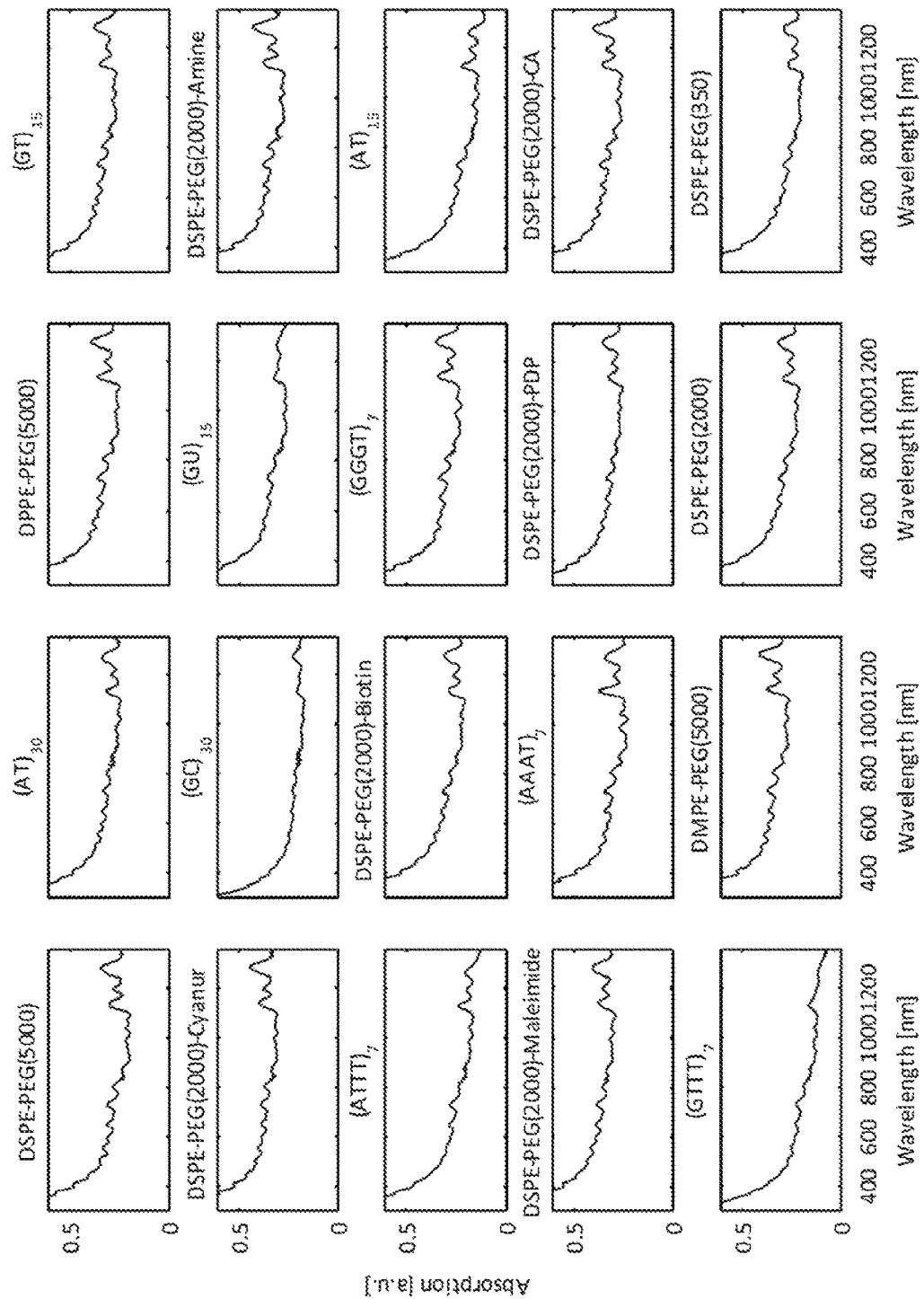
Figure 6B:
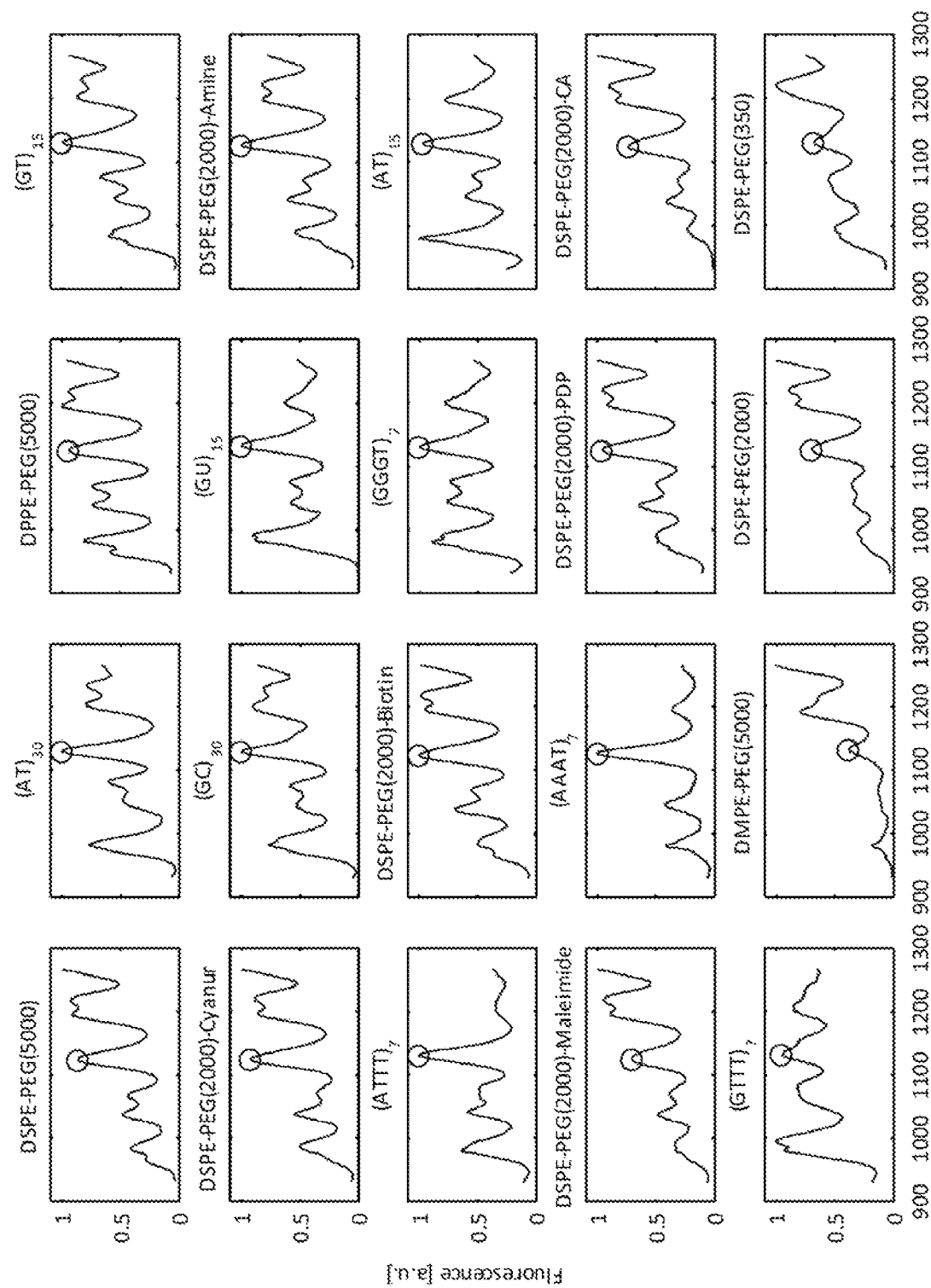

FIGS. 6A-6B show SWCNT library. FIG. 6A shows absorption spectra of the SWCNT suspensions. FIG. 6B shows fluorescent emission spectra of SWCNT suspensions excited by a 785 nm laser. The joint peak of the (9,4) and the (7,6) chiralities is labeled with a circle. FIGS. 6A and 6B disclose "$(GT)_{15}$" as SEQ ID NO: 1, "$(GU)_{15}$" as SEQ ID NO: 2, "$(AT)_{30}$" as SEQ ID NO: 3, "$(GC)_{30}$" as SEQ ID NO: 4, "$(AT)_{15}$" as SEQ ID NO: 5, "$(AAAT)_7$" as SEQ ID NO: 6, "$(ATTT)_7$" as SEQ ID NO: 7, "$(GGGT)_7$" as SEQ ID NO: 8 and "$(GTTT)_7$" as SEQ ID NO: 9.

Figure 7A:
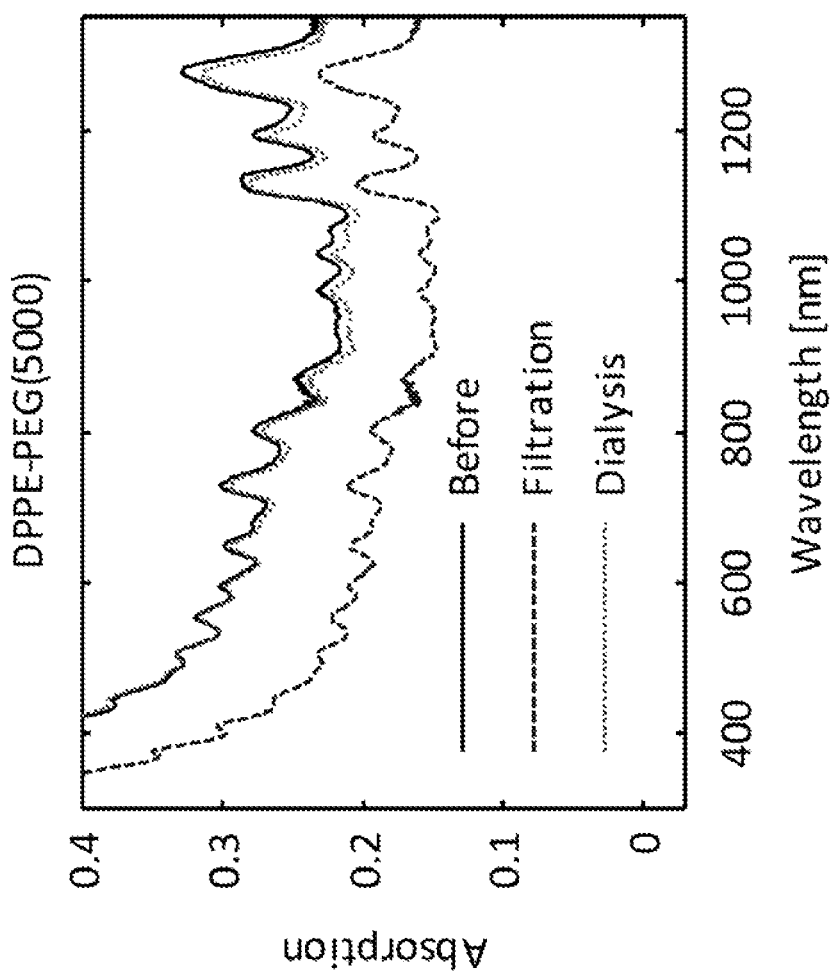
Figure 7B:
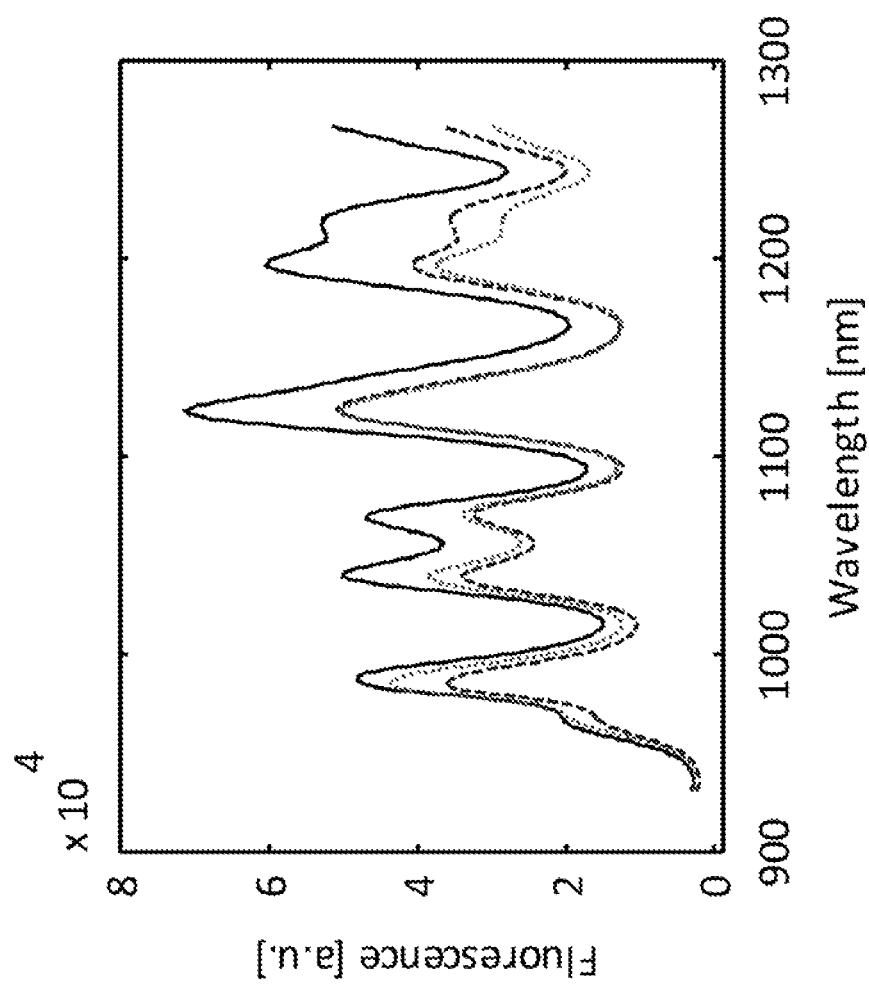
Figure 7C:
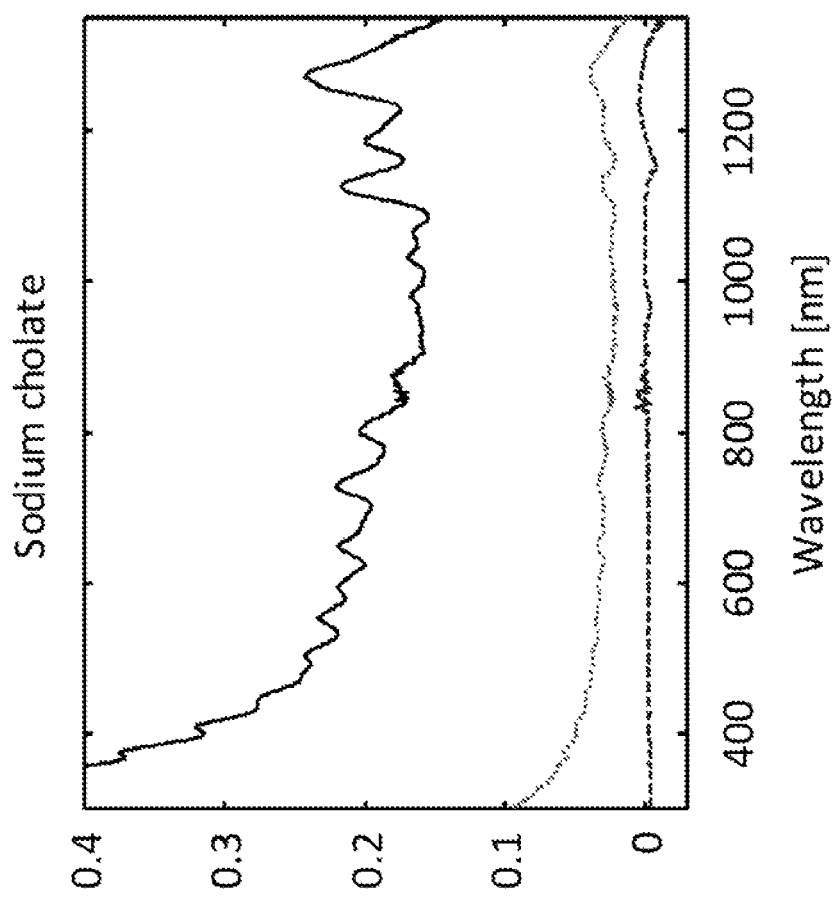
Figure 7D:
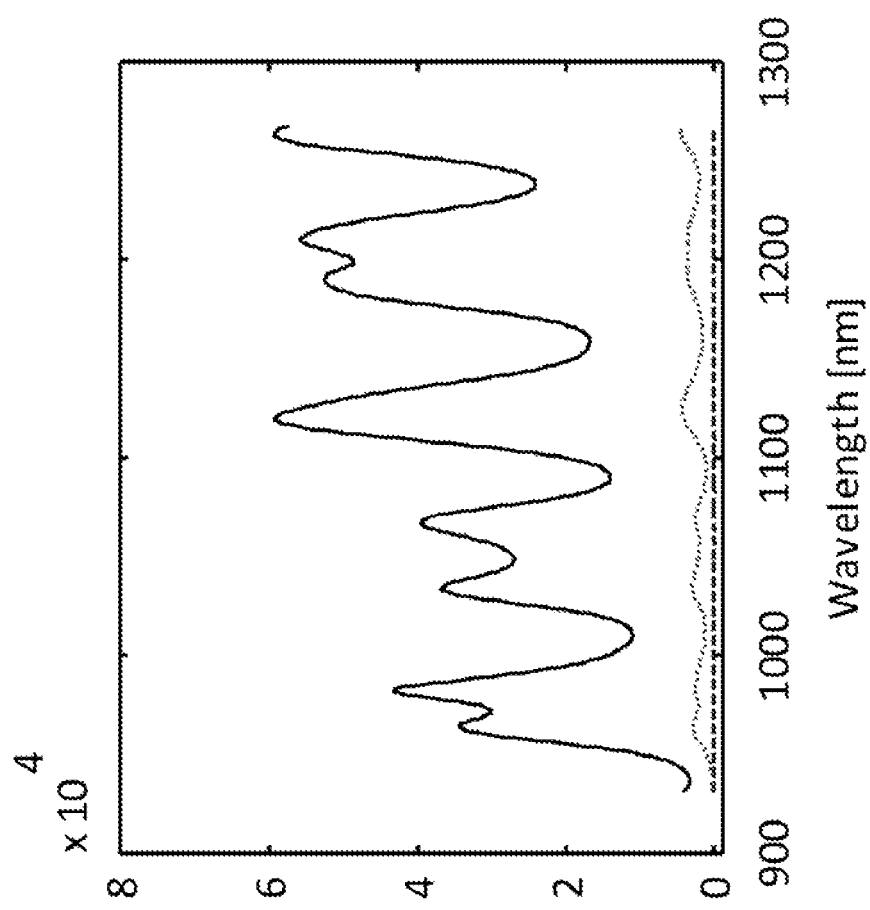

FIGS. 7A-7D show SWCNT suspension stability. FIG. 7A shows absorption spectra and FIG. 7B shows fluorescence spectra of DPPE-PEG(5000)—SWCNT suspensions, before (solid black curves) and after the removal of excess phospholipid-PEG molecules either by filtration through a 100 kDa molecular weight cut off filter (blue dashed line), or by dialysis with 100 kDa molecular weight cut off membrane (dotted green curve). FIG. 7C shows absorption spectra and FIG. 7D shows fluorescence spectra of sodium cholate (SC)—SWCNT suspensions before and after the removal of excess SC molecules in a similar manner.

Figure 8:
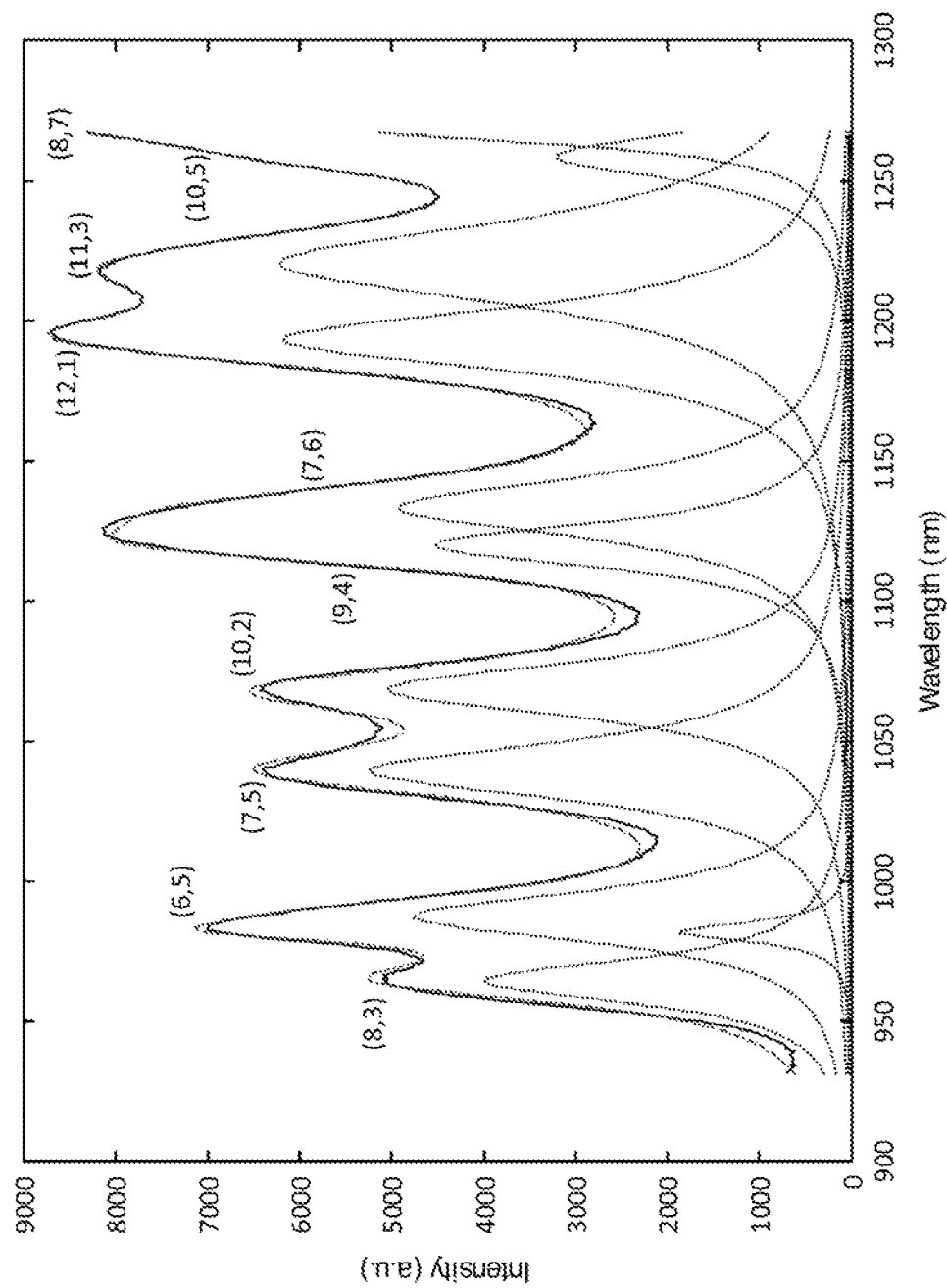

FIG. 8 shows spectra deconvolution. SWCNT fluorescent emission spectrum (solid blue curve) and its deconvolution to the various chiralities (dashed black curves). The fit is illustrated by the dashed red curve.

Figure 9:
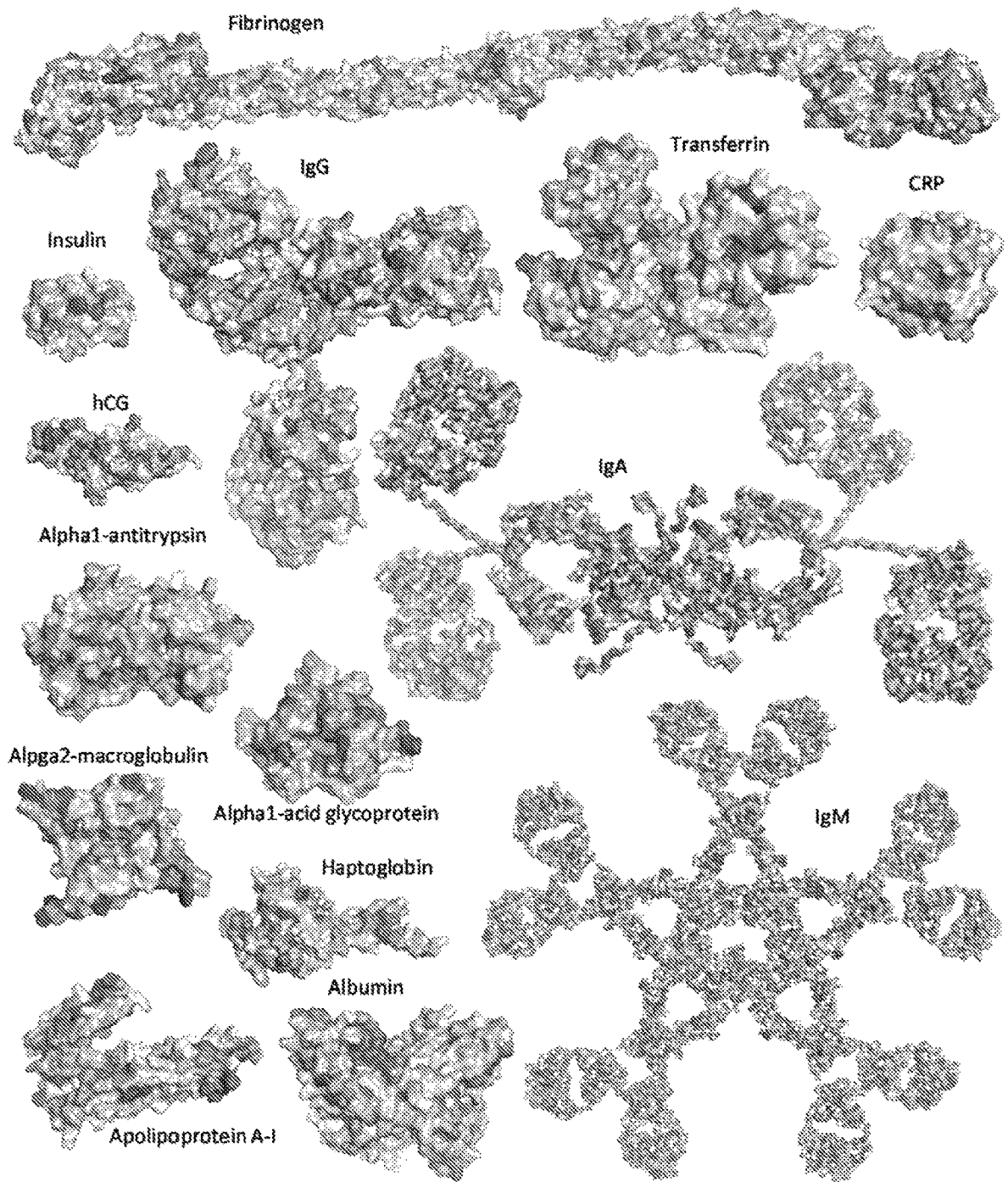

FIG. 9 shows 3D visualization of the proteins panel. The proteins surface is colored according to the hydrophobicity of each amino acid, where the color red is the most hydrophobic, and white is hydrophilic.

Figure 10A:
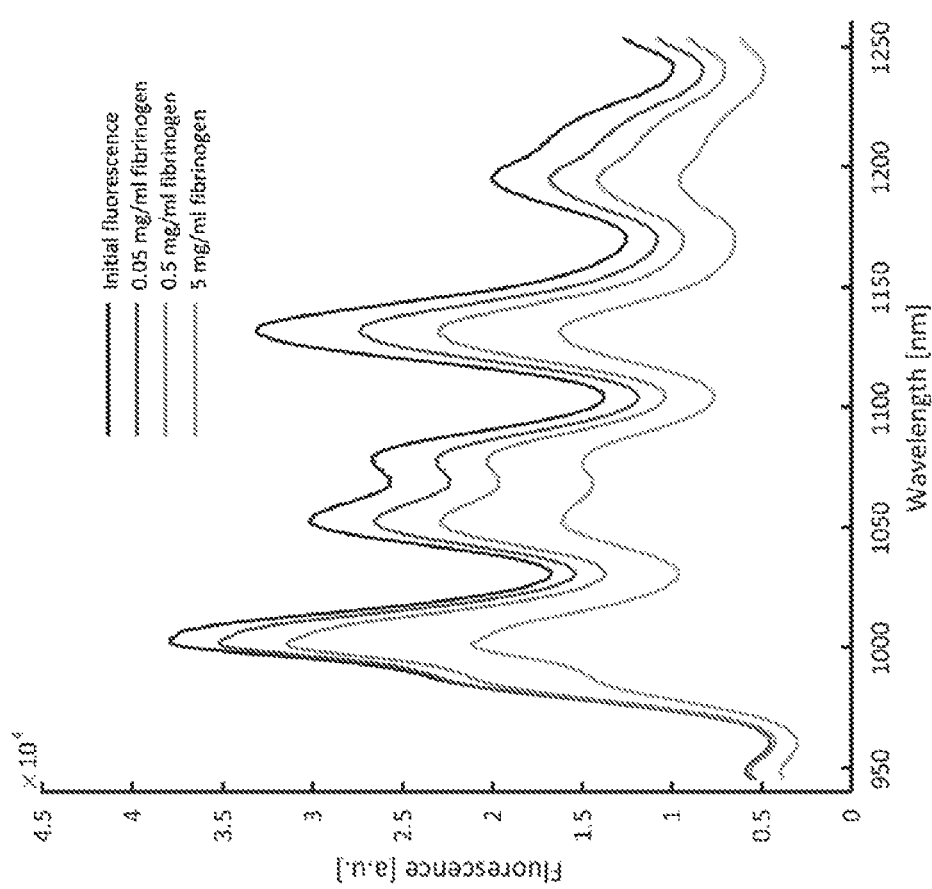
Figure 10B:
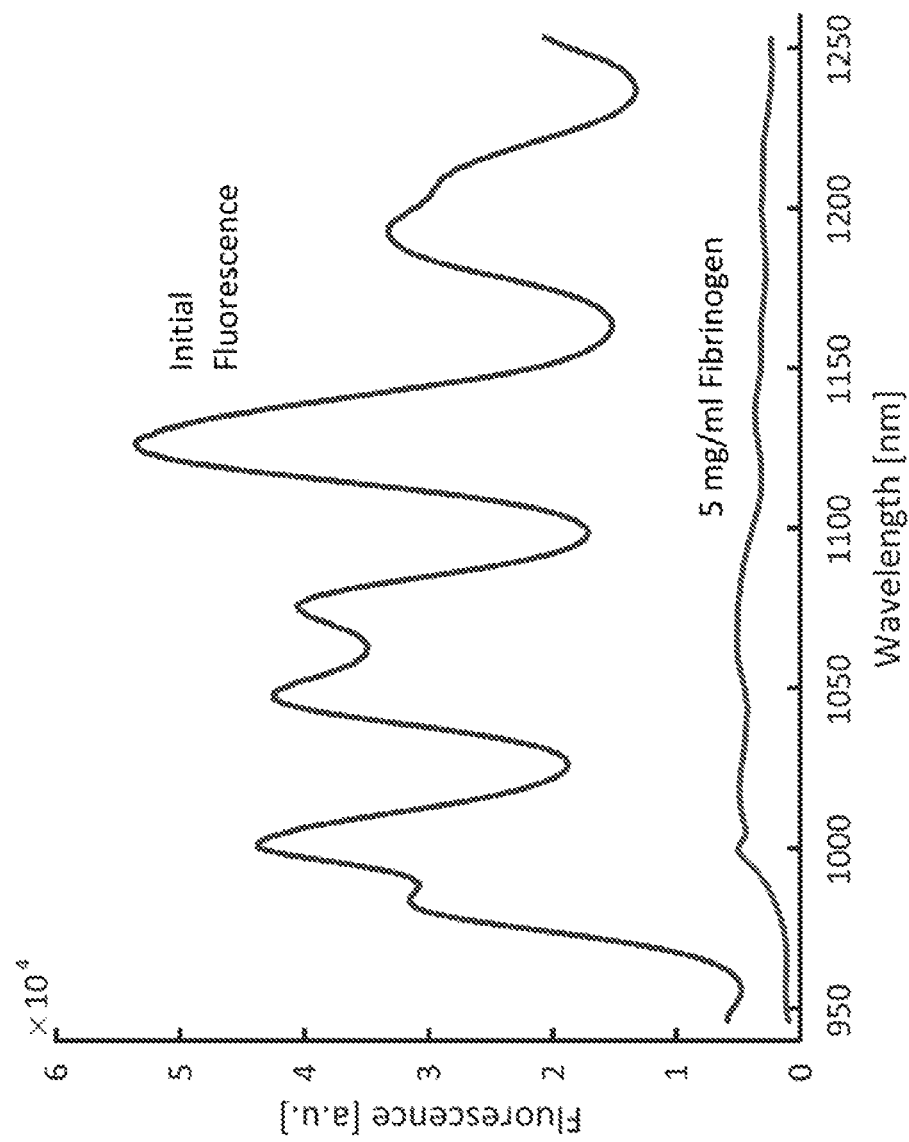

FIGS. 10A-10B show sensor functionality in serum environment. FIG. 10A shows fluorescent response of DPPE-PEG(5000)-SWCNT suspension (5 mg $L^{-1}$) to fibrinogen (0.05, 0.5, and 5 mg $ml^{-1}$) in serum environment (10% fetal Bovine Serum in PBS). FIG. 10B shows fluorescent response of DPPE-PEG(5000)-SWCNT suspension (5 mg $L^{-1}$) to fibrinogen (5 mg $ml^{-1}$) in PBS.

Figure 11:
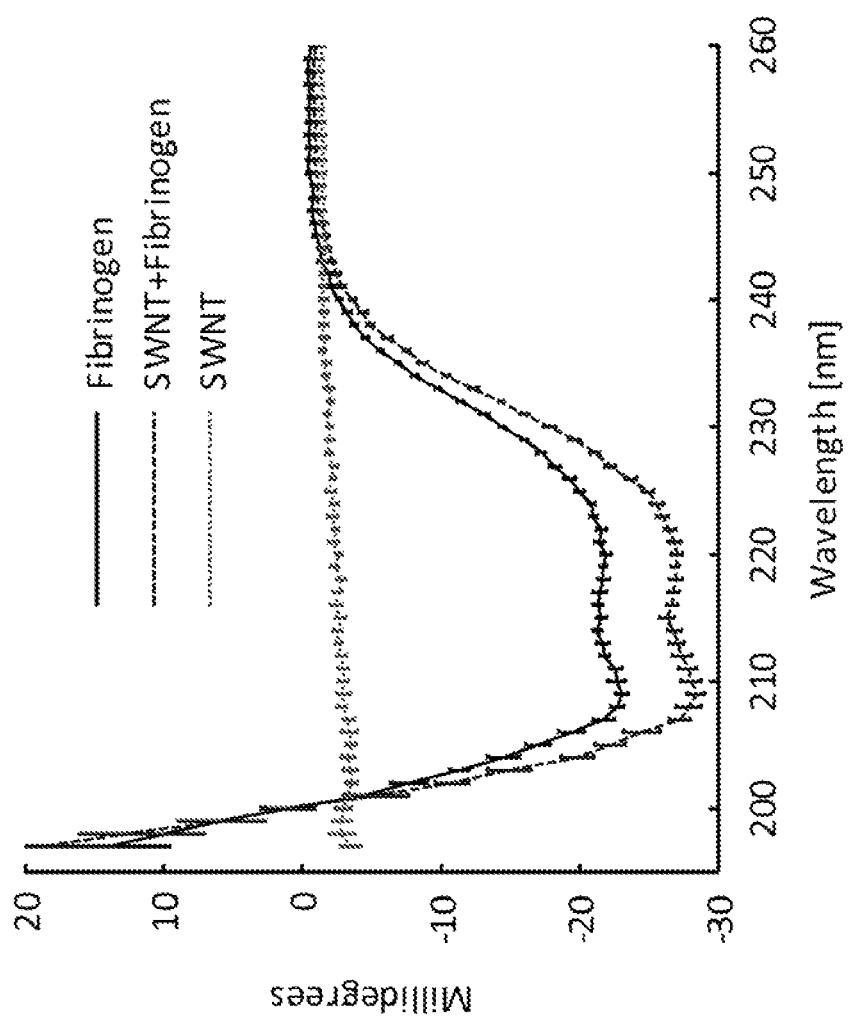

FIG. 11 shows circular dichroism spectroscopy. Circular dichroism spectra of fibrinogen (0.02 mg $ml^{-1}$, black solid curve), DPPE-PEG(5000)-SWCNT (1 mg $L^{-1}$) with 0.02 mg $ml^{-1}$ fibrinogen (blue dashed curve), and DPPE-PEG (5000)-SWCNT (1 mg $L^{-1}$, dotted green curve).

Figure 12A:
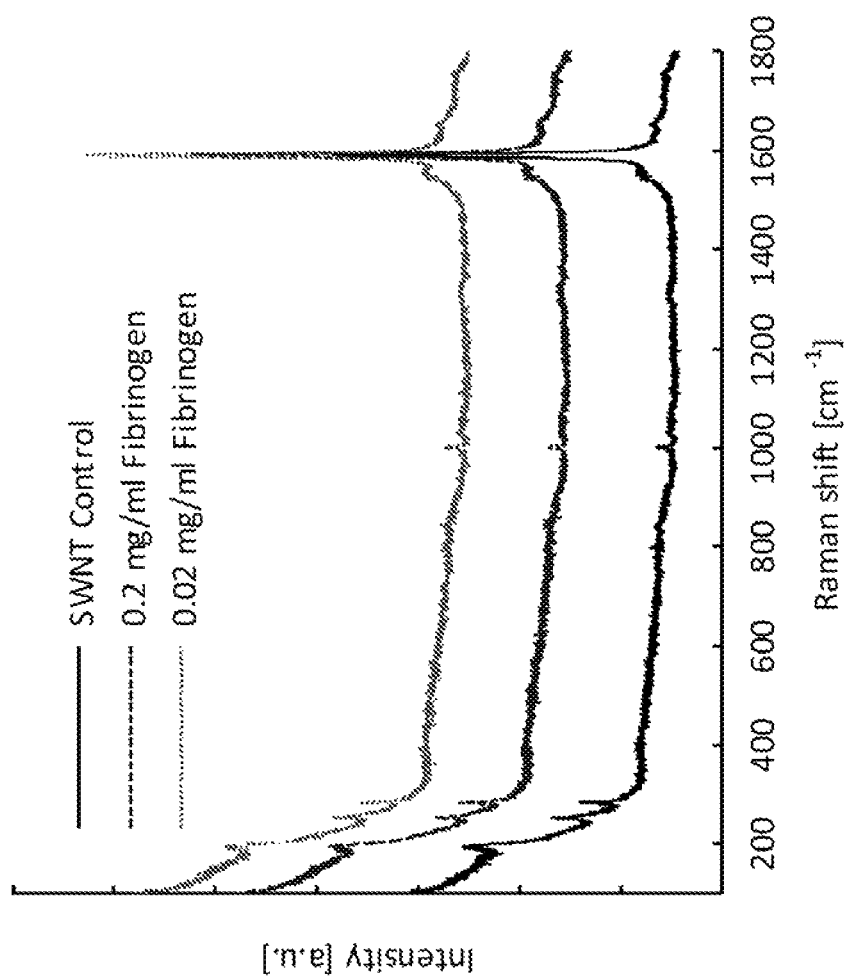
Figures 12B, 12C:
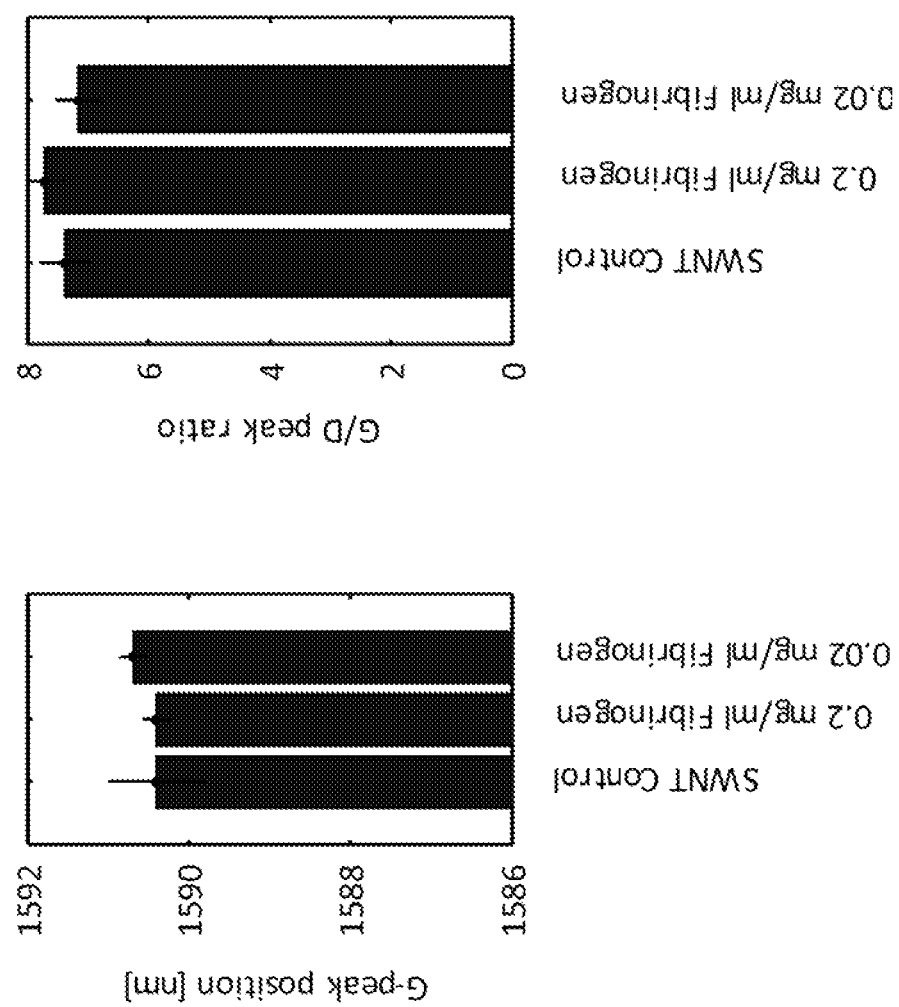
Figure 12D:
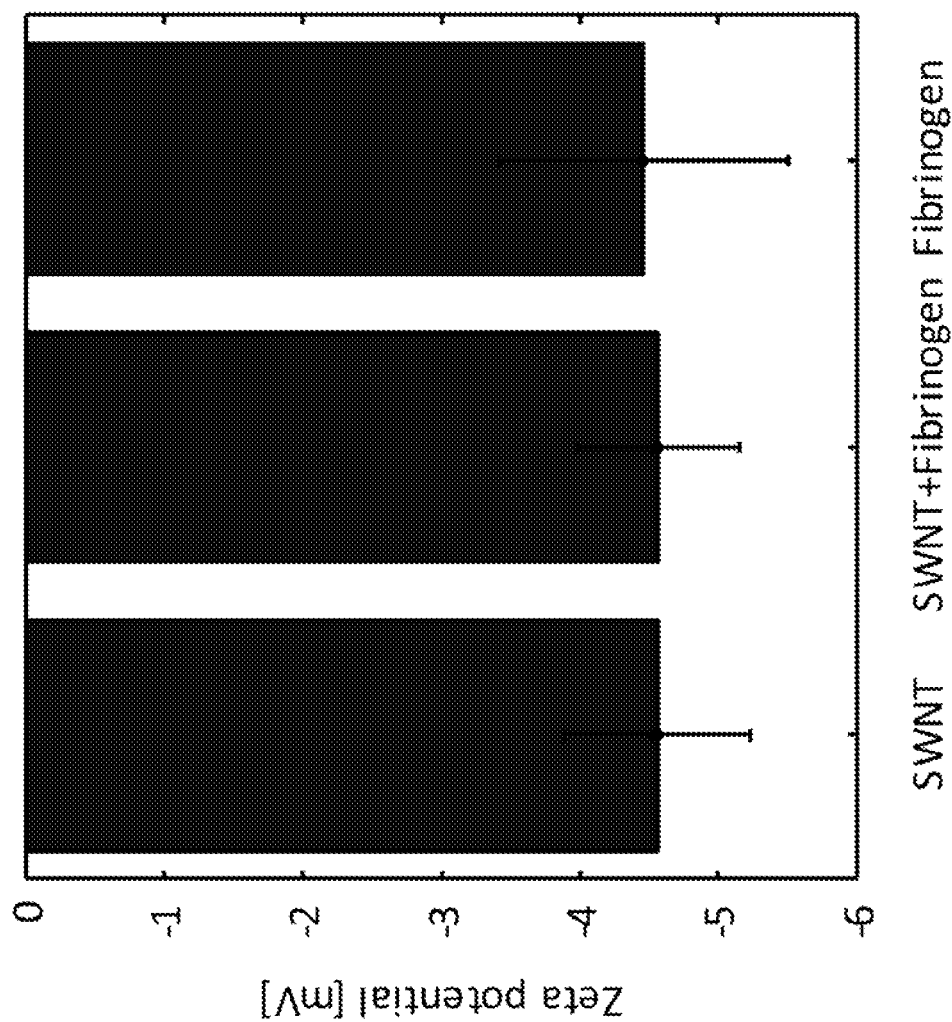

FIGS. 12A-12D show Raman spectroscopy and zeta potential. FIG. 12A shows Raman spectra of DPPE-PEG (5000)-SWCNT (solid black curve), and of DPPE-PEG (5000)-SWCNT with 0.2 mg $ml^{-1}$ (blue dashed curve) or 0.02 mg $ml^{-1}$ (dotted green curve) fibrinogen. FIG. 12B shows G-peak position of each of the spectra in FIG. 12A. FIG. 12C shows G/D peak ratio of each of the spectra in FIG. 12A. FIG. 12D shows zeta potential of DPPE-PEG (5000)-SWCNT, fibrinogen, and DPPE-PEG(5000)-SWCNT with fibrinogen.

Figure 13:
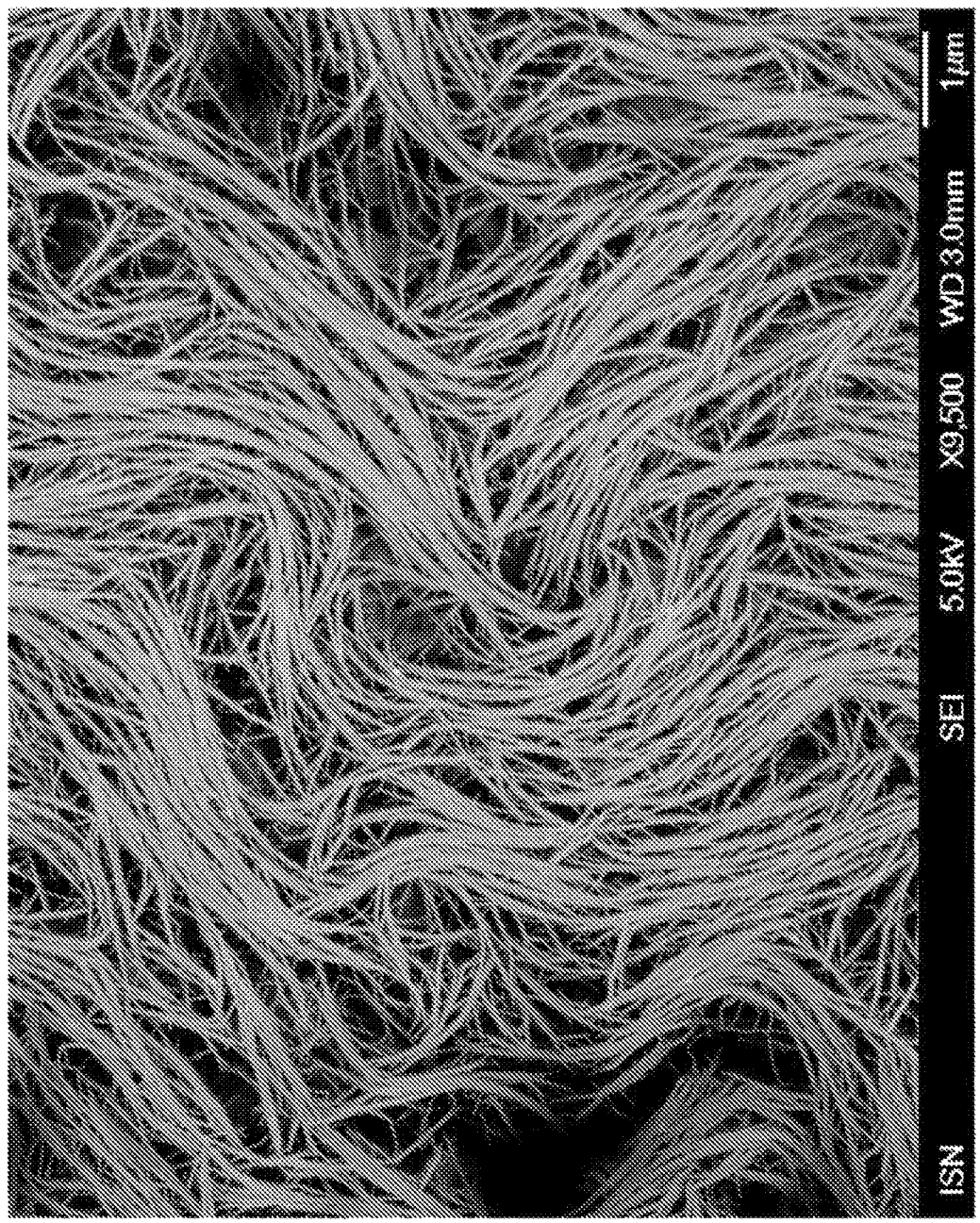

FIG. 13 shows SEM image of SC-SWCNT.

Figure 14:
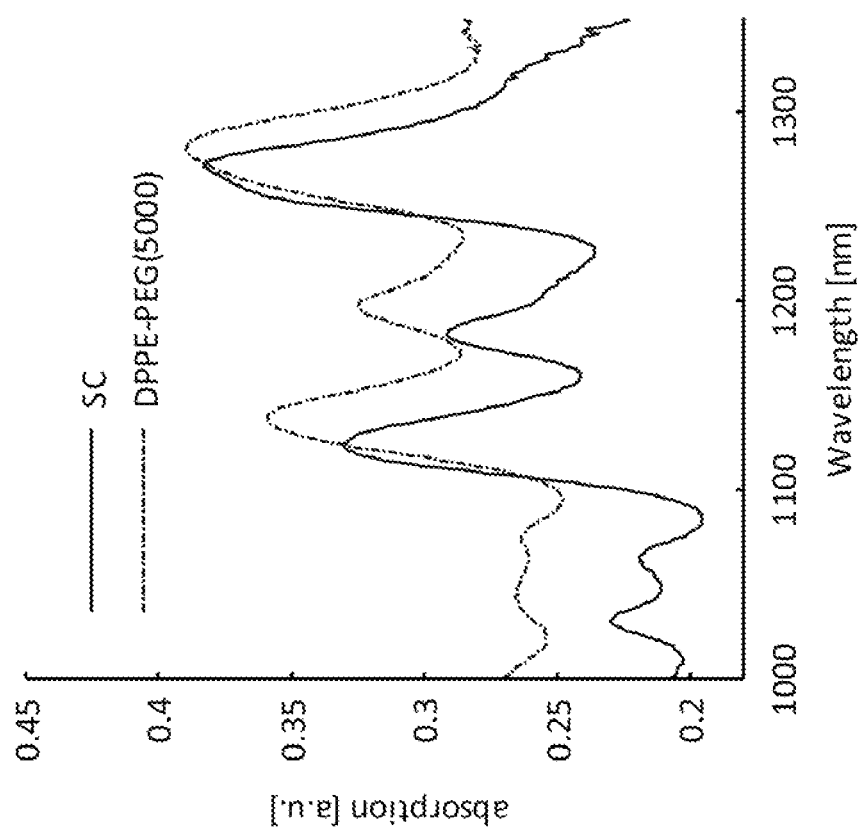

FIG. 14 shows SWCNT surfactant coating exchange. Absorption spectra of the initial sodium cholate (SC) suspended SWCNT and of DPPE-PEG(5000) suspended SWCNT following the removal of the SC by dialysis.

Figure 15A:
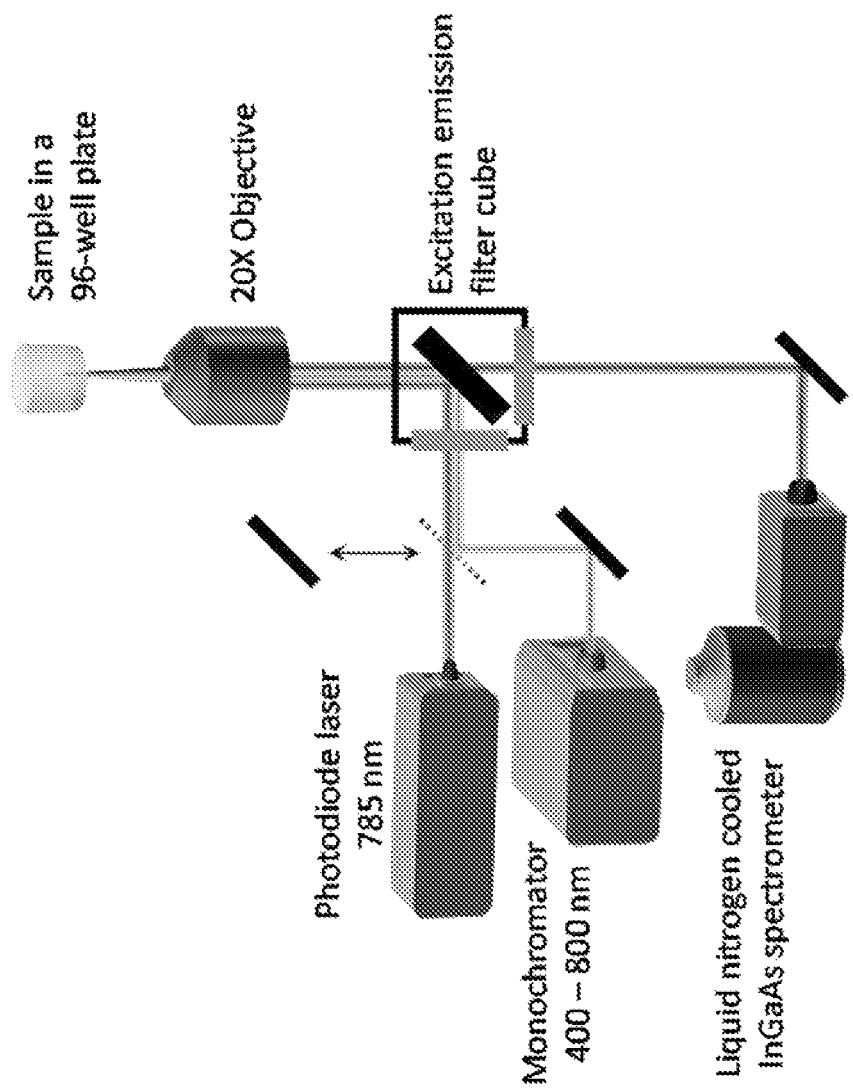
Figure 15B:
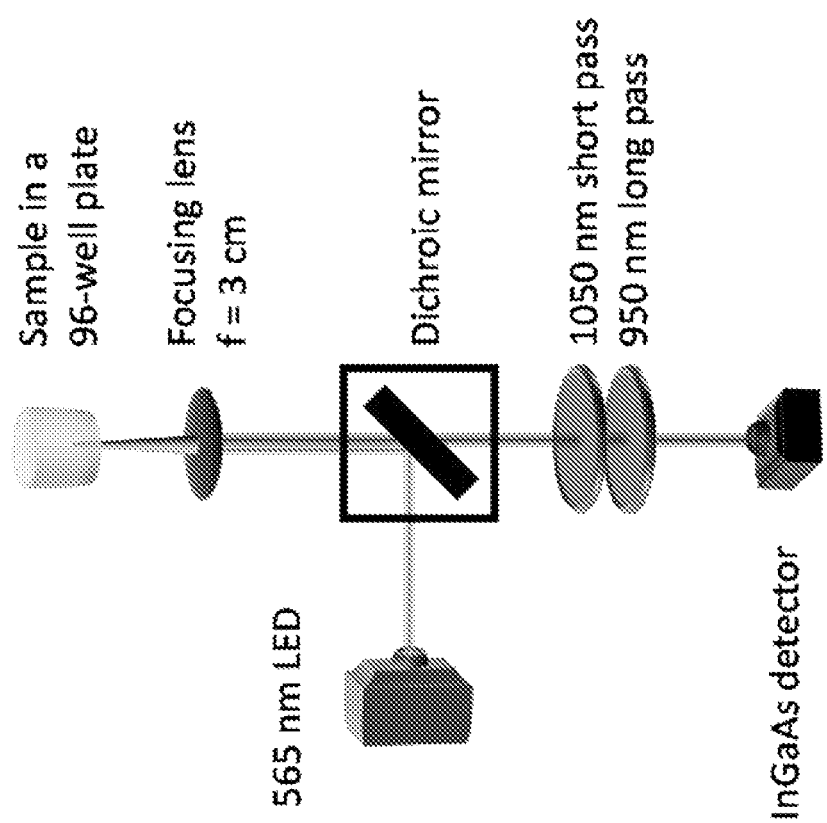

FIGS. 15A-15B show experimental microscopy systems. Optical setup of the nIR fluorescent microscopes for high throughput screening (FIG. 15A) and immobilized SWCNT sensors detection (FIG. 15B).

Figure 16:
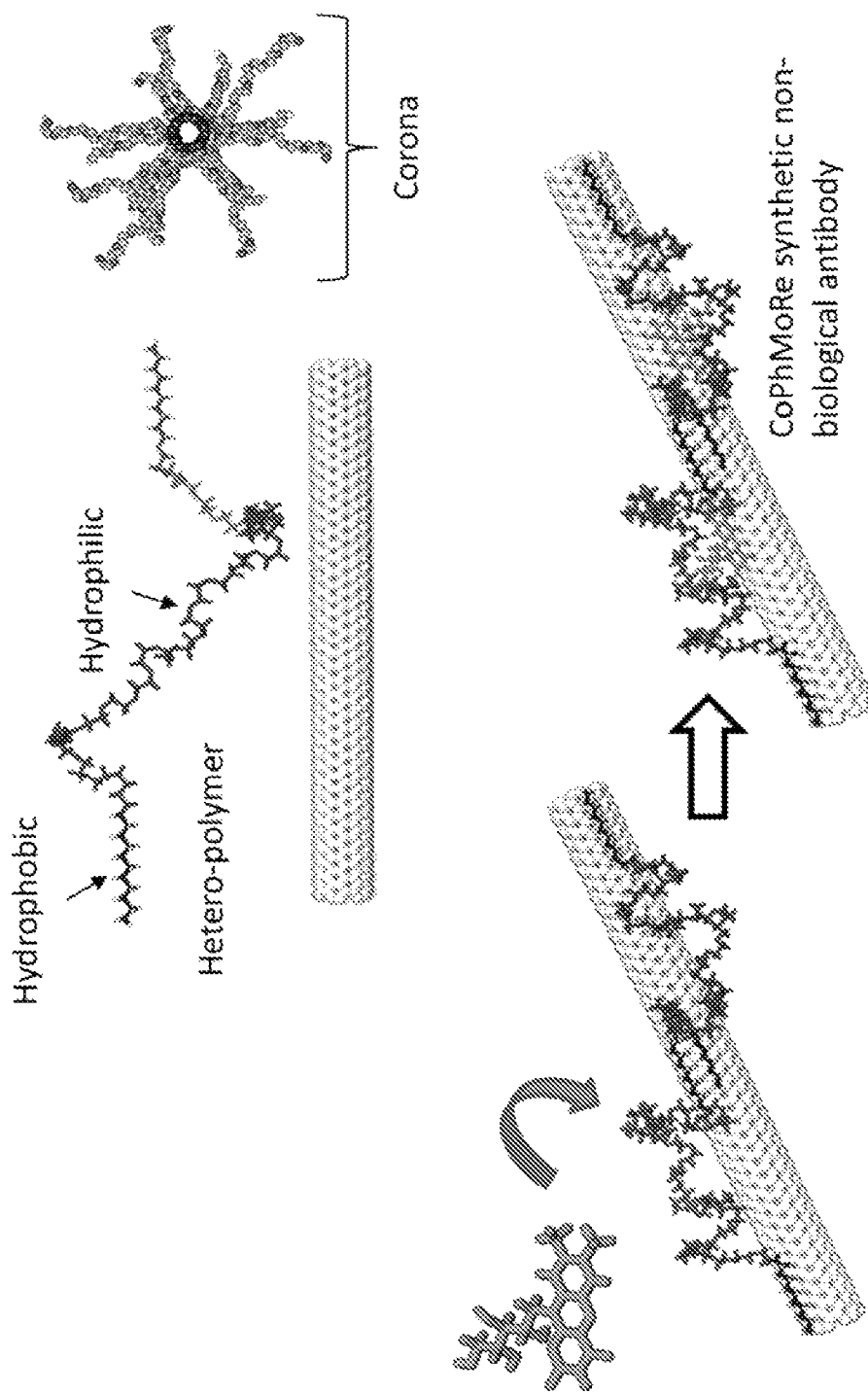

FIG. 16 shows a schematic of Corona Phase Molecular Recognition (CoPhMoRe) using a heteropolymer including hydrophilic and hydrophobic regions.

Figure 17:
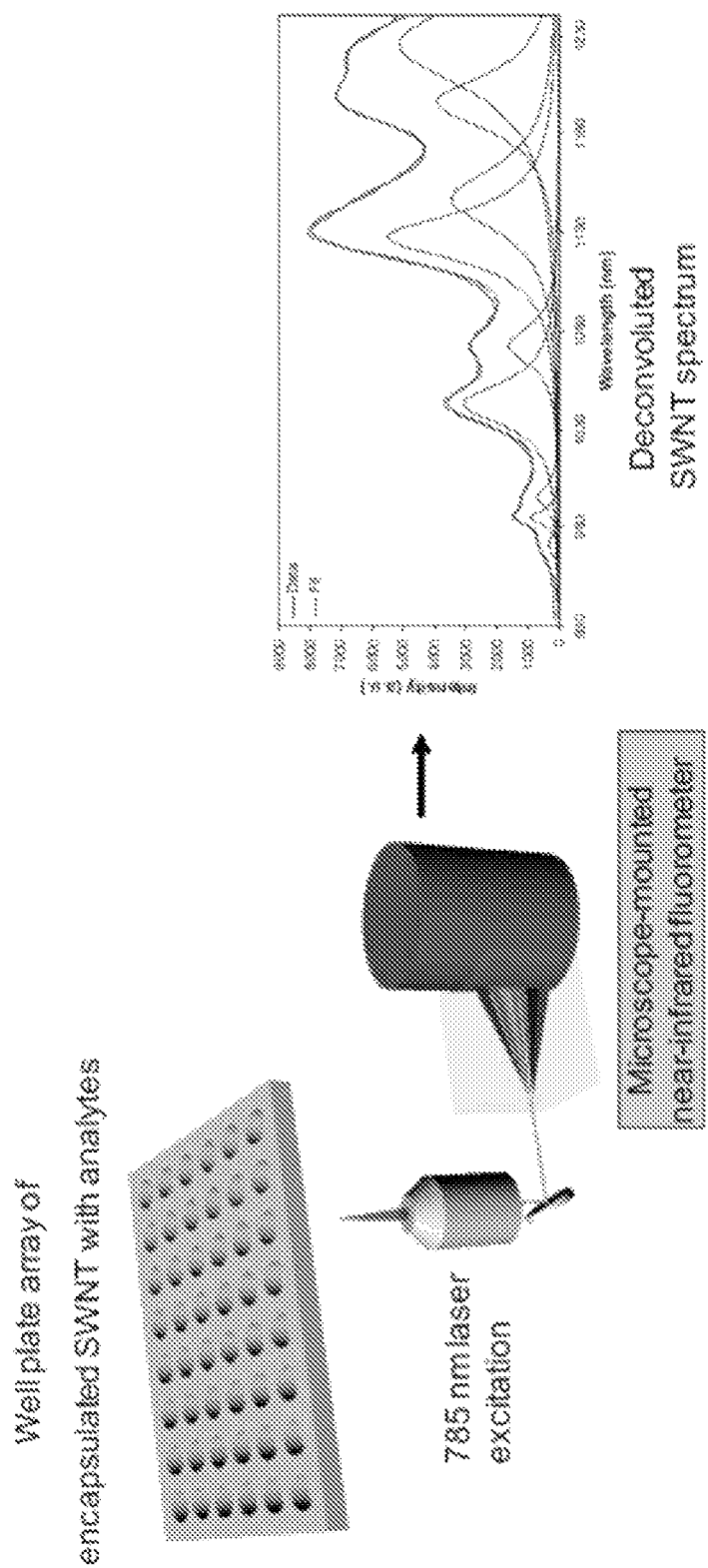

FIG. 17 shows a schematic of a system and a method for determining analytes recognized by the selective binding site in new CoPhMoRe phase using a high-throughput screening assay.

Figure 18A:
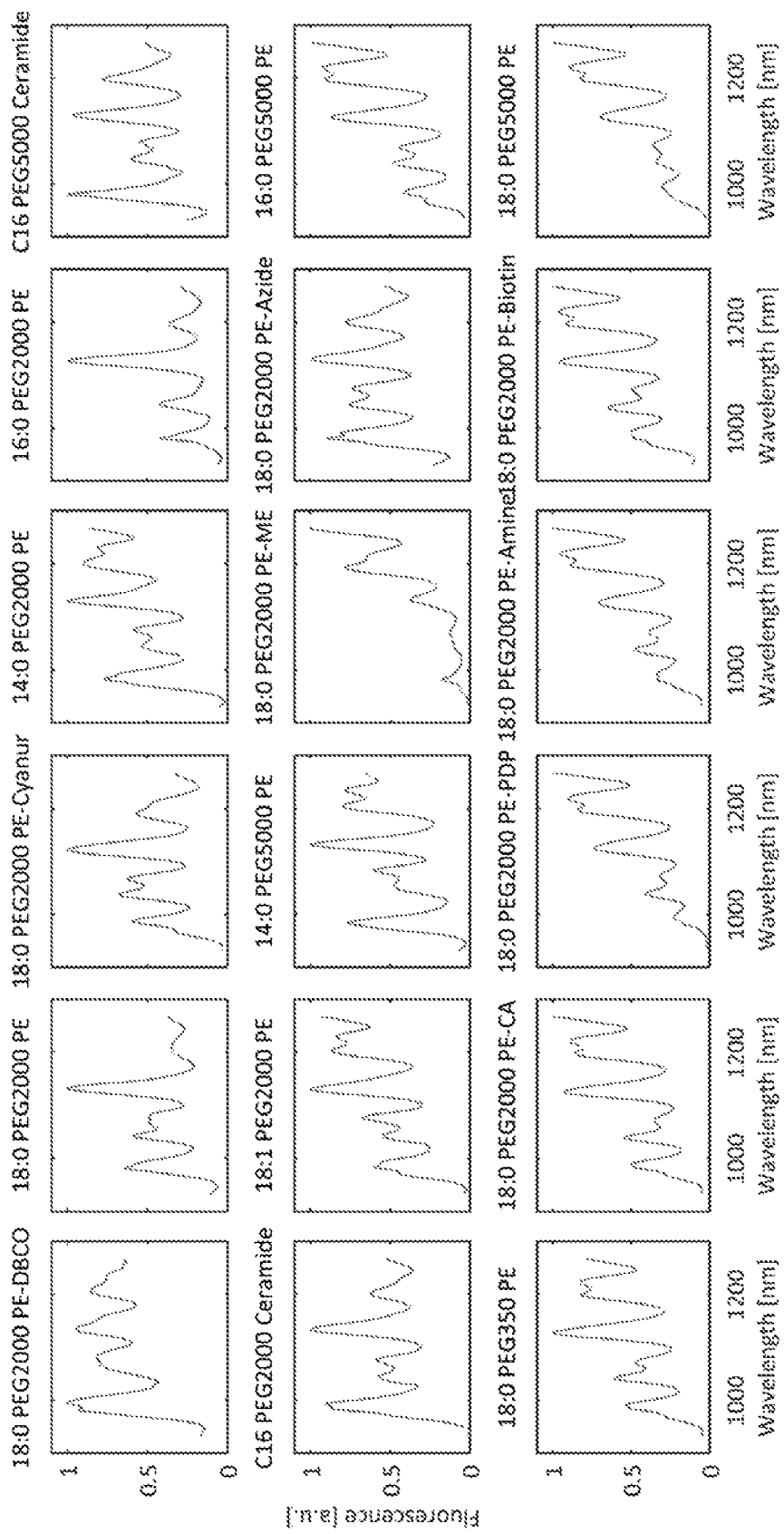
Figure 18B:
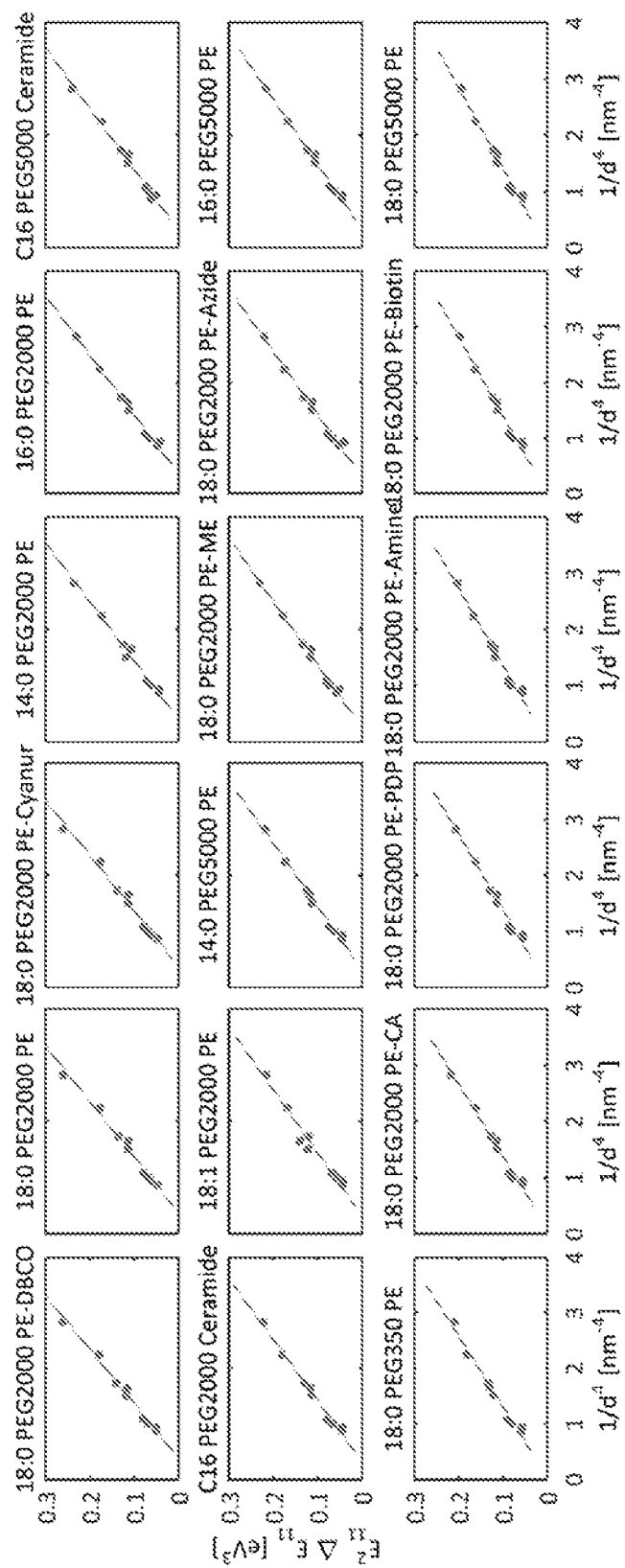
Figure 18C:
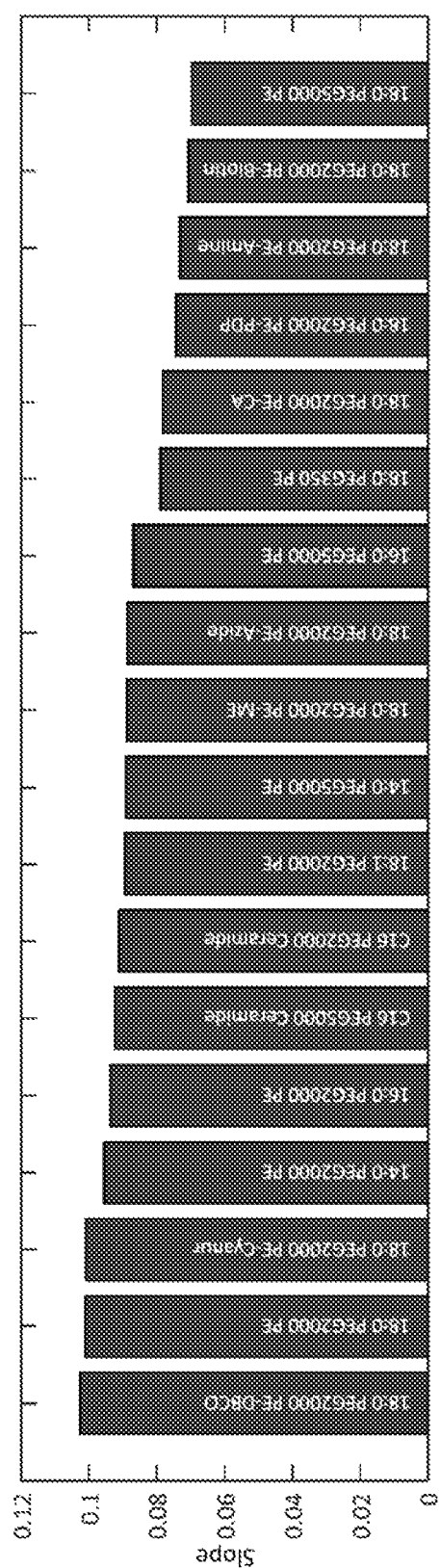

FIG. 18A shows normalize fluorescence intensity of the various SWNT suspensions used in this study. FIG. 18B shows the solvatochromic shift plotted against the diameter to the power of minus four (dots). A linear fit is plotted in line. FIG. 18C shows a bar chart showing the slope of the fit of the various SWNT suspensions in ascending order.

Figure 19A:
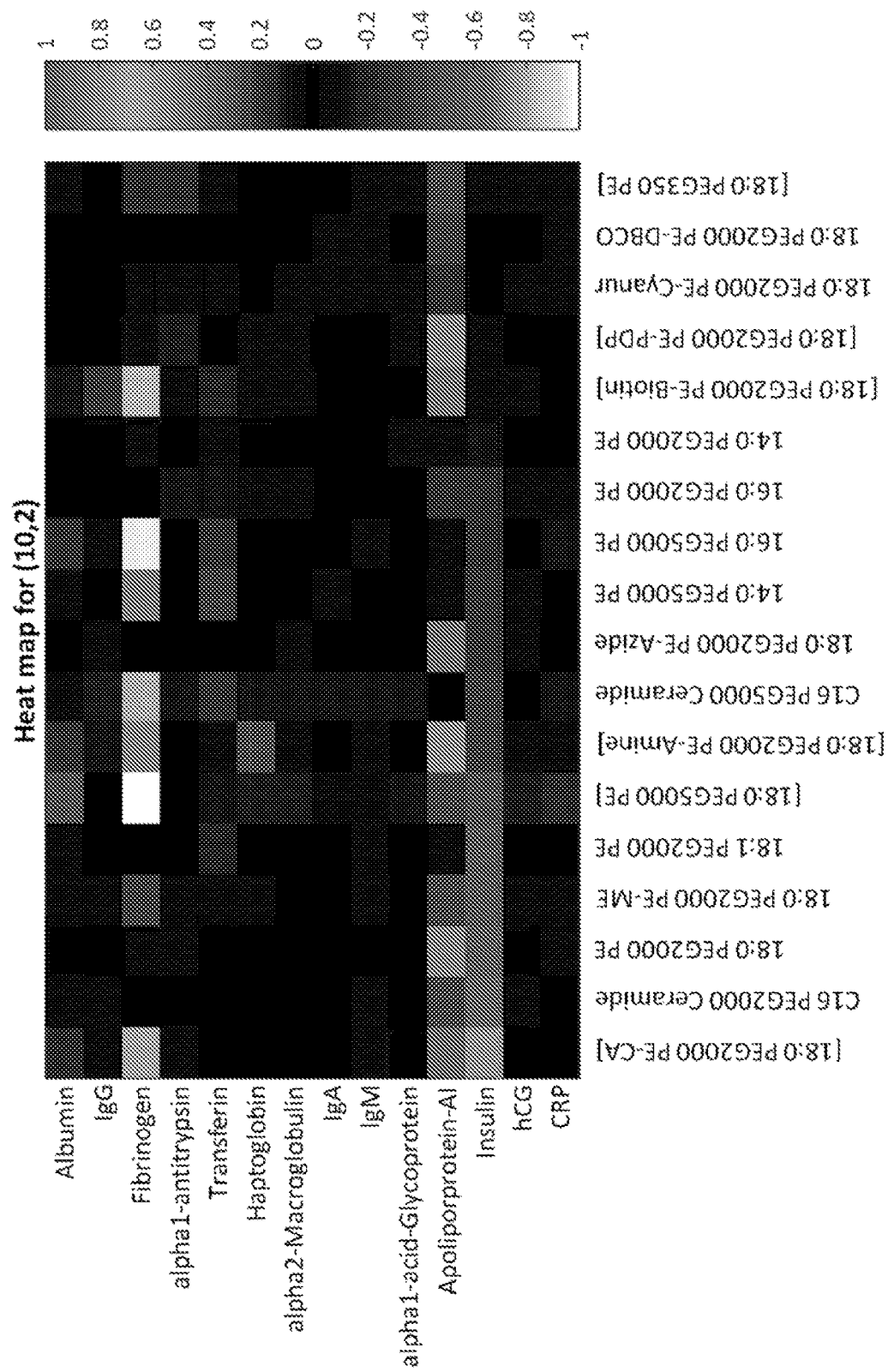
Figures 19B, 19C:
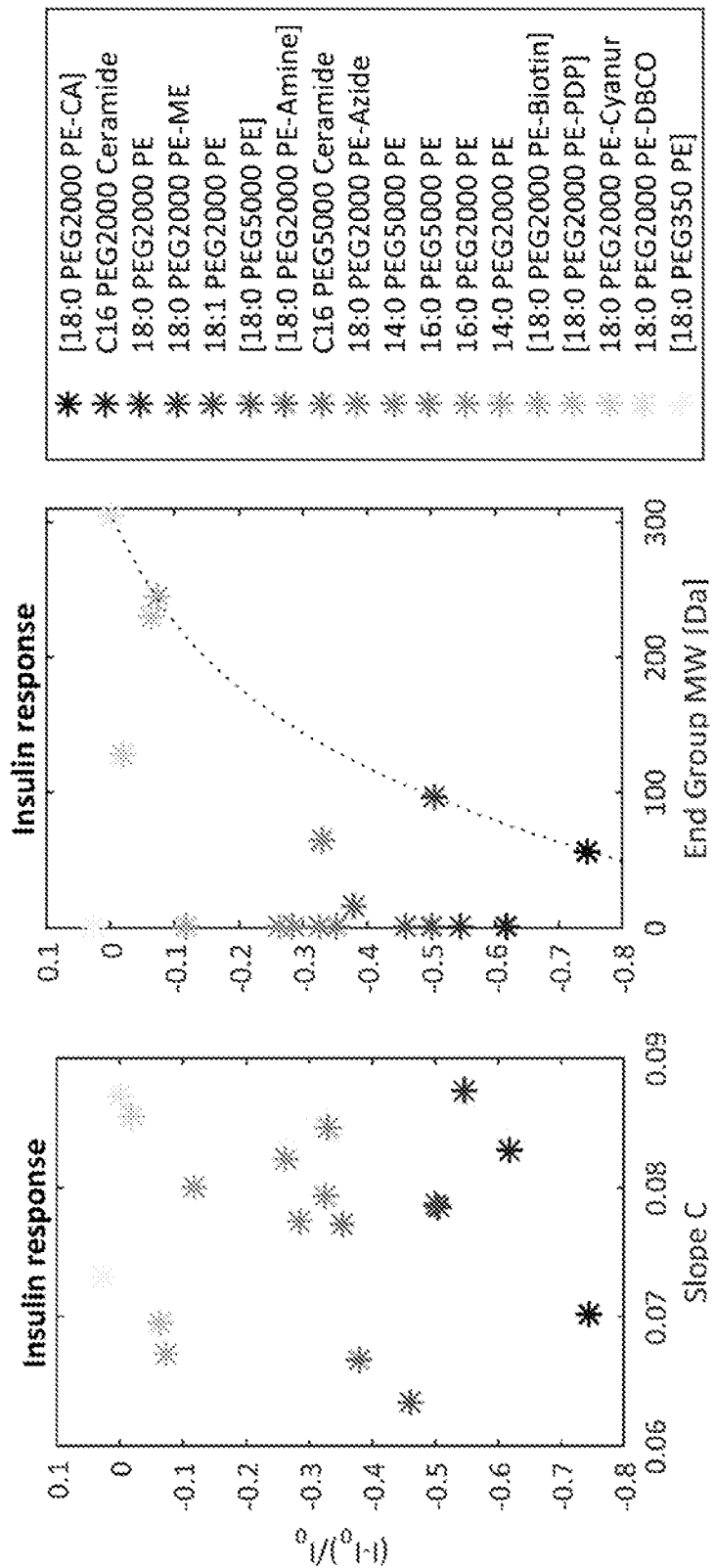

FIG. 19A shows heat map showing the relative fluorescent response of the (10,2) chirality of the various SWNT suspensions to the protein panel. FIG. 19B shows the relative fluorescent response of the SWNT suspensions is plotted against the slope of the fit of the solvatochromic shift, and FIG. 19C shows the molecular weight of the end group of the corona phase. The black dotted line is used as a guide to the eye. FIG. 19D shows the relative fluorescent response of the $C_{16}$-PEG(2000 kDa)-Ceramide—SWNT is plotted against the hydrophobic surface area of the proteins and FIG. 19E shows their isoelectric point. The two outliers, insulin and apoliporprotein-AI are identified.

Figures 20A, 20B:
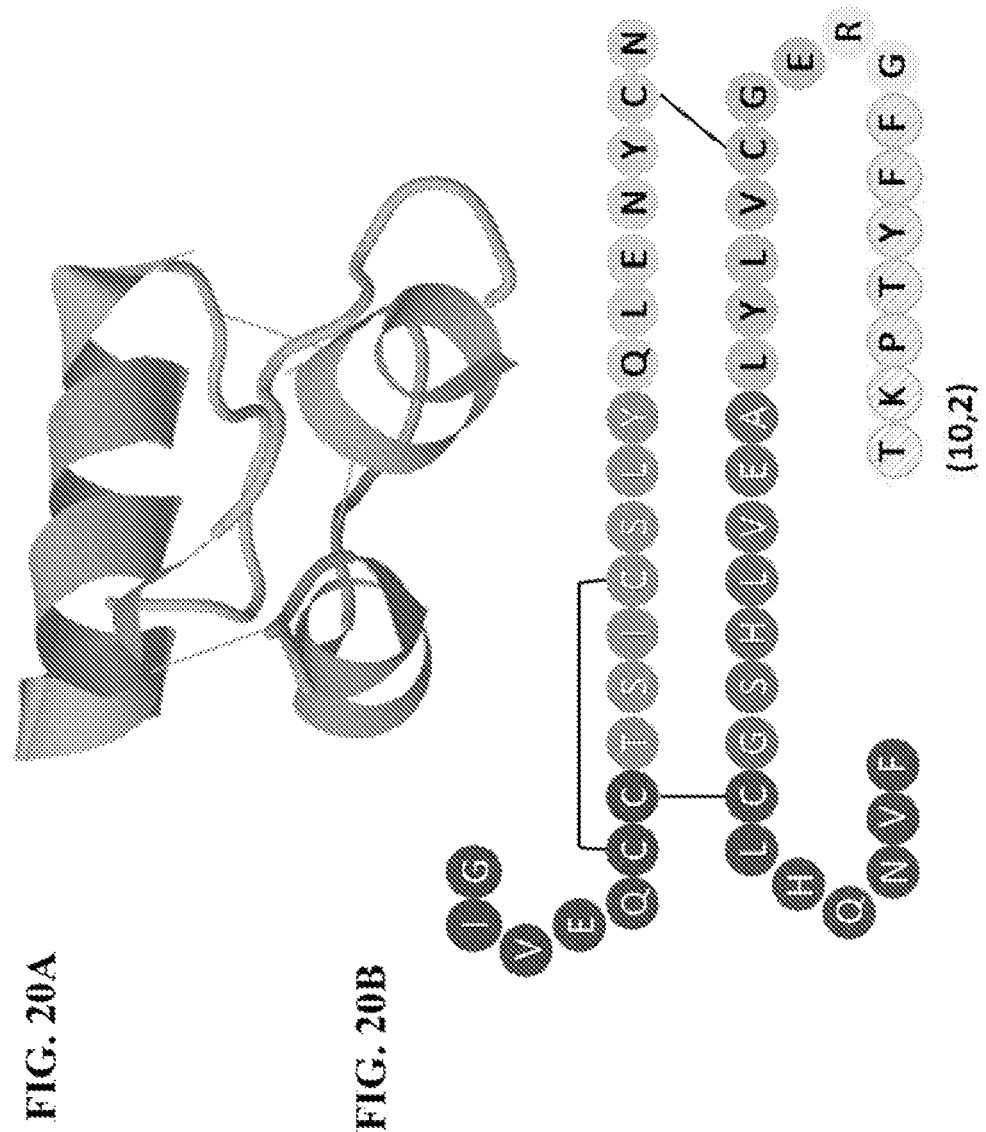
Figure 20C:
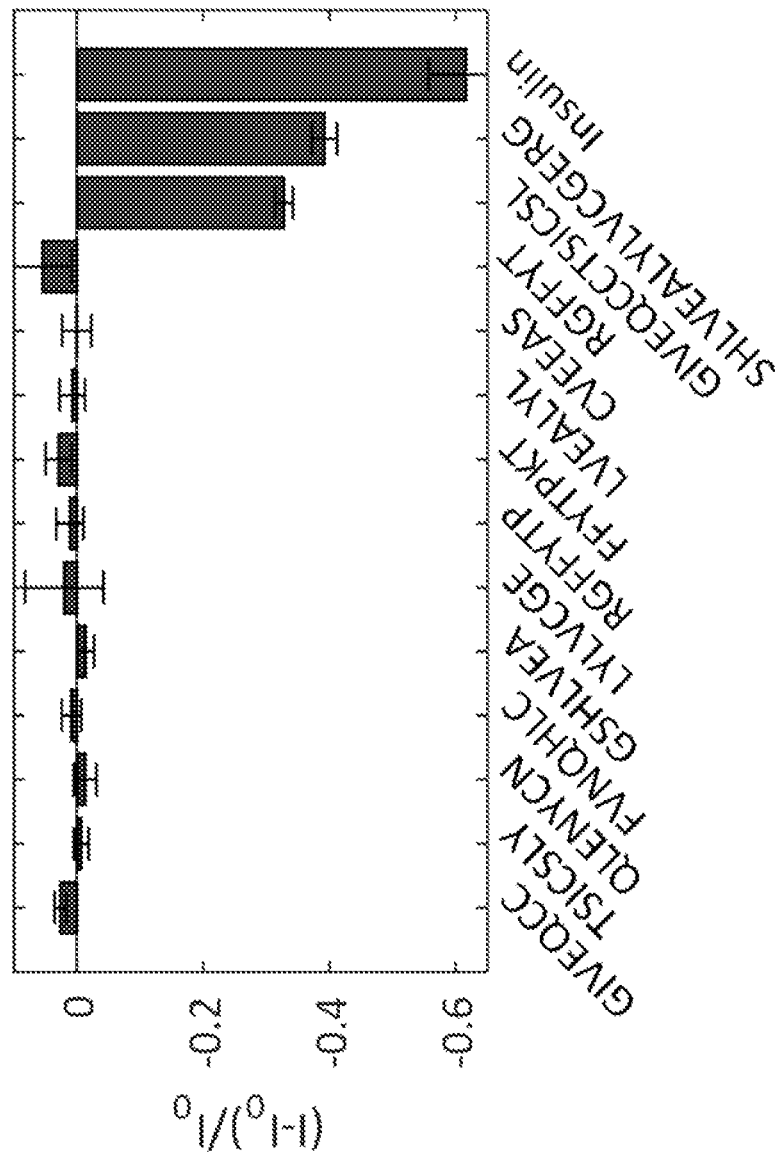

FIG. 20A shows insulin 3-dimentional structure based on the Protein Data Base (PDB) entry 3I3Z. FIG. 20B shows the α and β chains of insulin. The various insulin fragments tested are coded in different fill-colors, and filling-patterns. FIG. 20B discloses SEQ ID NOS 23-24, respectively, in order of appearance. FIG. 20C shows relative fluorescent response of the $C_{16}$-PEG(2000 kDa)-Ceramide SWNT to a peptide panel. FIG. 20C discloses SEQ ID NOS 11-19, 10 and 20-22, respectively, in order of appearance. FIG. 20D shows relative fluorescent response of the $C_{16}$-PEG(2000 kDa)-Ceramide—SWNT to a peptide panel plotted against their molecular weight.

Figure 21A:
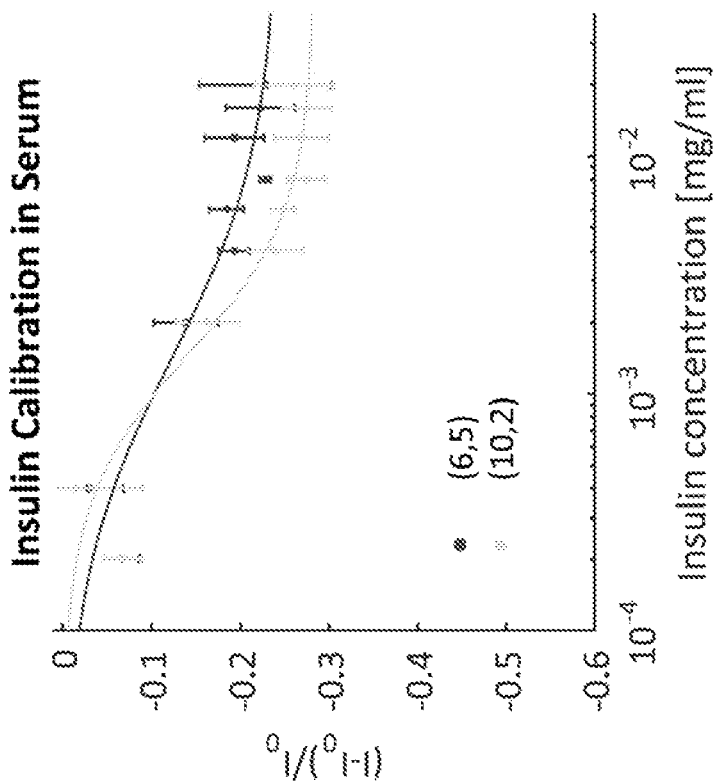
Figure 21B:
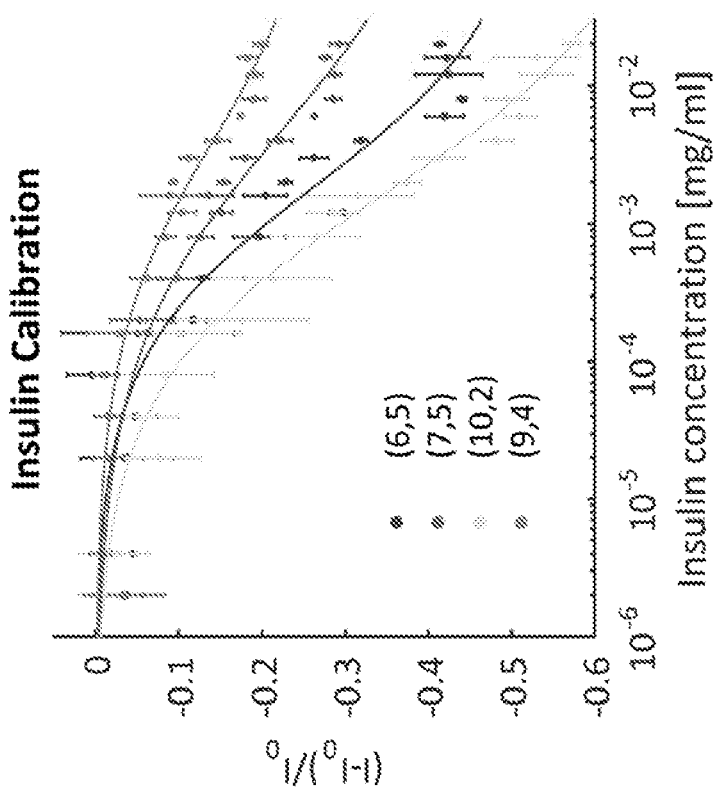
Figures 21C, 21D:
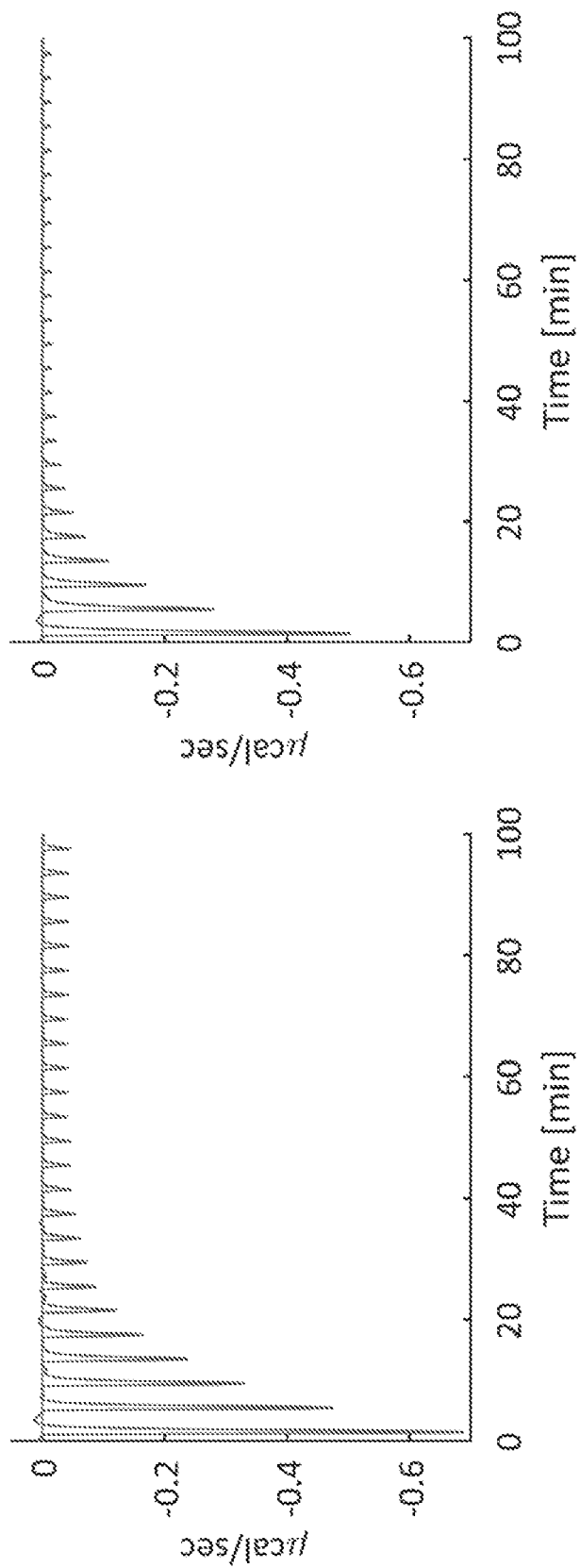
Figure 21E:
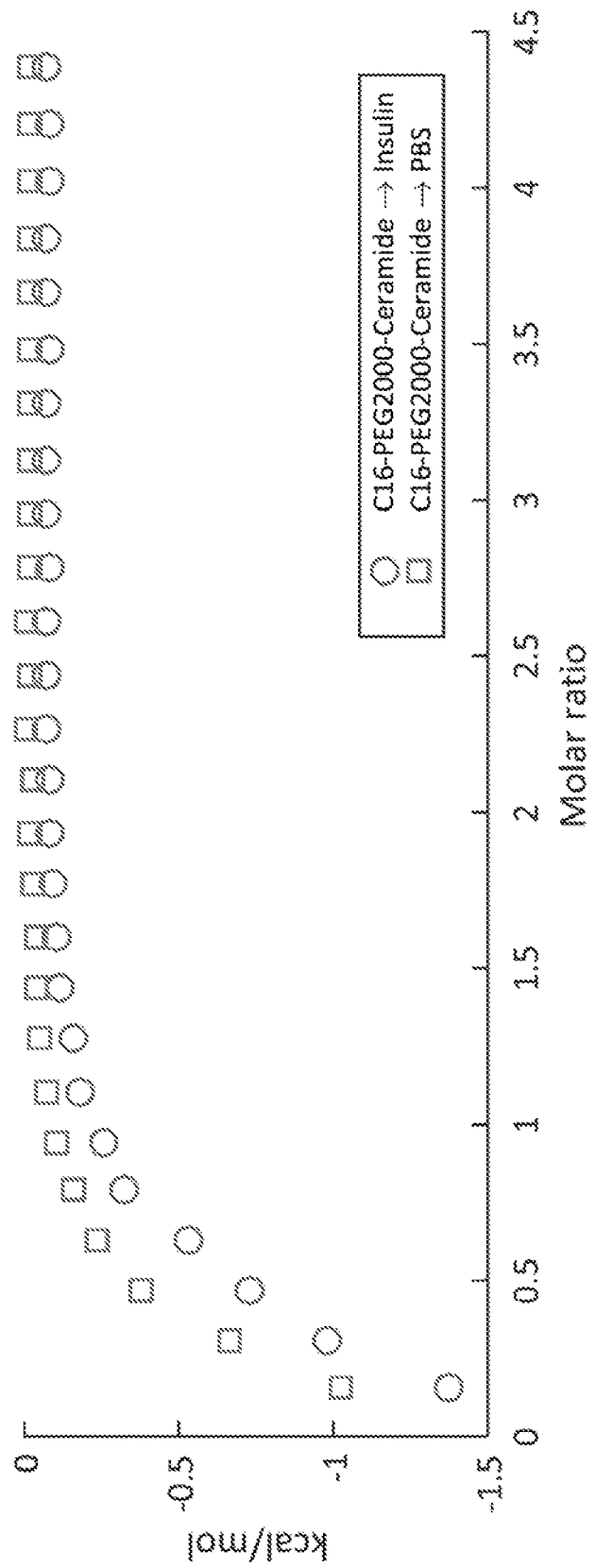

FIGS. 21A-21B show calibration curve of the insulin response versus insulin concentration for the various nanotubes chiralities, and the corresponding fits, where the experiment was conducted in PBS (FIG. 21A) or serum environment (FIG. 21B). FIGS. 21C-21D show heat changes during a titration of $C_{16}$-PEG(2000 kDa)-Ceramide into insulin solution (FIG. 21C) or PBS (FIG. 21D). FIG. 21E shows binding isotherms for the titration of $C_{16}$-PEG (2000 kDa)-Ceramide into insulin solution (circles) or PBS (squares), plotted against the molar ratio of $C_{16}$-PEG(2000 kDa)-Ceramide to insulin.

Figure 22:
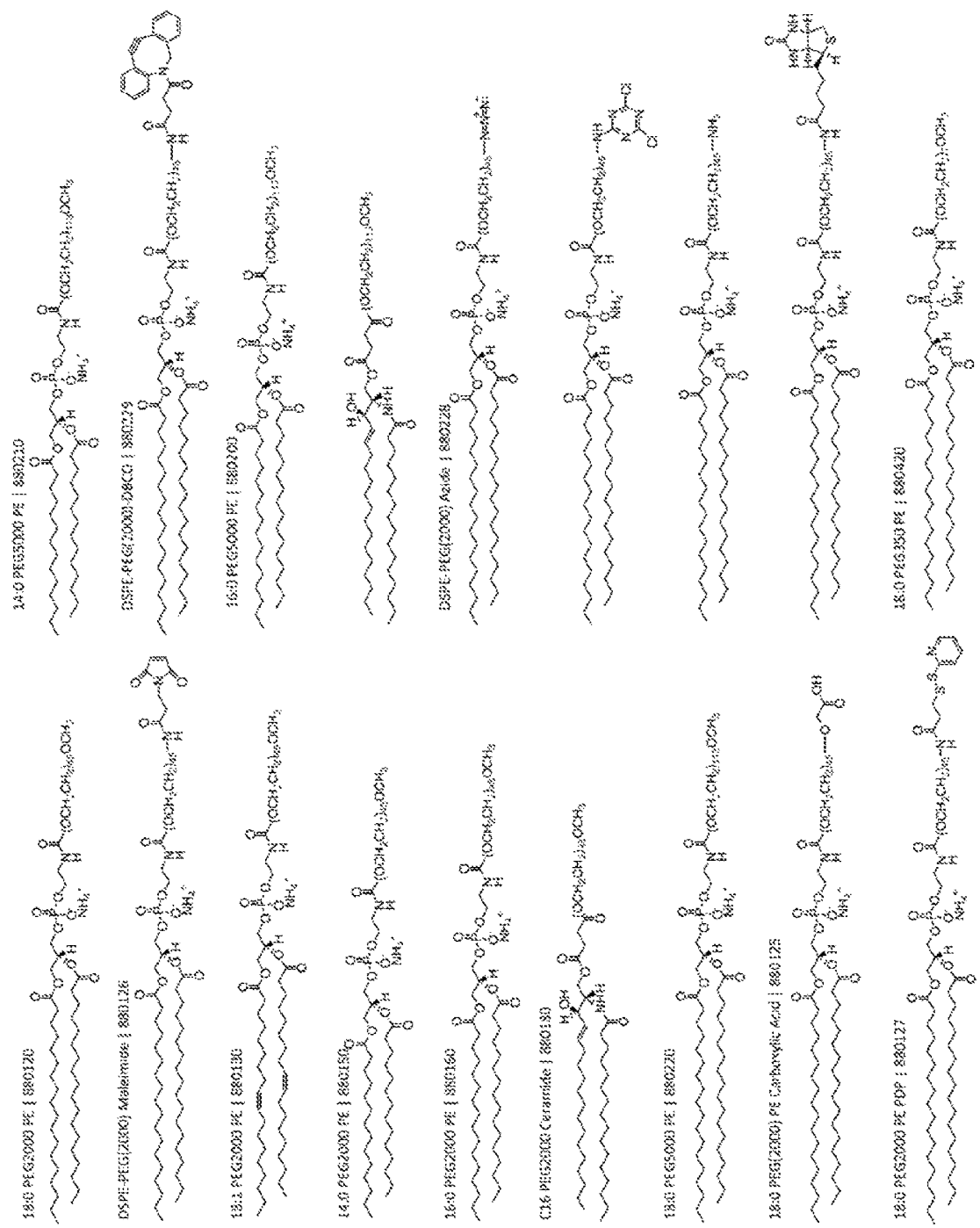

FIG. 22 shows SWCNT suspension library.

Figure 23:
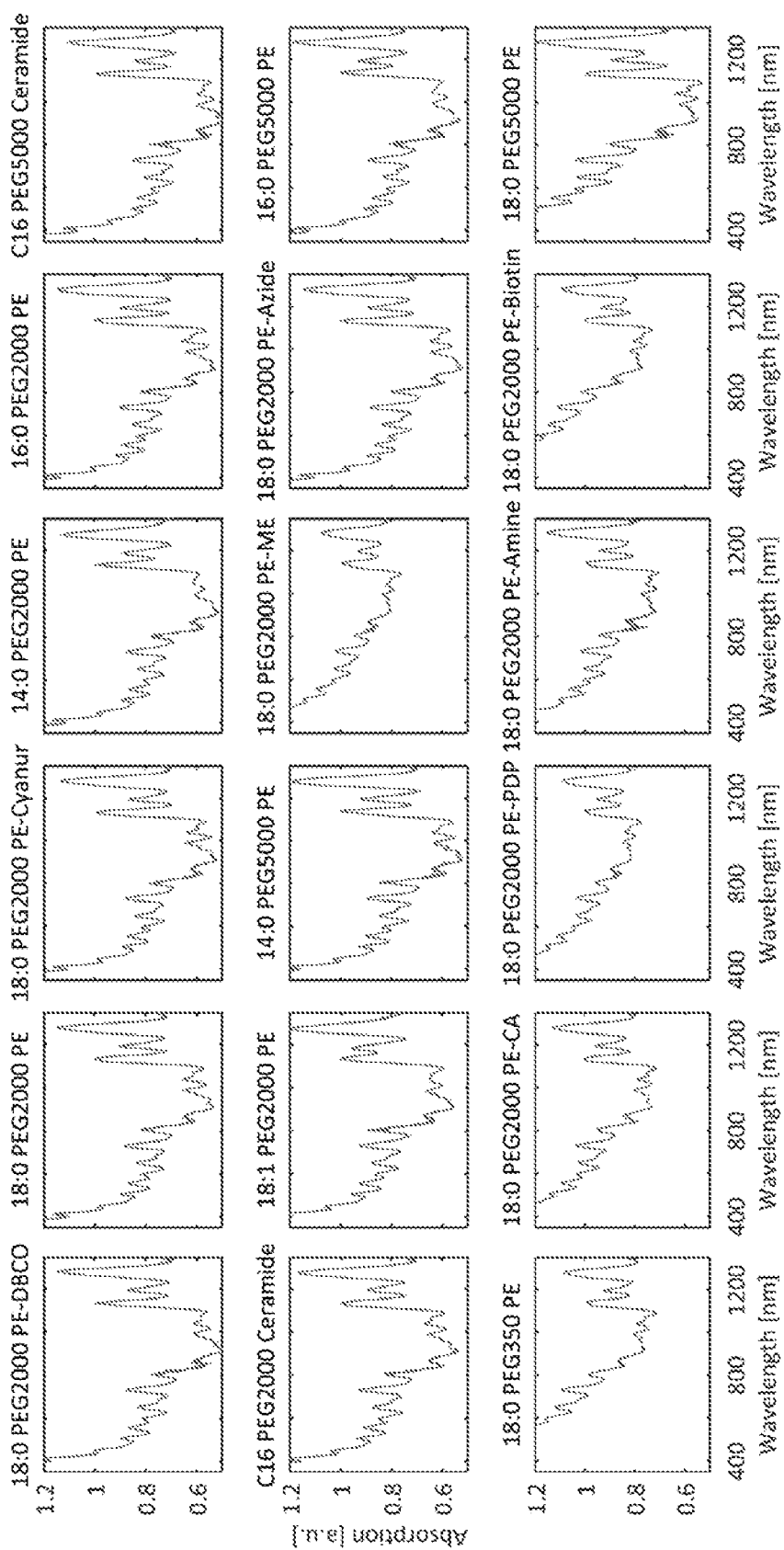

FIG. 23 shows absorption spectra of the SWCNT suspension library.

Figure 24:
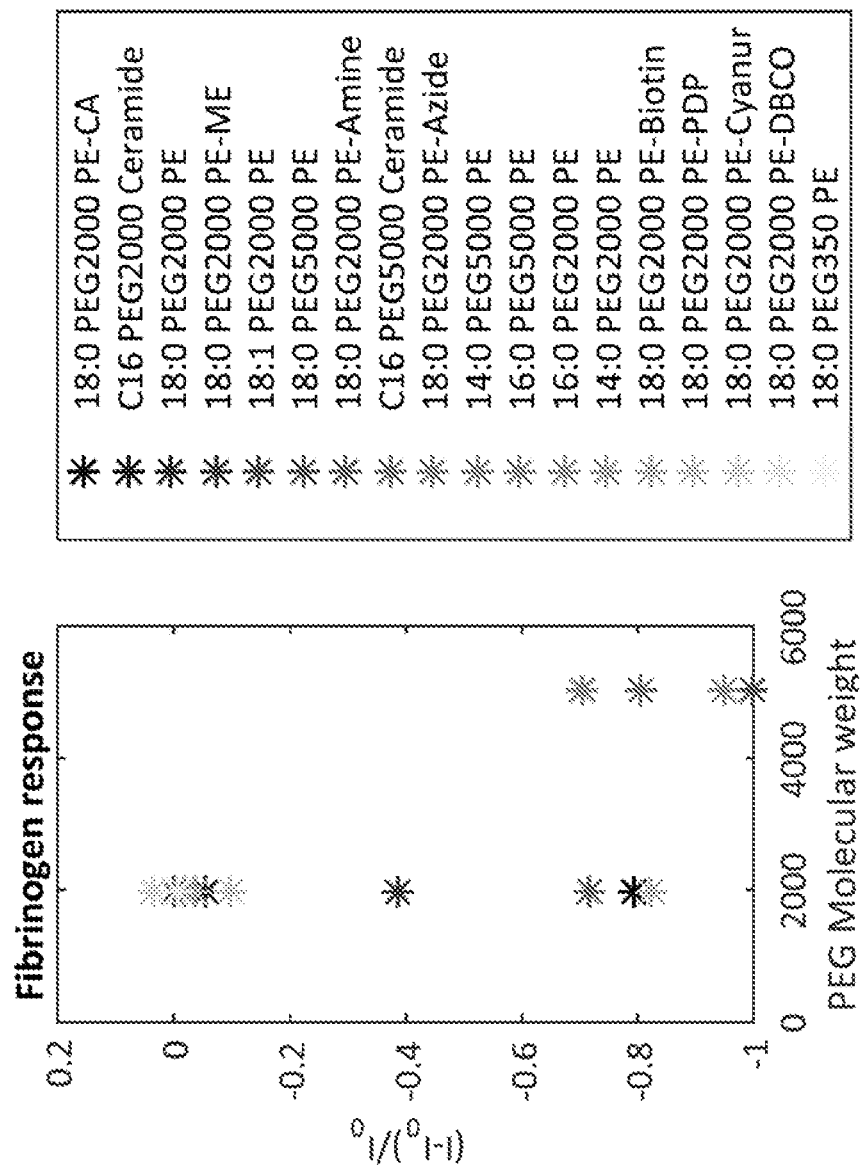

FIG. 24 shows the normalized emission intensity response of the various SWCNT suspensions to fibrinogen versus the molecular weight of the PEG chain.

Figure 25:
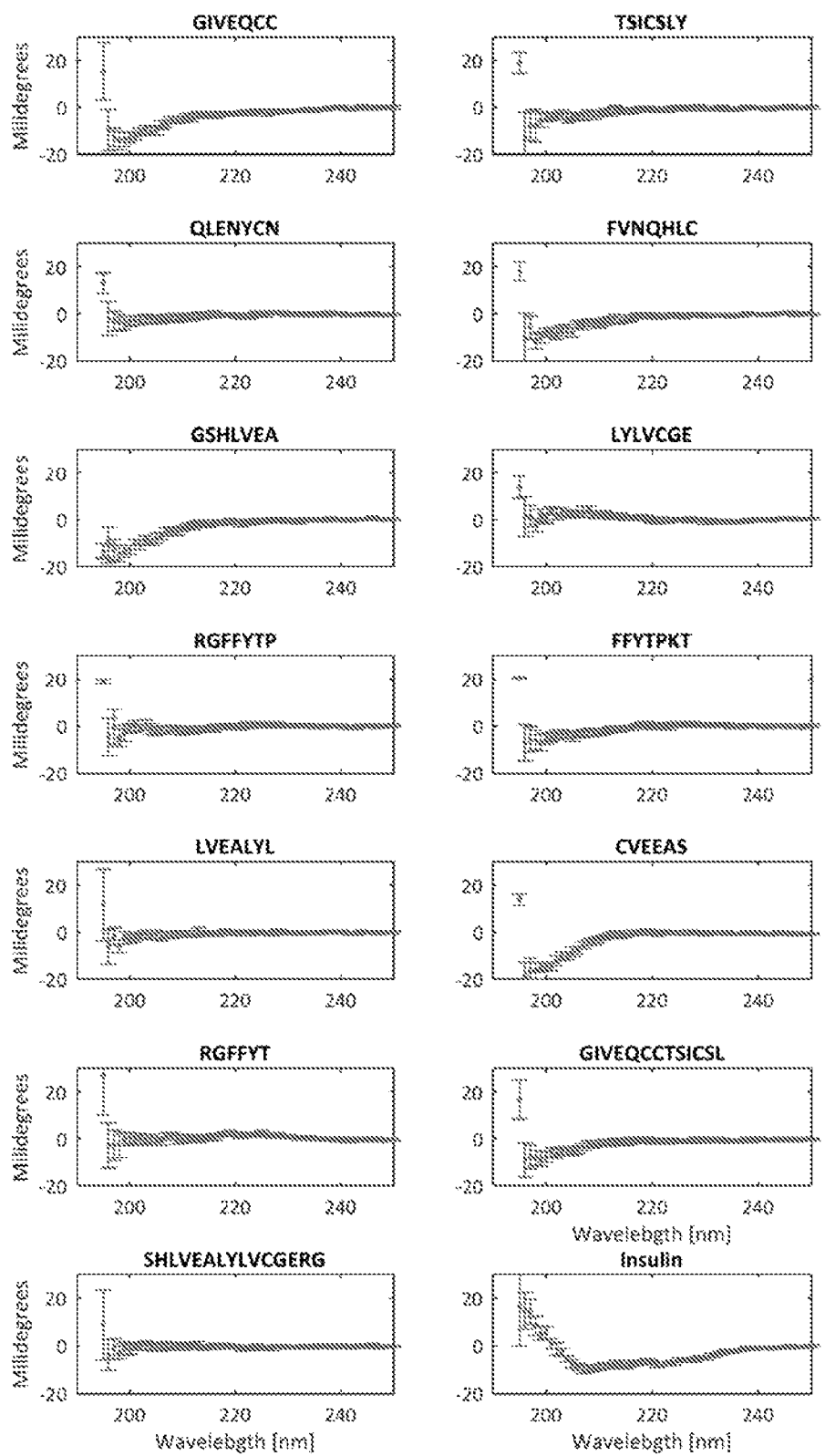

FIG. 25 shows the circular dichroism (CD) of the peptides testes. FIG. 25 discloses SEQ ID NOS 11-19, 10 and 20-22, respectively, in order of appearance.

Figure 26:
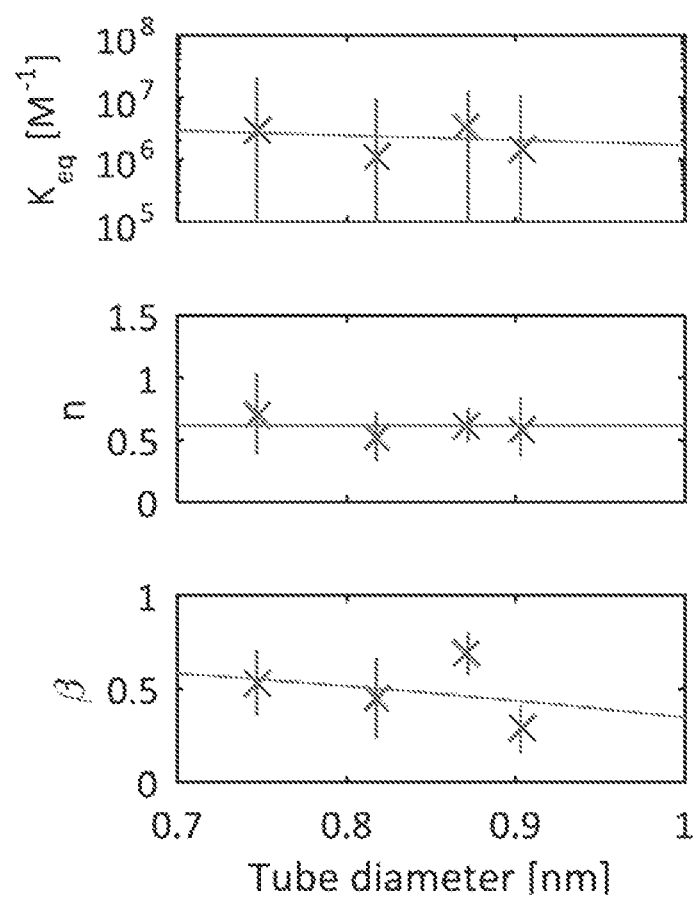

FIG. 26 shows the 3 fit-parameters (β: proportional factor, n: cooperativity Hill coefficient, $K_{eq}$: equilibrium constant) and their 95% confidence intervals.

Figure 27:
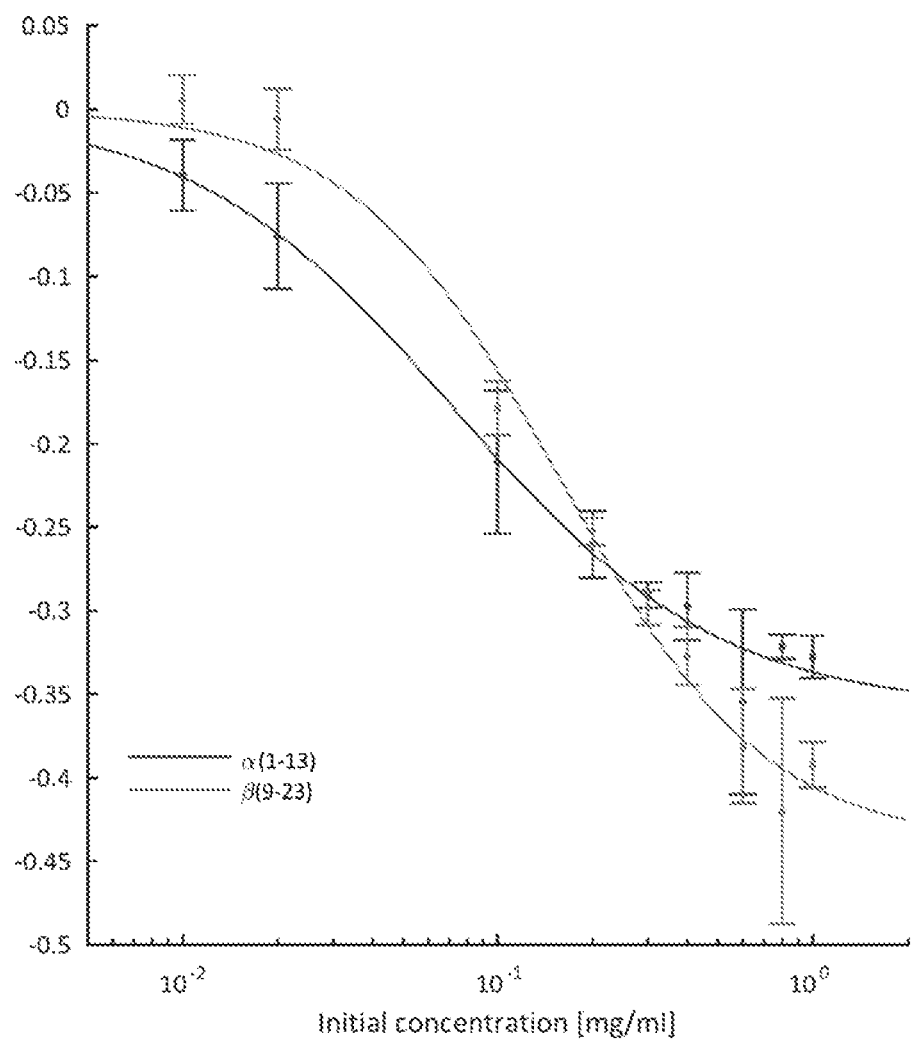

FIG. 27 shows the calibration graph of the insulin sensor response against various concentrations of the insulin α-chain (1-13), and the insulin n-chain (9-23).

DETAILED DESCRIPTION

Molecular recognition elements are central to a wide variety of applications, including chemical assays and sensors, catalysis, and directed assembly of nanoparticles. See, de Silva, A. P. et al. Signaling Recognition Events with Fluorescent Sensors and Switches. *Chemical Reviews* 97, 1515-1566 (1997), Lavigne, J. J. & Anslyn, E. V. Sensing A Paradigm Shift in the Field of Molecular Recognition: From Selective to Differential Receptors. *Angewandte Chemie International Edition* 40, 3118-3130 (2001), Alexander, C., Davidson, L. & Hayes, W. Imprinted polymers: artificial molecular recognition materials with applications in synthesis and catalysis. *Tetrahedron* 59, 2025-2057 (2003), Kumar, A., Sun, S.-S. & Lees, A. J. Directed assembly metallocyclic supramolecular systems for molecular recognition and chemical sensing. *Coordination Chemistry Reviews* 252, 922-939 (2008), Grzelczak, M., Vermant, J., Furst, E. M. & Liz-Marzán, L. M. Directed Self-Assembly of Nanoparticles. *ACS Nano* 4, 3591-3605, doi:10.1021/nn100869j (2010), and Hung, A. M. et al. Large-area spatially ordered arrays of gold nanoparticles directed by lithographically confined DNA origami. *Nat Nano* 5, 121-126 (2010), each of which is incorporated by reference in its entirety. The most advanced, generic molecular recognition schemes involve natural systems, including antibodies and aptamers. See, Kohler, G. & Milstein, C. Continuous cultures of fused cells secreting antibody of predefined specificity. *Nature* 256, 495-497 (1975), and Proske, D., Blank, M., Buhmann, R. & Resch, A. Aptamers—basic research, drug development, and clinical applications. *Appl Microbiol Biotechnol* 69, 367-374 (2005), each of which is incorporated by reference in its entirety. Molecular imprinting is one example of a purely synthetic recognition scheme, however, imprinting of biological macromolecules, such as proteins, remains challenging. See, Wulff, G. Molecular Imprinting in Cross-Linked Materials with the Aid of Molecular Templates—A Way towards Artificial Antibodies. *Angewandte Chemie International Edition* in English 34, 1812-1832 (1995), and Chen, L., Xu, S. & Li, J. Recent advances in molecular imprinting technology: current status, challenges and highlighted applications. *Chemical Society Reviews* 40, 2922-2942 (2011), each of which is incorporated by reference in its entirety.

A polymer, with little or no affinity for the target analyte, can adopt a specific conformation when adsorbed to a nanostructure via non-covalent interactions. In this approach, the polymer can be pinned in place such that a selective binding site can be created that recognizes the target molecule, and the binding event can lead to changes in the photoluminescence emitted. The polymer-nanotube composition can act as a binding partner for the analyte, which results in a detectable change in photoluminescence. No labeling is needed in this technique; however, labeling can be performed. For example, one or more fluorescent dyes can be conjugated to the polymer through covalent reaction with a functionality along the polymer backbone or at a polymer terminus.

A systematic design of polymers for understanding molecular structures of polymers that are capable of complexing or interacting with a nanostructure can include adjusting the hydrophilic and hydrophobic regions of the polymer forming a heteropolymer (FIG. 16). Corona Phase Molecular Recognition (CoPhMoRe) is a generic molecular recognition scheme using a nanoparticle surface to template a heteropolymer. An adsorbed phase of a surfactant or a polymer on a nanoparticle, called the corona, and normally selected from a library of such molecules, is necessarily constrained and structured by the molecular interactions with the nanoparticle surface. CoPhMoRe is achieved when a heteropolymer—nanoparticle hybrid selectively binds a target analyte owing to the structure adopted by the polymer when folded onto the particle surface. In practice, a CoPhMoRe screen of a heteropolymer or surfactant library is accelerated if the underlying nanoparticle has an optical response to the molecular binding event, allowing for high throughput detection of the selective phase (FIG. 17).

Near infrared (nIR) fluorescent single walled carbon nanotubes (SWCNT) can be used as an underlying reporter of this molecular interaction, where non-covalent functionalization was used to produce distinct corona phases. See, Bisker, G., Iverson, N. M., Ahn, J. & Strano, M. S. A Pharmacokinetic Model of a Tissue Implantable Insulin Sensor. *Advanced Healthcare Materials* 4, 87-97 (2015), Mu, B. et al. Recent Advances in Molecular Recognition Based on Nanoengineered Platforms. *Accounts of Chemical Research*, doi:10.1021/ar400162w (2014), Kruss, S. et al. Carbon nanotubes as optical biomedical sensors. *Advanced Drug Delivery Reviews* 65, 1933-1950 (2013), Landry, M. et al. Experimental Tools to Study Molecular Recognition within the Nanoparticle Corona. *Sensors* 14, 16196-16211 (2014), Iverson, N. M. et al. In vivo biosensing via tissue-localizable near-infrared-fluorescent single-walled carbon nanotubes. *Nat Nano* 8, 873-880, doi:10.1038/nnano.2013.222 (2013), Zhang, J. et al. Molecular recognition using corona phase complexes made of synthetic polymers adsorbed on carbon nanotubes. *Nat Nano* 8, 959-968 (2013), Kruss, S. et al. Neurotransmitter Detection Using Corona Phase Molecular Recognition on Fluorescent Single-Walled Carbon Nanotube Sensors. *Journal of the American Chemical Society* 136, 713-724 (2013), Welsher, K. et al. A route to brightly fluorescent carbon nanotubes for near-infrared imaging in mice. *Nat Nano* 4, 773-780 (2009), Giraldo, J. P. et al. A Ratiometric Sensor Using Single Chirality Near-Infrared Fluorescent Carbon Nanotubes: Application to In Vivo Monitoring. *Small*, doi:10.1002/sml1.201403276 (2015), and Oliveira, S. F. et al. Protein Functionalized Carbon Nanomaterials for Biomedical Applications. *Carbon* 95, 767-779 (2015), each of which is incorporated by reference in its entirety.

CoPhMoRe screening for small molecules normally proceeds with the construction of a heteropolymer library such that each element can suspend the nanoparticle (SWCNT in this case) creating an array of colloidal dispersions. See, Zhang, J. et al. Molecular recognition using corona phase complexes made of synthetic polymers adsorbed on carbon nanotubes. *Nat Nano* 8, 959-968 (2013), and Kruss, S. et al. Neurotransmitter Detection Using Corona Phase Molecular Recognition on Fluorescent Single-Walled Carbon Nanotube Sensors. *Journal of the American Chemical Society* 136, 713-724 (2013), each of which is incorporated by reference in its entirety. The specific synthetic polymers for library screening necessarily have hydrophobic segments or moieties that adsorb onto the hydrophobic surface of the SWCNT, pushing hydrophilic segments into solution. The composition of the polymer controls the specific configuration, either static or dynamic, that can recognize a target analyte of interest. For small molecules, the interaction between the polymer, nanotube and analyte can be described using a 2D Equation of State model, allowing reasonably accurate prediction of molecular recognition. See, Ulissi, Z. W., Zhang, J Sresht, V., Blankschtein, D. & Strano, M. S. 2D Equation-of-State Model for Corona Phase Molecular Recognition on Single-Walled Carbon Nanotube and Graphene Surfaces. *Langmuir* 31, 628-636 (2014), which is incorporated by reference in its entirety. In the case of SWCNT, high throughput fluorescence spectroscopy that scans for spectral changes associated with analyte binding as either fluorescent intensity or emission wavelength modulation can then be used to identify CoPhMoRe phases. Previous work has demonstrated CoPhMoRe SWCNT sensors for riboflavin, L-thyroxine, and estradiol, utilizing boronic acid-substituted phenoxy-dextran, polyethylene glycol (PEG) brush, and rhodamine isothiocyanate (RITC) difunctionalized-PEG SWCNT coronae, respectively. See, Zhang, J. et al. Molecular recognition using corona phase complexes made of synthetic polymers adsorbed on carbon nanotubes. *Nat Nano* 8, 959-968 (2013), which is incorporated by reference in its entirety. Additionally, a variety of DNA oligonucleotides demonstrated discrimination among a panel of neurotransmitters. See, Kruss, S. et al. Neurotransmitter Detection Using Corona Phase Molecular Recognition on Fluorescent Single-Walled Carbon Nanotube Sensors. *Journal of the American Chemical Society* 136, 713-724 (2013), which is incorporated by reference in its entirety. Despite initial success with small organic molecules detection, CoPhMoRe has not yet been adapted or demonstrated for macromolecules, with an open question of whether such coronae are capable of the large area, selective interactions necessary to discriminate between soluble proteins.

Although antibodies can be raised to identify both small and macro-molecular targets alike, the need of a living organism for production poses a limitation in high throughput exploratory research. See, Jayasena, S. D. Aptamers: An Emerging Class of Molecules That Rival Antibodies in Diagnostics. *Clinical Chemistry* 45, 1628-1650 (1999), which incorporated by reference in its entirety. In principle, a pinned configuration of a specific polymer could be found such that it maps the contours and localized chemical affinities of a certain face of a protein analyte (see. Bisker, G. et al. A Mathematical Formulation and Solution of the CoPhMoRe Inverse Problem for Helically Wrapping Polymer Corona Phases on Cylindrical Substrates. *The Journal of Physical Chemistry C* 119, 13876-13886 (2015). which is incorporated by reference in its entirety), but experimental realization of this has not yet been demonstrated. As a synthetic approach for recognizing these biological molecules, it is possible that protein CoPhMoRe would find extensive use in a variety of sensor and assay arrangements where degradation, stability, cost, and production scale prevent natural recognition elements from being employed.

Each of the fluorescent moiety and the polymer backbone moiety can be selected to have a length of a hydrophilic region and length of a hydrophobic region configured to interact in with a nanostructure. Selecting can include adjusting the length of the polymer moiety. Therefore, in addition to interacting with an analyte, the systemically designed polymer can suspend a nanoparticle in an aqueous solution. The length and hydrophilicity of the hydrophilic regions can be altered to achieve the desired solubility. For example, the molecular weight of a PEG conjugate can be increased or decreased to alter the solubility of composition including the polymer and a nanoparticle. In another example, a conjugate of the polymer with another moiety can be formed. The other moiety can be a fluorescent moiety which is coupled to a selected polymer backbone moiety.

For example, the polymer can be designed to have structures that are simple enough to allow for distinct fluorescence responses for different molecules, while also enabling polymer-nanostructure complexes to be simulated with, for example, molecular dynamics simulation or mean-field based model. For example, fluorescein or rhodamine can be conjugated with polyethylene glycol polymers. These conjugate polymers can be designed to provide fluorophores on the polymers that can assist in identifying structural information of the polymer-nanostructure complexes or to study the basics of the interactions between the nanostructure and the polymer. Hydrophilic regions of the polymer can extend into water, while hydrophobic regions can interact with nanostructure surface. Therefore, the length of the hydrophilic region can be tuned by the molecular weights of the polymer, for example, a polyethylene glycol (PEG).

A conjugate can be formed by reaction between one or more of a carboxylic acid, ester, aldehyde, aldehyde hydrate, acetal, hydroxy, protected hydroxy, carbonate, alkenyl, acrylate, methacrylate, acrylamide, substituted or unsubstituted thiol, halogen, substituted or unsubstituted amine, protected amine, hydrazide, protected hydrazide, succinimidyl, isocyanate, isothiocyanate, dithiopyridine, vinylpyridine, iodoacetamide, epoxide, hydroxysuccinimidyl, azole, maleimide, sulfone, allyl, vinylsulfone, tresyl, sulfo-N-succinimidyl, dione, mesyl, tosyl, or glyoxal. Specific examples can include N-succinimidyl carbonate, amine, hydrazide, succinimidyl propionate, succinimidyl butanoate, succinimidyl succinate, succinimidyl ester, benzotriazole carbonate, glycidyl ether, oxycarbonylimidazole, p-nitrophenyl carbonate, aldehyde, maleimide, or orthopyridyl-disulfide, vinylsulfone.

In other circumstances, the polymer can be branched or modified in other ways to alter or adjust the properties of the complex. For example, the polymer can be a comb, brush or star-burst polymer. For example, the polymer can be branched, having 2-20 arms. In certain examples, the branched polymer can be a polyethylene glycol polymer having 2, 4 or 8 arm groups.

Generally, the composition can include a complex and a selective binding site associated with the complex. The complex can include a nanostructure and a polymer, the polymer being free from selective binding to an analyte in the absence of being adsorbed on the nanostructure. The polymer can be adsorbed on the nanostructure. The nanostructure can be a photoluminescent nanostructure.

A nanostructure can be an article having at least one cross-sectional dimension between opposed boundaries of less than about 1 micron. In some embodiments, nanostructures can have at least one cross-sectional dimension between opposed boundaries of less than about 500 nm, less than about 250 nm, less than about 100 nm, less than about 75 nm, less than about 50 nm, less than about 25 nm, less than about 10 nm, or, in some cases, less than about 1 nm. Examples of nanostructures can include nanotubes (including carbon nanotubes), nanowires (including carbon nanowires), graphene and quantum dots, among others. In some embodiments, the nanostructures can include a fused network of atomic rings, the atomic rings can include a plurality of double bonds.

A photoluminescent nanostructure can be a class of nanostructures that can exhibit photoluminescence. In some embodiments, photoluminescent nanostructures can exhibit fluorescence. In some instances, photoluminescent nanostructures can exhibit phosphorescence. Examples of photoluminescent nanostructures suitable for use can include, but are not limited to, single-walled carbon nanotubes (SWCNTs), double-walled carbon nanotubes (DWCNTs), multi-walled carbon nanotubes (MWCNTs), semi-conductor quantum dots, semi-conductor nanowires, or graphene, among others. In some embodiments, the photoluminescent nanostructures can be a semi-conductive single-walled carbon nanotube.

Selective binding can be sufficiently specific that it can be used to distinguish the analyte from other chemical species. The polymer can be considered random because, in the absence of the complex, the polymer has little or no affinity for the analyte.

In some embodiments, the polymer can be a polysaccharide. The polysaccharide can include peptidoglycans, lipopolysaccharides, amylase, chitin, chitosan, glycogen, cellulose, dextran, functionalized dextran, phenoxy functionalized dextran or boronic acid functionalized phenoxy dextran.

In some embodiments, the polymer can be a polynucleotide. The polynucleotide can be DNA or RNA. The polynucleotide can be single stranded or double stranded. The polynucleotide can be single stranded in one section and double stranded in another section. RNA can include mRNA, siRNA or shRNA.

The polynucleotide can form a structure. Exemplary nucleic acid structures can include an A-form double helix, a B-form double helix, a Z-form double helix, a hairpin, a loop or a stem loop.

The polynucleotide can contain ribonucleotides or deoxyribonucleotides. The polynucleotide can have less than 100,000, less than 50,000, less than 25,000, less than 10,000, less than 5,000, less than 1,000, less than 500, less than 250, less than 100, less than 75, less than 50, less than 30, less than 25, less than 20, 15, 12, 10, 8, 6 or 4 nucleotides.

The polynucleotide can have a random sequence. The polynucleotide can have an ordered sequence. The ordered sequence can be a predetermined sequence. For example, an ordered sequence can be the sequence of a gene. The ordered sequence can be a repeating sequence. The repeat sequence can include less than 500, less than 400, less than 300, less than 200, less than 100, less than 50, less than 30, less than 25, less than 20, 15, 14, 13, 12, 11, 10, 9, 8, 7, 6, 5, 4, 3 or 2 nucleotides. The polynucleotide can be poly(AT), poly (GT), poly(CT), poly(AG), poly(CG), or poly(AC). The polynucleotide can have a content. The content can be a percentage of a unique nucleotide present in the sequence. The percentage can be 100% of a unique nucleotide, including poly(A), poly(C), poly(G), poly(T) or poly(U).

In some embodiments, the polymer can be a polylipid. The polylipid can include a phospholipid, a palmitoyl phospholipid or 1,2-dipalmitoyl-sn-glycero-3-phosphoethanolamine-N-(lauroyl) (PL-DOD).

In other embodiments, the polymer can be polyvinylpyrrolidone, a poly(ethylene oxide), a poly(ethylene oxide)-poly (propylene oxide)-poly (ethylene oxide) block co-polymer, poly (N-isopropyl acrylamide), polyethyleneimine, polyacrylamide, polyvinyl alcohol or collagen.

In some embodiments, the polymer can be a polypeptide. In some embodiments, the number of amino acids comprising the polypeptide can fall within a specific range. For example, the polypeptide can include between 5 and about 50 amino acid residues, or between 5 and about 30 amino acid residues. In other embodiments, the polypeptide can fall within a specific molar mass range. For example, the polypeptide can have a molecular weight of between 400 g/mol and about 10,000 g/mol, or between 400 g/mol and about 6,000 g/mol. The polypeptide can be a protein, having greater than about 50 amino acid residues. The polypeptide can be a fragment of a protein. In some embodiments, the polypeptide can be expressed in a disease state. In other embodiments, the polypeptide can be modified. In some circumstances, the polypeptide can be modified by attaching functional groups. In other circumstances, the polypeptide can be ubiquinated, biotinylated, glycosylated, PEGylated or SUMOylated. The polypeptide can be a biomarker, an enzyme, a receptor, a ligand, a peptide hormone, a neuropeptide, a vasoactive intestinal peptide, a chaperone or an antibody.

The polypeptide can, in some instances, include a peptide sequence observed in the venom of an animal or a derivative thereof. In some cases, the polymer can include a polypeptide sequence (or derivative thereof) observed in the venom of a member of the Insecta class, the Hymenoptera order, or the Vespidae or Apidae families. In some embodiments, the polypeptide can be a member the Mastoparan or Bombolitin (including Bombolitin II, Bombolitin III) families of polypeptides, or derivatives of those polypeptides. The polypeptide can include a mastoparan, mastoparan 7 or mastoparan X.

In the complex, the polymer can be adsorbed on the photoluminescent nanostructure. While individual polymers can be adsorbed or pinned to one point on the nanotube, it should be understood that the polymer can assume any suitable shape or configuration on the nanotube.

While the polymer can be free from selective binding to the analyte, the composition can include a selective binding site associated with the complex. The selective binding site can be associated with the polymer. The selective binding site can also be associated with the nanostructure. Additionally, the selective binding site can be associated with both the polymer and the nanostructure.

Changing the ratio of the amount of polymer to the amount of photoluminescent nanostructure can result in different compositions, which can interact differently with an analyte. Changing the ratio of a first type of monomer in the polymer to a second type of monomer in the polymer also can result in different compositions. For example, the ratio of the amount of boronic acid functionalized phenoxy dextran to the amount of phenoxy dextran in the polymer can be altered to change the polymer. A different polymer can result in a different selective binding site. A different polymer can alter a property of the composition. The property can be an emission.

The diameter of a photoluminescent nanostructure can be different from the diameter of another photoluminescent nanostructure. The diameter of the photoluminescent nanostructure can affect the adsorption of the polymer on the photoluminescent nanostructure. The diameter of the photoluminescent nanostructure can affect the selective binding site. The diameter of the photoluminescent nanostructure can affect a property of the composition. The property of the composition can be an emission.

Carbon nanotubes can be classified by the chiral vector (n,m) that can characterize the orientation of the carbon hexagons in a corresponding graphene sheet. The chiral vector of a photoluminescent nanostructure can be different from the diameter of another photoluminescent nanostructure. The chiral vector of the photoluminescent nanostructure can affect the adsorption of the polymer on the photoluminescent nanostructure. The chiral vector of the photoluminescent nanostructure can affect the selective binding site. The chiral vector of the photoluminescent nanostructure can affect a property of the composition. The property of the composition can be an emission.

In some embodiments, the analyte can be a small molecule, protein, biomolecule, explosive, drug, biologic, or a metabolite thereof. For example, the analyte can be monosaccharide, a polysaccharide, an amino acid, a nucleotide, an oligonucleotide, a lipid, a polylipid or a steroid. More specifically, the analyte can be riboflavin or nitric oxide. In some embodiments, the analyte can be 17-α-estradiol, 2,4-dinitrophenol, acetylcholine chloride, α-tocopherol, adenosine, adenosine-5'-triphosphate, cyclic adenosine monophosphate, creatinine, cytidine, D-aspartic acid, D-fructose, D-galactose, D-glucose, D-mannose, dopamine, glycine, guanosine, histamine, L-ascorbic acid, L-citrulline, L-histidine, L-thyroxine, melatonin, NADH, quinine, salicylic acid, serotonin, sodium azide, sodium pyruvate, sucrose, thymidine, tryptophan, tyramin or urea. In some embodiments, the analyte can be a DNA sequence, a RNA sequence or a siRNA sequence. In some embodiments, the analyte can be albumin, Immunoglobulin G (IgG), fibrinogen, α1-antitrypsin, transferrin, haptoglobin, α2-macroglobulin, Immunoglobulin A (IgA), Immunoglobulin M (IgM), α1-acidglycoprotein, and apoliporprotein A-I, insulin, human chorionic gonadotropin (hCG), and C-reactive protein (CRP), or any other protein present in the human blood.

In other embodiments, the analyte can be a peptide or a protein. In some embodiments, the number of amino acids comprising the polypeptide can fall within a specific range. For example, the polypeptide can include between 5 and about 50 amino acid residues, or between 5 and about 30 amino acid residues. In other embodiments, the polypeptide can fall within a specific molar mass range. For example, the polypeptide can have a molecular weight of between 400 g/mol and about 10,000 g/mol, or between 400 g/mol and about 6,000 g/mol. The polypeptide can be a protein, having greater than about 50 amino acid residues. The polypeptide can be a fragment of a protein. In some embodiments, the polypeptide can be expressed in a disease state. In other embodiments, the polypeptide can be modified. In some circumstances, the polypeptide can be modified by attaching functional groups. In other circumstances, the polypeptide can be ubiquinated, biotinylated, glycosylated, PEGylated or SUMOylated. The polypeptide can be a biomarker, an enzyme, a receptor, a ligand, a peptide hormone, a neuropeptide, a vasoactive intestinal peptide, a chaperone or an antibody.

The composition can be used for analyzing a sample for an analyte. The method for analyzing a sample for an analyte can include providing a composition which can include a complex and a selective binding site associated with the complex. The complex can include a photoluminescent nanostructure and a polymer free from selective binding to an analyte. The polymer can be adsorbed on the photoluminescent nanostructure. The method can include exposing the composition to a sample. The method can also include monitoring a property of the composition. The method can include determining the presence of an analyte in the sample based on the property.

In some embodiments, the sample can include a gas, a liquid or a solid. In other embodiments, the sample can be a biological fluid.

In some embodiments, exposing the composition to a sample can include inserting the composition into an animal. In particular, the animal can be a human. In other embodiments, exposing the composition to a sample can include inserting the composition into a plant or fungus. Inserting can include embedding the composition within the organism, embedding the composition within a cell of the organism, puncturing the organism with the composition or inserting the composition in a natural opening of the organism, among others.

Exposing the composition to a sample can also include incubating the composition with a microorganism or a virus. Exposing the composition to a sample can include incubating the composition with a cell line. In still other embodiments, exposing the composition to a sample can include incubating the composition with an in vitro model system.

In some embodiments, the property can be an emission. More specifically, the emission can be photoluminescence. The photoluminescence can be fluorescence or phosphorescence. In some embodiments, the property can be emission intensity. In other embodiments, the property can be an emission wavelength.

Monitoring the property can include observing the property of the composition alone. Monitoring the property can include monitoring the property after the composition has been exposed to the sample. Monitoring the property can include monitoring the property after the composition has been exposed to the analyte. Monitoring the property can include monitoring the property after the composition has been exposed to known concentrations of the analyte.

Monitoring a property of the composition can include observing the property through a microscope. Monitoring a property of the composition can include measuring the property using a microscope. The microscope can be a near infrared microscope. The microscope can be a dual-channel microscope. Monitoring a property of the composition can include monitoring the property using still photography or movies. The photography or movies can be on film media or digital form.

Determining the presence of an analyte can include determining the absence of the analyte. In some embodiments, determining the presence of an analyte can include determining the concentration of the analyte, determining the purity of the analyte or determining the quantity of the analyte. In some embodiments, relatively low concentrations or quantities of an analyte can be determined. The ability to determine low concentrations of an analyte may be useful, for example, in detecting trace pollutants or trace amounts of toxins within a subject. In some embodiments, analyte concentrations of less than about 100 micromolar, less than about 10 micromolar, less than about 1 micromolar, less than about 100 nanomolar, less than about 10 nanomolar, or less than about 1 nanomolar can be determined. The quantity of the analyte that can be determined can be less than 1 mole, less than 1 millimole, less than 1 micromole, less than 1 nanomole, less than 1 picomole, less than 1 femtomole, less than 1 attomole or less than 1 zeptomole. In some cases, a single molecule of an analyte can be determined. The purity of the analyte can be greater than 25% pure, greater than 50%, greater than 75% pure, greater than 80%, greater than 85% pure, greater than 90% pure, greater than 95% pure, greater than 99% pure or greater than 99.9% pure.

In some embodiments, the method for analyzing a sample for an analyte further includes obtaining a sample. More specifically, the method can include obtaining a sample from an animal, a microorganism, virus, plant, fungus or cell line. The animal can be a human. A sample can be obtained by drawing blood or other bodily fluids, biopsy, scraping, excision, lysis or plucking, among others.

In some embodiments, the method for analyzing a sample for an analyte includes coating a glass slide with the composition. The glass slide can be treated with a silane prior to coating with the composition. The silane can enhance adhesion of the composition to the glass slide. The silane can be 3-aminopropyltriethoxysilane (APTES).

In one aspect, a system can include a composition which can include a complex and a selective binding site associated with the complex. The complex can include a photoluminescent nanostructure and a polymer, the polymer being free from selective binding to an analyte in the absence of being adsorbed on the nanostructure. The polymer can be adsorbed on the photoluminescent nanostructure. The system can include an electromagnetic radiation source having an excitation wavelength directed at the composition. The system can include a detector configured to receive an emission wavelength from the composition.

The electromagnetic radiation source can be a light source. The electromagnetic radiation source can be a laser. The electromagnetic radiation can include radio waves, microwaves, terahertz radiation, infrared radiation, visible light, ultraviolet radiation, X-rays and gamma rays. The electromagnetic radiation can have an excitation wavelength in the visible spectrum, near infrared spectrum or infrared spectrum.

The detector can include a near infrared detector. The detector can include a near infrared fluorometer. The detector can be mounted on a microscope.

One advantage of the composition can be that for target protein or protein therapeutic detection the need to tag or label the target therapeutic to enable detection can be eliminated. One advantage of the composition can be that composition will bind directly to the analyte. Another advantage of the composition can be that the composition will work for detecting small molecules, antibodies, antibody fragments, proteins, and peptide fragments. An additional advantage of the composition can be that the composition can detect molecules for which there is no known binding partner. An advantage of the composition can be that, due to the non-photobleaching nature of SWCNT, the composition can allow for continuous detection of the target analyte.

The composition can also be used for separation techniques. The method can include providing a composition. The composition can include a complex and a selective binding site associated with the complex. The complex can include a photoluminescent nanostructure and a polymer, the polymer being free from selective binding to an analyte in the absence of being adsorbed on the nanostructure. The polymer can be adsorbed on the photoluminescent nanostructure. The method can include exposing the composition to a mixture containing the analyte. The method can include separating the composition from the mixture. Separating the composition from the mixture can remove the analyte from the mixture.

An advantage of the composition can be that the composition may be able separate molecules for which there is no known binding partner. Another advantage of the compositions may be that the composition will work for the separation of analytes, including small molecules, antibodies, antibody fragments, proteins, and peptide fragments, among others. An advantage of the composition can be that one complex may be capable of binding multiple target molecules. Binding of multiple target molecules may allow for enhanced separation. An advantage of the composition can be that the separation process can be scalable.

In some embodiments, the composition can further include an amount of the analyte. In some embodiments, the analyte is a therapeutic. The composition can be used to deliver the therapeutic. The method can include providing a composition that includes an amount of the therapeutic. The method can include administering the composition to an animal. Administering the composition can include administering the composition by topical, enteral, parenteral, transdermal, transmucosal, inhalational, intracisternal, epidural, intravaginal, intravenous, intramuscular, subcutaneous, intradermal or intravitreal administration. In some embodiments, the method can further include monitoring a property of the composition. The method can also include determining the presence of the therapeutic in the composition based on a property. The property can be an emission, an emission intensity or an emission wavelength. Determining the presence of the therapeutic can include determining the presence, the absence or the concentration of the therapeutic.

One advantage of the composition, which can include a therapeutic, can be the possibility of a multivalent interaction between the polymer—SWCNT and the drug. The possibility of a multivalent interaction may be due to multiple binding sites along the length of the nanotube. The possibility can also mean the composition drug efficacy would be higher. Another advantage of the composition can be a concentrated drug release from the composition. A concentrated drug release may be due to one nanotube potentially containing many therapeutic molecules. An advantage of the composition can be resistance of the therapeutic to enzymatic degradation in the blood. This can be because the therapeutic can be shielded or protected within the composition. Still another advantage can be the possibility of tracing the pharmacokinetic pathways. Tracing the pharmacokinetic pathways of the drug may elucidate in vivo reaction pathways and enhance further drug design. Tracing may be possible because the SWCNT NIR fluorescence is tissue transparent.

The composition can also be used in catalysis reactions. The method can include providing the composition, including an amount of the analyte. The method can include exposing the composition to a catalyst. The method can further include monitoring a property of the composition. The method can also include determining modification of the analyte based on the property.

An advantage of the composition can be the possibility to do site-specific functionalization of target proteins, antibodies, antibody fragments and peptides. Another advantage of the composition can be the possibility to do site-specific small molecule reactions. The small molecule reactions can be similar to those done in nature by enzymatic reactions.

A method for making the composition can include suspending the photoluminescent nanostructure in a surfactant. The surfactant can contain the polymer. The surfactant can be anionic. The surfactant can be sodium cholate. The suspension can be agitated. The agitation can evenly distribute the nanostructures. The agitation can prevent the nanostructures from aggregating. The agitation can include sonication. Aggregates can be removed from the suspension. Aggregates can be removed by discarding a pellet following centrifugation. The polymer can be added to the surfactant after aggregates are removed. The method can include removing the surfactant. Dialysis can be used to remove the surfactant. Removal of the surfactant can allow for the polymer to self-assemble on the nanostructure.

A method for making the composition can include suspending the photoluminescent nanostructure and the polymer in a salt solution. The salt solution can be sodium chloride. The method can also include suspending the photoluminescent nanostructure and the polymer in an organic compound solution. The organic compound solution can be a buffer. The buffer can have an effective pH range between 7.0 and 9.5. The buffer can be tris(hydroxymethyl)aminomethane. The suspensions can be agitated. The agitation can evenly distribute the photoluminescent nanostructure. The agitation can prevent the nanostructures from aggregating. The agitation can include sonication. Aggregates can be removed from the suspension. Aggregates can be removed by discarding a pellet following centrifugation.

A method for determining analytes recognized by the selective binding site in the composition can include exposing different compositions to an analyte. Two or more compositions can be different from one another because the compositions contain different polymers from one another. Two or more compositions can be different from one another because the compositions contain the same polymer of different lengths. Two or more compositions can also be different from one another because the compositions contain polymers that are comprised monomers in different ratios. Two or more compositions can be different from one another because the compositions contain the same monomers but in one polymer the monomers are modified. Two or more compositions can be different from one another because the compositions contain different photoluminescent nanostructures. Two or more compositions can be different from one another because the compositions contain photoluminescent nanostructures of different diameters. Two or more compositions can be different from one another because the compositions contain photoluminescent nanostructures with different chiral vectors.

A method for determining analytes recognized by the selective binding site in the composition can include exposing different analytes to a composition.

A method for determining analytes recognized by the selective binding site in the composition can include monitoring a property of the composition. The property can be an emission, emission intensity or emission wavelength. Monitoring the property can include observing the property of the composition alone. Monitoring the property can include monitoring the property after the composition has been exposed to a sample. Monitoring the property can include monitoring the property after the composition has been exposed to the analyte. Monitoring the property can include monitoring the property after the composition has been exposed to known concentrations of the analyte. Monitoring the property of the composition can provide a data set associated with an analyte.

The data set can include the emission of the photoluminescent nanostructure. The data set can include a change in emission intensity observed between a first emission intensity in the presence of the analyte and a second emission intensity in the absence of the analyte. The data set can include a change in emission wavelength shift observed between an emission wavelength in the presence of the analyte and an emission wavelength in the absence of the analyte. The data set can include data obtained from applying algorithms to the data obtained by monitoring the property. The data set can include binding constants. The data set can be used to determine if the composition can selectively bind to the analyte. The data set can be used to determine if the composition binding to the analyte can be detected by monitoring a property of the composition.

A method for determining analytes recognized by the selective binding site in the composition can be a high-throughput screening assay (FIG. 17). A method for analyzing samples in a high-throughput system can include providing an array including a plurality of compositions, exposing each composition to at least one sample, monitoring a property of each composition, and determining a presence of an analyte in the sample based on the property. Each composition in the array can include a complex, where the complex can include a nanostructure, and a polymer. The polymer can be adsorbed on the nanostructure and the polymer can be free from selective binding to an analyte in the absence of being adsorbed on the nanostructure. A selective binding site can be associated with the complex.

A well plate array can be used for exposing the composition to an analyte. The composition in different individual wells can include different individual polymers. The composition in different individual wells can include the same polymer. In some embodiments, the composition in different individual wells can be exposed to different individual analytes. In other embodiments, the composition in different individual wells can be exposed to the same analyte.

It can be determined using the methods above that a specific composition can selectively bind to a specific analyte. The specific composition can be used for detecting the analyte in a sample. The specific composition can detect the specific analyte in a sample containing other analytes. The specific composition can be mixed with other compositions. The other compositions can have selective binding for other analytes. The specific composition mixed with other compositions can detect the specific analyte in a sample. The specific composition mixed with other compositions can detect the specific analyte in a sample containing other analytes. In addition, more than one specific composition mixed with other compositions can detect the specific analytes corresponding to the specific analytes in a sample containing other analytes.

For example, composition A can detect analyte A; composition B can detect analyte B; and composition C can detect analyte C. It is possible that composition A can detect analyte A in a mixture including analyte A, analyte B, and analyte C. Furthermore, it is possible that composition A, in a mixture including composition A, composition B and composition C, can detect analyte A. Additionally, it is possible that composition A, in a mixture including composition A, composition B and composition C, can detect analyte A from a sample including analyte A, analyte B and analyte C.

Disclosed herein is the CoPhMoRe screen adapted to macromolecules, developing a series of validation assays to unequivocally assign fluorescence modulation to CoPhMoRe phase binding and recognition. The first library was constructed and a screening of CoPhMoRe phases was conducted against 14 protein analytes, selected for their abundance and clinical significance in human whole blood. See, Rifai, N., Gillette, M. A. & Carr, S. A. Protein biomarker discovery and validation: the long and uncertain path to clinical utility. *Nat Biotech* 24, 971-983 (2006), Anderson, L. & Hunter, C. L. Quantitative Mass Spectrometric Multiple Reaction Monitoring Assays for Major Plasma Proteins. *Molecular & Cellular Proteomics* 5, 573-588, doi: 10.1074/mcp.M500331-MCP200 (2006), and Hanash, S. M., Pitteri, S. J. & Faca, V. M. Mining the plasma proteome for cancer biomarkers. *Nature* 452, 571-579 (2008), each of which is incorporated by reference in its entirety. The human plasma proteome consists of hundreds of proteins whose concentrations span over more than 10 orders of magnitude (see, Anderson, N. L. & Anderson, N. G. The Human Plasma Proteome: History, Character, and Diagnostic Prospects. *Molecular & Cellular Proteomics* 1, 845-867, doi:10.1074/mcp.R200007-MCP200 (2002), which is incorporated by reference in its entirety), from which albumin, Immunoglobulin G (IgG), fibrinogen, α1-antitrypsin, transferrin, haptoglobin, α2-macroglobulin, Immunoglobulin A (IgA), Immunoglobulin M (IgM), α1-acid-glycoprotein, and apoliporprotein A-I were selected, owing to their high abundancy, and insulin, human chorionic gonadotropin (hCG), and C-reactive protein (CRP), owing to their clinical importance. A screen of 20 distinct SWCNT corona phases against the proteins panel shows surprising recognition of fibrinogen to the exclusion of the other 13 using a dipalmitoyl-phosphatidyletanolamine (DPPE)-PEG (5 kDa)—SWCNT CoPhMoRe phase. This recognition is not related to isoelectric point, aggregation, molecular weight, protein hydrophobicity or any other non-selective mechanism. Further, the fibrinogen recognition still occurs in competitive binding assays, starting from testing in the presence of albumin, which is a common agent for surface passivation and blocking of nonspecific binding (see, Zheng, G., Patolsky, F., Cui, Y., Wang, W. U. & Lieber, C. M. Multiplexed electrical detection of cancer markers with nanowire sensor arrays. *Nat Biotech* 23, 1294-1301 (2005), Jeyachandran, Y. L., Mielczarski, E., Rai, B. & Mielczarski, J. A. Quantitative and Qualitative Evaluation of Adsorption/Desorption of Bovine Serum Albumin on Hydrophilic and Hydrophobic Surfaces. *Langmuir* 25, 11614-11620 (2009), and Sweryda-Krawiec, B., Devaraj, H., Jacob, G. & Hickman, J. J. A New Interpretation of Serum Albumin Surface Passivation. *Langmuir* 20, 2054-2056 (2004), each of which is incorporated by reference in its entirety), followed by a successful demonstration of fibrinogen detection in serum environment.

For example, a combination of the SWCNT corona phase formed by the specific phospholipid-PEG along with the unique three dimensional conformation of the fibrinogen protein, a high aspect ratio elongated molecule, can be responsible for the molecular recognition. This is supported by high resolution atomic force microscopy (AFM) images, which manifest the facile recognition of fibrinogen on the CoPhMoRe phase by physical binding and the alignment of the fibrinogen molecules with the nanotube axis, and by quartz crystal microbalance with dissipation (QCM-D) measurements, which show fibrinogen monolayer adsorption on top of the SWCNT layer such that the protein molecules lay with their long axis parallel to the nanotube surface layer. In addition, kinetic measurements confirm a three step molecular adsorption, consistent with the three nodule structure of the fibrinogen. See, Yermolenko, I. S., Lishko, V. K., Ugarova, T. P. & Magonov, S. N. High-Resolution Visualization of Fibrinogen Molecules and Fibrin Fibers with Atomic Force Microscopy. *Biomacromolecules* 12, 370-379, doi: 10.1021/bm101122g (2010), and Scheraga, H. A. The thrombing fibrinogen interaction. *Biophysical Chemistry* 112, 117-130 (2004), each of which is incorporated by reference in its entirety. Moreover, photo-absorption measurements and cryo-transmission electron microscope (TEM) imaging rule out aggregation or precipitation of the SWCNT, which is supported by a demonstration of the sensor functionality while encapsulated within a thin hydrogel bed or when adsorbed onto a surface. The functionality at the single sensor level of individual surface-immobilized SWCNT, along with the optical readout in real-time, enables a detection with both spatial and temporal resolution. These results open the door to protein CoPhMoRe based recognition for proteomic and medical research, while expanding the applicability of the CoPhMoRe concept to bio-macromolecules for the first time.

Herein corona phase molecular recognition of a protein is demonstrated for the first time. Two non-limiting examples are presented: fibrinogen and insulin. By screening the response of the fluorescent emission of a library of DNA, RNA, and phospholipid-PEG suspended SWCNT upon the interaction with a library of human proteins, the DPPE-PEG (5000)-SWCNT complex acts as a selective sensor for fibrinogen. In response to fibrinogen binding, SWCNT fluorescence decreases by more than 80% at saturation. Sequential binding of the three fibrinogen nodules is suggested by selective fluorescence quenching by isolated sub-domains and validated by the quenching kinetics. The fibrinogen recognition also occurs in serum environment, at the clinically relevant fibrinogen concentrations in the human blood.

Insulin recognition was demonstrated with $C_{16}$-PEG (2000 kDa)-Ceramide, manifesting 62% fluorescent intensity decrease of the (10,2) nanotube chirality for 20 µg/ml insulin concentration. The insulin protein has no prior affinity towards the $C_{16}$-PEG(2000 kDa)-Ceramide molecules, verified by isothermal titration calorimetry, and the interaction occurs only upon their adsorption onto the single-walled carbon nanotube scaffolds. Testing a panel of proteins originated from the human blood, as well as short fragments of the insulin peptide chains of 7 amino-acids, rules out nonselective recognition mechanisms such as molecular weight, isoelectric point, and hydrophobicity based detection. Longer fragments of the insulin chains were able to be detected, however, with lower affinity compared to the intact protein, suggesting that the recognition is of insulin in its native form. Finally, the insulin recognition and concentration quantification was demonstrated both in buffer and in a complex and competitive environment such as serum.

EXAMPLES

I. Fibrinogen Recognition

Although DPPE-PEG(5000) had one of the highest relative SWCNT surface coverages compared to various PEGylated lipids, DNA, or RNA wrappings, no correlation between surface coverage and recognition was found. Moreover, the selective response is not explained by elementary protein parameters such as molecular weight, isoelectric point, or relative surface hydrophobicity, whereas CD spectroscopy rules out protein denaturation. Finally, the invariant height and width of the absorption peaks, and the individually suspended SWCNT imaged by cryo-TEM, rule out nanotube aggregation or precipitation as the fluorescent quenching mechanism, supported by the successful demonstration of the sensor response when immobilized within a hydrogel or on a glass surface. Hence, the specific corona phase formed by the DPPE-PEG(5000) enables recognition of the unique tri-nodule fibrinogen protein.

A detailed analysis of the interaction reveals a mechanism of sequential binding of the three fibrinogen nodules, starting with one of the outer D-regions binding to the SWCNT, followed by the other D- and E-regions, and the alignment of the protein along the nanotube, resulting in the complete binding of the three fibrinogen nodes to the SWCNT surface and a substantial fluorescent emission quenching. This reaction mechanism is supported by fitting kinetic experimental results, and high resolution atomic force microscopy. Moreover, QCM-D measurements show the monolayer adsorption of fibrinogen onto surface-deposited DPPE-PEG(5000)-SWCNT, forming a thin layer whose thickness indicates that the protein molecules lay horizontally flat on the underlying nanotubes.

The DPPE-PEG(5000)-SWCNT sensor responses to fibrinogen in the presence of albumin, which is the most abundant protein in blood and usually used as the gold standard in assessing non-specific protein adsorption, thus paving the way to utilizing of the sensor in a controlled environment with additional components. Furthermore, the sensor can detect fibrinogen in serum environment over a concentration range covering the clinically relevant concentrations of fibrinogen in human blood (1.75-4.3 g $L^{-1}$). Finally, the ability of the sensor to detect the fibrinogen protein when immobilized within agarose gel opens the possibility of use in vivo with an implantable biocompatible hydrogel. See, Iverson, N. M. et al. In vivo biosensing via tissue-localizable near-infrared-fluorescent single-walled carbon nanotubes. *Nat Nano* 8, 873-880, doi:10.1038/nnano.2013.222 (2013), which is incorporated by reference in its entirety.

In summary, a molecular recognition motif can be achieved based on the corona phase of fluorescent nanoparticles, for the detection and quantification of macromolecules. For example, fibrinogen, an important protein biomarker that is an essential factor in the blood coagulation cascade and the principal element of a thrombus. This work motivates the search for novel CoPhMoRe phases for protein recognition. This methodology can generate new synthetic non-biological antibodies and provide an alternative for conventional antibodies, which suffer from major limitations including the need of a living organism for initial production, long development times, high production costs and challenging reproducibility, poor stability due to hydrolysis in ambient temperature and moderate acidic conditions resulting in limited shelf life, and sensitivity to degradation while circulating in vivo. In contrast, this single walled carbon nanotube template recognition overcomes these shortcomings by offering a stable and reproducible construct that can push forward discovery research in the field allowing multiplexed high throughput synthesis and library screenings.

The following examples are representative.

SWCNT Suspension Characterization.

Single walled carbon nanotubes (SWCNT), produced by the HiPCO catalysis, were suspended with ssDNA and ssRNA by direct sonication (see, Landry, M. P. et al. Comparative Dynamics and Sequence Dependence of DNA and RNA Binding to Single Walled Carbon Nanotubes. *The Journal of Physical Chemistry C*, doi:10.1021/jp511448e (2015), which is incorporated by reference in its entirety), or with phospholipid-PEG polymers (listed in FIG. 1A), by exchanging sodium-cholate (SC) wrapping using dialysis. Successful suspensions were evident from the distinct absorption peaks (FIG. 6A) and the bright fluorescent emission under 785 nm laser excitation (dashed black curve in FIG. 1B and FIG. 6B). In addition, when the excess phospholipid-PEG molecules were removed from the solution by filtration or dialysis, the suspension retained its stability, manifested by the absorption and fluorescent spectra, as opposed to the initial SC-SWCNT suspension, which underwent massive aggregation and lost both its absorption and fluorescence emission (FIGS. 7A-7D). The DPPE-PEG (5000)—SWCNT suspension remains stable, whereas the SC sample aggregates and loses its colloidal stability as evident from the loss of both the absorption and fluorescence peaks.

The fluorescent emission peaks correspond to the radiative decay of excitons, which are influenced by the local dielectric environment of the SWCNT surface. See, O'Connell, M. J. et al. Band Gap Fluorescence from Individual Single-Walled Carbon Nanotubes. *Science* 297, 593-596, doi:10.1126/science.1072631 (2002), Wang, F., Dukovic, G., Brus, L. E. & Heinz, T. F. The Optical Resonances in Carbon Nanotubes Arise from Excitons. *Science* 308, 838-841 (2005), and Choi, J. H. & Strano, M. S. Solvatochromism in single-walled carbon nanotubes. *Applied Physics Letters* 90, 223114-223114-223113, doi:10.1063/1.2745228 (2007), each of which is incorporated by reference in its entirety. Fluctuating electric fields resulting from random orientations of dipole moments in the close proximity of the SWCNT can induce a dipole moment on the highly polarizable SWCNT. Although SWCNT have no net dipole moment, the electric fields can cause a shift in their electronic transitions (solvent Stark effect). The semi-empirical functional form describing this shift is given by:

$$(E_{ii})^2 \Delta E_{ii} = -Lk\left[\frac{2(\varepsilon-1)}{2\varepsilon+1} - \frac{2(n^2-1)}{2n^2+1}\right]\frac{1}{R^4} = \frac{C}{R^4} \quad (1)$$

where $E_{ii}$ is the optical transition energy, $\Delta E_{ii}$ is the difference between the optical transition energy in the dielectric environment and the optical transition energy of pristine SWCNT in air, L is a fluctuation factor, k is a scaling constant of the SWCNT polarizability, $\varepsilon$ is the static dielectric constant, n is the refractive index, and R is the nanotube radius. The constant C gathers all the parameters that are constant for a specific chirality.

The experimental optical transitions of the various SWCNT suspensions, $E_{11}$, were calculated by deconvoluting the fluorescent emission spectra to the different chiralities in the HiPCO sample (see, Tvrdy, K. et al. A Kinetic Model for the Deterministic Prediction of Gel-Based Single-Chirality Single-Walled Carbon Nanotube Separation. *ACS Nano* 7, 1779-1789, doi:10.1021/nn305939k (2013), which is incorporated by reference in its entirety) (FIG. 8), and the optical transitions in air were calculated according to:

$$E_{11}^{air} = \frac{hc}{A_1 + A_2 d} + A_3 \frac{\cos\theta}{d^2} \quad (2)$$

where h is Planck's constant, c is the speed of light, d is the SWCNT diameter, θ is the chiral angle corresponding to the SWCNT chirality (n, m), $A_1$=61.1 nm, and $A_2$=1113.6. By noting mod((n−m), 3)=j, $A_3$=−0.077 eV nm$^2$ for j=1, and $A_3$=0.032 eV nm$^2$ for j=2.

Figure 1A:
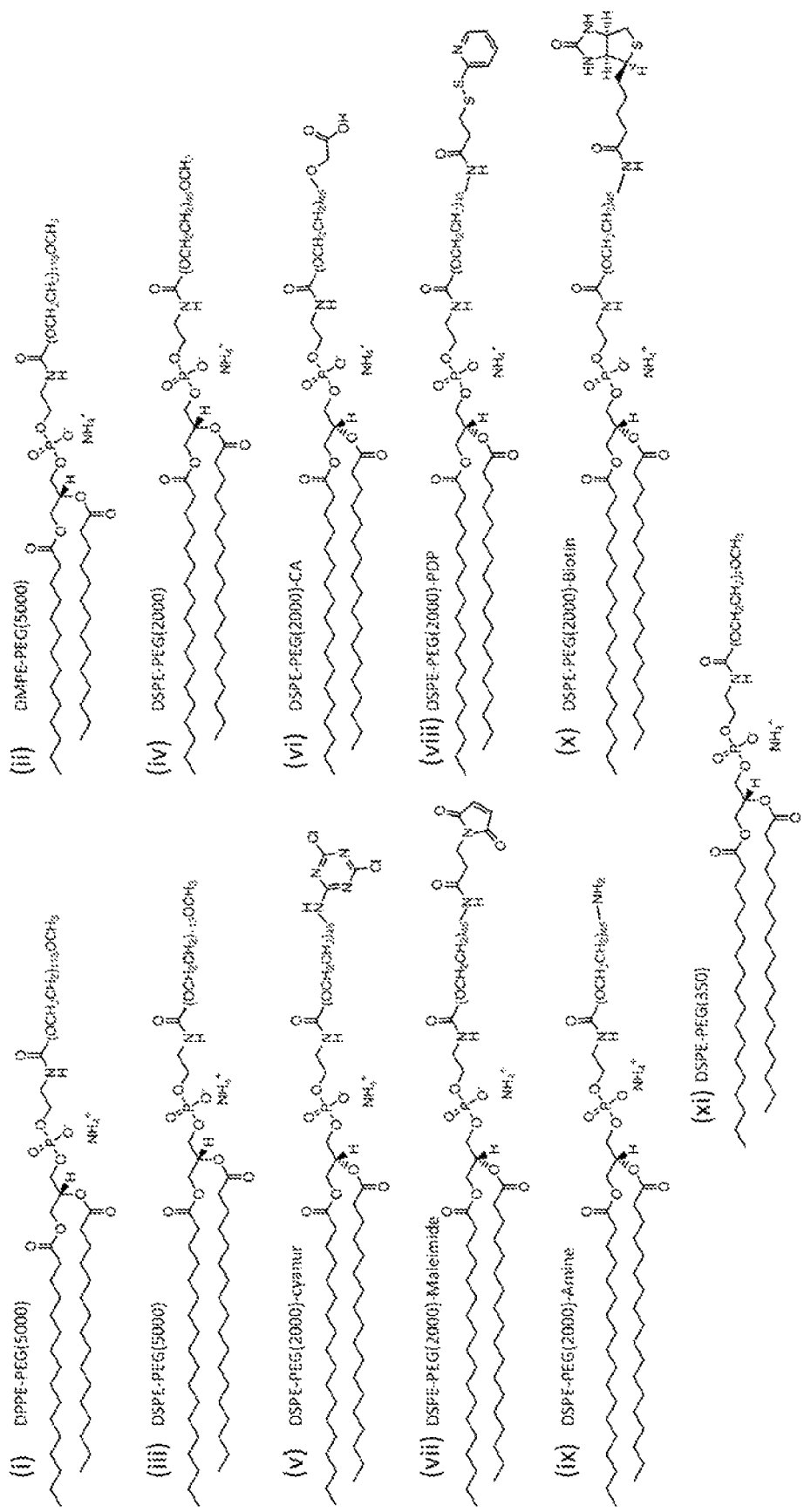
FIGS. 1A-1C show SWCNT suspension library.
Figure 1B:
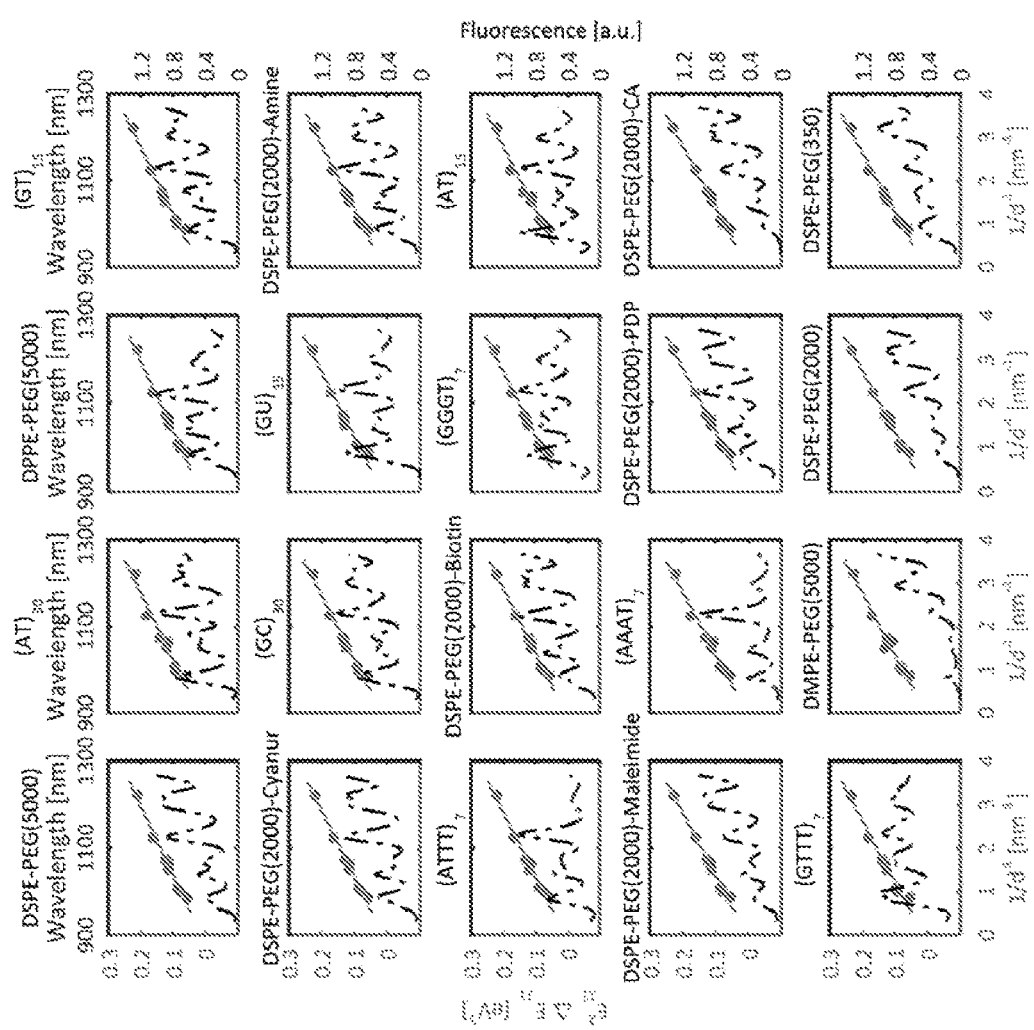

The solvatochromic shift, $(E_{11})^2 \Delta E_{11}$, is plotted against the SWCNT diameter to the power of negative 4 ($d^{-4}$) for the various chiralities in each suspension in FIG. 1B, and the data is fitted with a linear curve (blue dots, and solid red curve, respectively). The slopes of the fit curves and the corresponding R-squared parameters are listed in Table 1. These slopes can be utilized to estimate the effective dielectric constant, $\varepsilon_{eff}$, in the vicinity of the SWCNT, by comparing them to the slope of a reference system (see, Mu, B. et al. A Structure-Function Relationship for the Optical Modulation of Phenyl Boronic Acid-Grafted, Polyethylene Glycol-Wrapped Single-Walled Carbon Nanotubes. *Journal of the American Chemical Society* 134, 17620-17627, doi: 10.1021/ja307085h (2012), and Hilmer, A. J., Tvrdy, K., Zhang, J. & Strano, M. S. Charge Transfer Structure-Reactivity Dependence of Fullerene-Single-Walled Carbon Nanotube Heterojunctions. *Journal of the American Chemical Society* 135, 11901-11910, doi:10.1021/ja404636b (2013), each of which is incorporated by reference in its entirety) of SWCNT suspended in n-methyl-2-pyrrolydone (NMP):

$$\frac{C}{C_{NMP}} = \frac{\frac{\varepsilon_{eff}-1}{2\varepsilon_{eff}+1} - \frac{n^2-1}{2n^2+1}}{\frac{\varepsilon_{NMP}-1}{2\varepsilon_{NMP}+1} - \frac{n_{NMP}^2-1}{2n_{NMP}^2+1}} \quad (3)$$

where $C_{NMP}$=0.060 eV$^3$ nm$^4$, $\varepsilon_{NMP}$=32.2, and $n_{NMP}$=1.47 (Table 1).

TABLE 1

Fit parameters for the solvatochromism shift model.
The slope, R-squared, effective dielectric constant
($\varepsilon_{eff}$), and the relative surface coverage ($\alpha$).

| Wrapping | Slope | $R^2$ | $\varepsilon_{eff}$ | $\alpha$ |
|---|---|---|---|---|
| (GT)$_{15}$ (SEQ ID NO: 1) | 0.06600 | 0.972 | 16.316 | 0.854 |
| (GU)$_{15}$ (SEQ ID NO: 2) | 0.06740 | 0.974 | 18.958 | 0.822 |
| (AT)$_{30}$ (SEQ ID NO: 3) | 0.06481 | 0.942 | 14.581 | 0.874 |
| (GC)$_{30}$ (SEQ ID NO: 4) | 0.06735 | 0.974 | 18.842 | 0.824 |
| (AT)$_{15}$ (SEQ ID NO: 5) | 0.06922 | 0.963 | 23.933 | 0.763 |
| (AAAT)$_7$ (SEQ ID NO: 6) | 0.06958 | 0.971 | 25.258 | 0.747 |
| (ATTT)$_7$ (SEQ ID NO: 7) | 0.06782 | 0.976 | 19.918 | 0.811 |
| (GGGT)$_7$ (SEQ ID NO: 8) | 0.06846 | 0.978 | 21.576 | 0.791 |
| (GTTT)$_7$ (SEQ ID NO: 9) | 0.07096 | 0.966 | 31.882 | 0.668 |
| DPPE-PEG(5000) | 0.06346 | 0.983 | 12.999 | 0.855 |
| DMPE-PEG(5000) | 0.07091 | 0.964 | 31.564 | 0.657 |
| DSPE-PEG(5000) | 0.06332 | 0.982 | 12.859 | 0.875 |
| DSPE-PEG(2000) | 0.07175 | 0.990 | 37.417 | 0.589 |
| DSPE-PEG(2000)-Cyanur | 0.06525 | 0.987 | 15.188 | 0.848 |
| DSPE-PEG(2000)-CA | 0.07028 | 0.992 | 28.211 | 0.696 |
| DSPE-PEG(2000)-Maleimide | 0.06897 | 0.991 | 23.123 | 0.755 |
| DSPE-PEG(2000)-PDP | 0.06948 | 0.989 | 24.883 | 0.735 |
| DSPE-PEG(2000)-Amine | 0.06664 | 0.983 | 17.440 | 0.821 |
| DSPE-PEG(2000)-Biotin | 0.06716 | 0.988 | 18.459 | 0.810 |
| DSPE-PEG(350) | 0.07304 | 0.983 | 52.292 | 0.416 |

It is assumed that the refractive indexes of the DNA, RNA, and phospholipid-PEG wrappings are equal to that of water (n=1.333). Based on the effective dielectric constant, it can be estimated the relative surface coverage of the SWCNT, $\alpha$, by its wrapping, by assuming a linear combination of the surrounding water ($\varepsilon_{water}$=88.1) and the wrapping polymer ($\varepsilon_r$) contributions:

$$\varepsilon_{eff} = \alpha \varepsilon_p + (1-\alpha)\varepsilon_{water} \quad (4)$$

where $\varepsilon_p$=4 for DNA and RNA wrappings[40] and $\varepsilon_p$=2.08 for the phospholipid wrappings. See, Hilmer, A. J., Tvrdy, K., Zhang, J. & Strano, M. S. Charge Transfer Structure-Reactivity Dependence of Fullerene-Single-Walled Carbon Nanotube Heterojunctions. *Journal of the American Chemical Society* 135, 11901-11910, doi:10.1021/ja404636b (2013), which is incorporated by reference in its entirety. The parameter $\alpha$ was used to rank the polymer wrappings in descending order (see FIG. 1C). As shown below, the molecular recognition of fibrinogen occurs for DPPE-PEG (5000) to the exclusion of the others, and this CoPhMoRe phase has one of the highest polymer surface coverages.

Protein Library Screening.

Figure 2A:
FIGS. 2A-2D show protein CoPhMoRe screen.

A library of 14 proteins of human origin was constricted, some of which are highly abundant in blood (such as albumin, IgG, fibrinogen, α1-antitrypsin, transferrin, haptoglobin, α2-macroglobulin, IgA, IgM, α1-acid-glycoprotein, and apoliporprotein A-I), whereas the others are relatively rare but of clinical significance (insulin, hCG, and CRP). See, Binder, C., Lauritzen, T., Faber, O. & Pramming, S. Insulin Pharmacokinetics. *Diabetes Care* 7, 188-199, doi: 10.2337/diacare.7.2.188 (1984), Braunstein, G. D., Rasor, J., Danzer, H., Adler, D. & Wade, M. E. Serum human chorionic gonadotropin levels throughout normal pregnancy. *Am J Obstet Gynecol* 126, 678-681 (1976), and Black, S., Kushner, I. & Samols, D. C-reactive Protein. *Journal of Biological Chemistry* 279, 48487-48490, doi:10.1074/jbc.R400025200 (2004), each of which is incorporated by reference in its entirety. The responses of the fluorescent emission of the DNA, RNA, and phospholipid-PEG SWCNT suspensions were recorded following an hour incubation with each of the proteins at 20 µg ml$^{-1}$ in phosphate buffered saline (PBS). The normalized fluorescence response of the joint peak of the (9,4) and (7,6) tubes, which is readily distinguishable, (FIG. 6B) is presented in a heat-map in FIG. 2A.

Figure 2B:
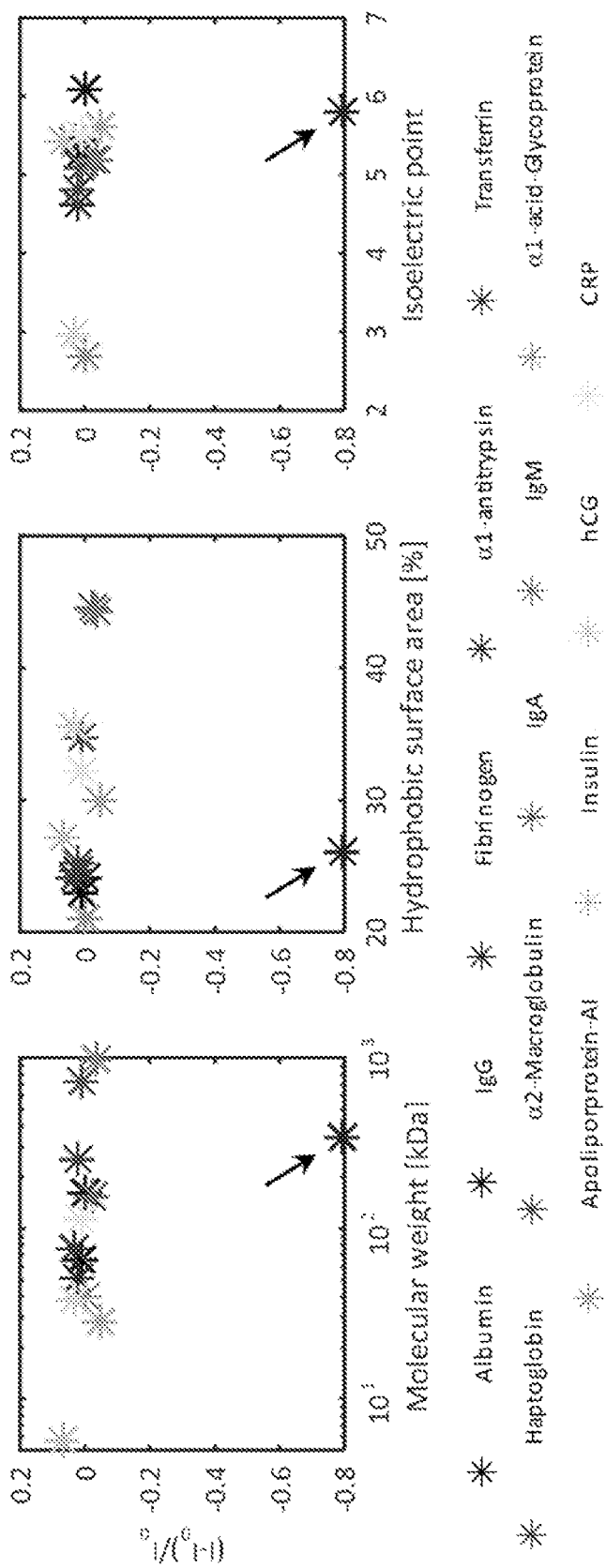

Manifested in the heat-map, the DPPE-PEG(5000)-SWCNT (FIG. 1A(i)) shows an obvious distinguishable response to fibrinogen, of an 80% decrease in fluorescence intensity, whereas other proteins induced a negligible response of less than 5% for this complex. Hence, the DPPE-PEG(5000) wrapped SWCNT can be considered as a selective sensor for fibrinogen. Protein parameters such as molecular weight, relative hydrophobic surface area, or isoelectric point, cannot explain the pronounced response of the DPPE-PEG(5000)-SWCNT fluorescence to fibrinogen, which appears as an outlier in plots of the normalized response as a function of these three variables (FIG. 2B).

Figure 1C:
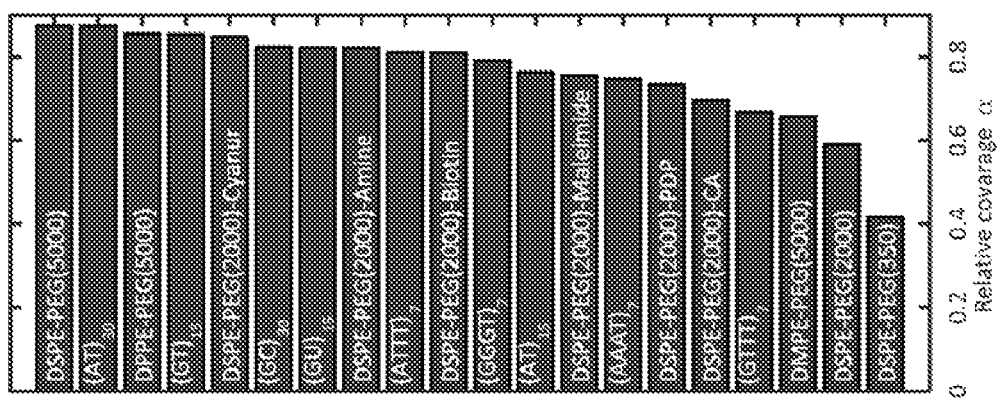
Figure 2C:
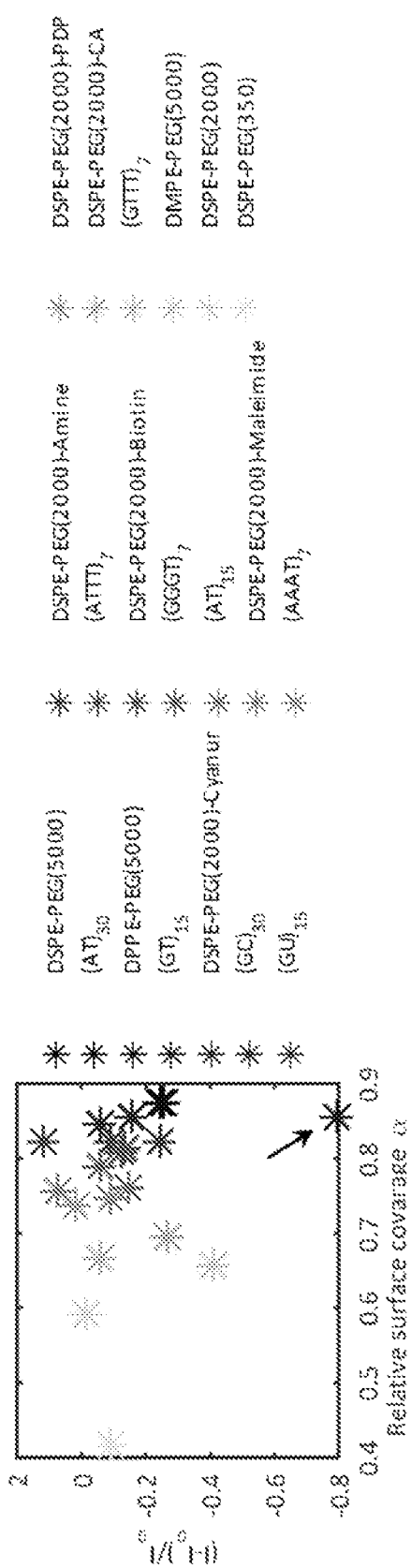

The DPPE-PEG(5000) wrapping which renders the SWCNT a selective sensor for fibrinogen has the second highest relative coverage of the SWCNT surface (85.5%) among the phospholipid-PEG wrappings, following DSPE-PEG(5000) with 87.5%, whereas the relative surface coverages of the rest of the phospholipid-PEG molecules were smaller than 85% (FIG. 1C). However, there was no evident correlation between the relative surface coverage and the normalized response to fibrinogen (FIG. 2C). Even when looking at the absolute value of the normalized response versus the surface coverage, the correlation factor, which was found to be 0.26, was not statistically significant. Among the DNA wrapping, all the responses to the proteins were smaller than 30% intensity modulation. In comparison, a recently published work showed that in response to small molecule neurotransmitters, DNA wrapped SWCNT exhibited up to 80% intensity modulation. See, Kruss, S. et al. Neurotransmitter Detection Using Corona Phase Molecular Recognition on Fluorescent Single-Walled Carbon Nanotube Sensors. *Journal of the American Chemical Society* 136, 713-724 (2013), which is incorporated by reference in its entirety.

The discovery of a CoPhMoRe phase for fibrinogen has several practical implications, as it is one of the largest and most abundant plasma proteins, having a molecular weight of 340 kDa and normal concentrations of 1.75-4.3 g L$^{-1}$. It has an elongated trinodular structure of 45-50 nm in length, consisting of two outer globular domains (D-domains) of 6.5 nm in diameter and one central globular domain (E-domain) of 5 nm in diameter, which are connected by coiled coils of helical chains of 1.5 nm in diameter. See, Nicoll, D., McPhee, S. J., Pignone, M., Chou, T. M. & Detmer, W. M. Pocket Guide to Diagnostic Tests. (Lange Medical Books/McGraw-Hill, 2000), Mosesson, M. W. Fibrinogen and fibrin structure and functions. *Journal of Thrombosis and Haemostasis* 3, 1894-1904 (2005), Yermolenko, I. S., Lishko, V. K., Ugarova, T. P. & Magonov, S. N. High-Resolution Visualization of Fibrinogen Molecules and Fibrin Fibers with Atomic Force Microscopy. *Biomacromolecules* 12, 370-379, doi:10.1021/bm101122g (2010), and Scheraga, H. A. The thrombing fibrinogen interaction. *Biophysical Chemistry* 112, 117-130 (2004), each of which is incorporated by reference in its entirety.

Fibrinogen is an important biomarker, and its plasma concentration has clinical value. It is an acute phase reactant, a coagulation factor, and the principal element of blood clots. The fibrinogen protein is synthesized in the liver. Increased fibrinogen levels can indicate inflammatory state, or pregnancy, whereas decreased levels can result from hepatic synthesis dysfunction, thrombosis, genetic diseases such as afibrinogenemia, hypofibrinogenemia, and dysfibrinogenemia, and disseminated intravascular coagulation.

See, Nicoll, D., McPhee, S. J., Pignone, M., Chou, T. M. & Detmer, W. M. *Pocket Guide to Diagnostic Tests*. (Lange Medical Books/McGraw-Hill, 2000), which is incorporated by reference in its entirety. The latter is associated with severe clinical conditions such as sepsis, trauma, cancer, obstetrical complications, vascular disorder, presence of toxins, and immunologic disorder. See, Levi, M. & ten Cate, H. Disseminated Intravascular Coagulation. *New England Journal of Medicine* 341, 586-592, doi:doi:10.1056/NEJM199908193410807 (1999), which is incorporated by reference in its entirety.

The coagulation cascade associated with the wound healing response can be initiated by the activation of either one of two possible pathways, extrinsic and intrinsic, which converge to a common pathway, in which prothrombin is converted into thrombin which hydrolyzes fibrinogen, forming insoluble fibrin monomers that polymerize to form a thrombus. Mosesson, M. W. The roles of fibrinogen and fibrin in hemostasis and thrombosis. *Semin Hematol* 29, 177-188 (1992), which is incorporated by reference in its entirety. The extrinsic pathway is initiated by the release of tissue factors through a broken blood vessel wall, whereas the intrinsic pathway is initiated by contact with negatively charged surfaces within a damaged vessel, such as exposed subendothelial tissue or collagen. See, Halkier, T. *Mechanisms in Blood Coagulation, Fibrinolysis and the Complement System*. (Cambridge University Press, 1991), which is incorporated by reference in its entirety. Direct methods for determining fibrinogen concentration in blood are based on immunological assays, such as enzyme-linked immunosorbent assays (ELISA), radial immunodiffusion (Mancini method), and gel electrophoresis followed by immunoblotting. See, Mackie, I. J. et al. Guidelines on fibrinogen assays. *British Journal of Haematology* 121, 396-404, doi:10.1046/j.1365-2141.2003.04256.x (2003), which is incorporated by reference in itsentirety. Supplementary functional assays for estimating the amount of active clottable fibrinogen such as thrombin time (TT), prothrombin time (PT), and partial thromboplastin time (PTT), involve the addition of an activator of one of the coagulation pathways to plasma samples, followed by a measurement of the clotting time[1,5]. Thrombin time tests the activation of fibrinogen to fibrin by adding high concentration of thrombin, prothrombin time screens the extrinsic pathway by adding tissue factors (thromboplastin) that are released upon vessel wall damage, and partial thromboplastin time screens the intrinsic pathway by adding ground glass to mimic the charged surface contact. Normal times are 20-30 sec for TT, 11-14 sec for PT, and 22-35 sec for PTT. See, Verhovsek, M., Moffat, K. A. & Hayward, C. P. Laboratory testing for fibrinogen abnormalities. *American journal of hematology* 83, 928-931 (2008), which is incorporated by reference inits entirety.

The fibrinogen protein is constructed by three pairs of mostly alpha-helix polypeptide chains (Aα, Bβ, and γ) linked by disulfide bonds. Its structure appears as three-nodules, one in the middle (E-domain), and two at each of the ends (D-domains), which are connected by helical chains. See, Yermolenko, I. S., Lishko, V. K., Ugarova, T. P. & Magonov, S. N. High-Resolution Visualization of Fibrinogen Molecules and Fibrin Fibers with Atomic Force Microscopy. *Biomacromolecules* 12, 370-379, doi:10.1021/bm101122g (2010), and Scheraga, H. A. The thrombin-fibrinogen interaction. *Biophysical Chemistry* 112, 117-130 (2004), each of which is incorporated by reference in its entirety. The total length of the fibrinogen molecule ranges between 45 nm-50 nm, the diameter of the middle and outer nodules are 5 nm and 6.5 nm, respectively, and the width of the interconnection helical coil is of the order of 1.5 nm[7]. The distribution of the possible angles between the two helical chains originating at the middle nodule was found to be bimodal with peaks around 157 and 106 degrees, granting the fibrinogen an elongated structure with high aspect ratio. See, Schönfeld, D. L., Ravelli, R. B. G., Mueller, U. & Skerra, A. The 1.8-Å Crystal Structure of α1-Acid Glycoprotein (Orosomucoid) Solved by UV RIP Reveals the Broad Drug-Binding Activity of This Human Plasma Lipocalin. *Journal of Molecular Biology* 384, 393-405 (2008), which is incorporate by reference in its entirety.

Figure 2D:
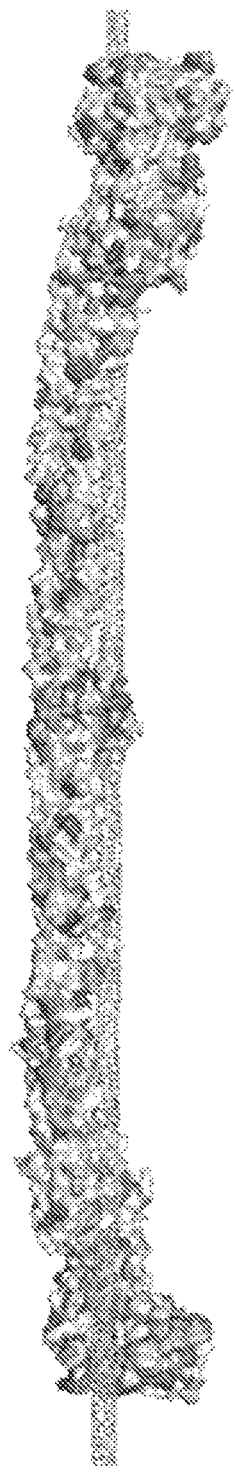

It can be hypothesized that both the corona phase specifically adopted by the DSPE-PEG(5000) upon adsorption onto the SWCNT surface and the unique conformation of the fibrinogen, an elongated molecule of high aspect ratio, which is distinctive relative to the structure of the other proteins in the study (FIG. 9), must be important factors in this molecular recognition. Moreover, the three dimensional structure of the fibrinogen enables multiple binding sites on the protein to be in close proximity to the SWCNT corona simultaneously, owing to the one dimensional structure of the nanotube, as illustrated in FIG. 2D.

SWCNT—Fibrinogen Interaction Spectroscopy.

Figure 3A:
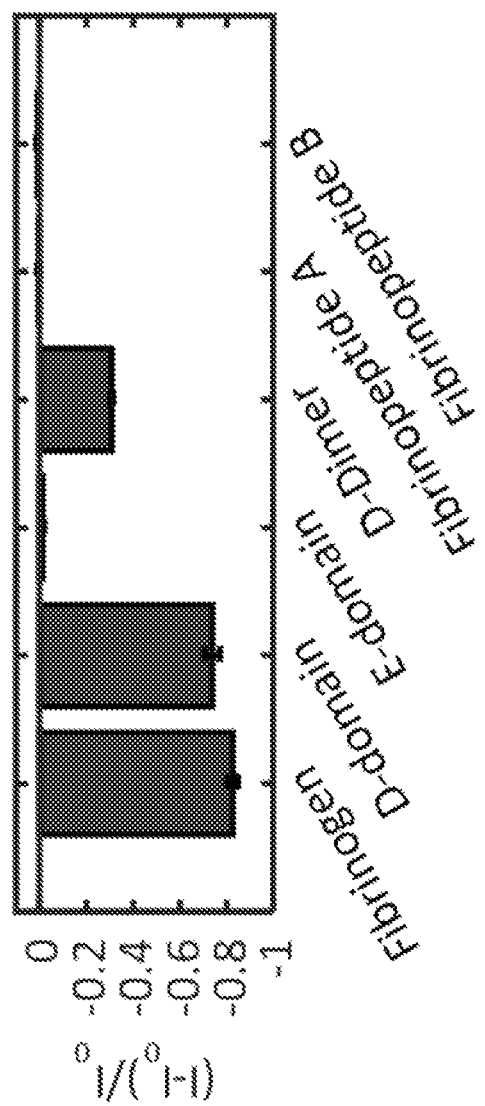
FIGS. 3A-3I show fluorescence spectroscopy of the SWCNT-fibrinogen interaction.

In order to elucidate the mechanism of fibrinogen binding, the response of the DPPE-PEG(5000)-SWCNT sensor was tested to various fibrinogen fragments, including the D-domain, E-domain, D-dimer, fibrinopeptide A, and fibrinopeptide B (FIG. 3A). A significant decrease in fluorescent emission, comparable to the response induced by the full length fibrinogen protein, was observed for the D-domain, while the D-dimer, which is comprised of two D-domains, showed a large response as well, but to a lesser extent. The E-domain and the two fibrinopeptides produced no response. Thus the two outer D-regions of the fibrinogen are the driving force of the interaction between the whole protein and the DPPE-PEG(5000)-SWCNT complex. Owing to the evident affinity between the D-region and the DPPE-PEG (5000)-SWCNT corona, the underlying interaction mechanism can be a three-step sequential binding initiated by one of the D-regions, followed by the other D-region, culminate in the binding of the middle E-region, leading to the strong interaction between the full length protein and the SWCNT scaffold. This is supported by previous studies showing multistage adsorption of fibrinogen onto surfaces (see Roach, P., Farrar, D. & Perry, C. C. Interpretation of Protein Adsorption: Surface-Induced Conformational Changes. *Journal of the American Chemical Society* 127, 8168-8173 (2005), which is incorporated by reference in its entirety), where an initial binding is followed by the reorientation of the elongated fibrinogen molecules.

Figure 3B:
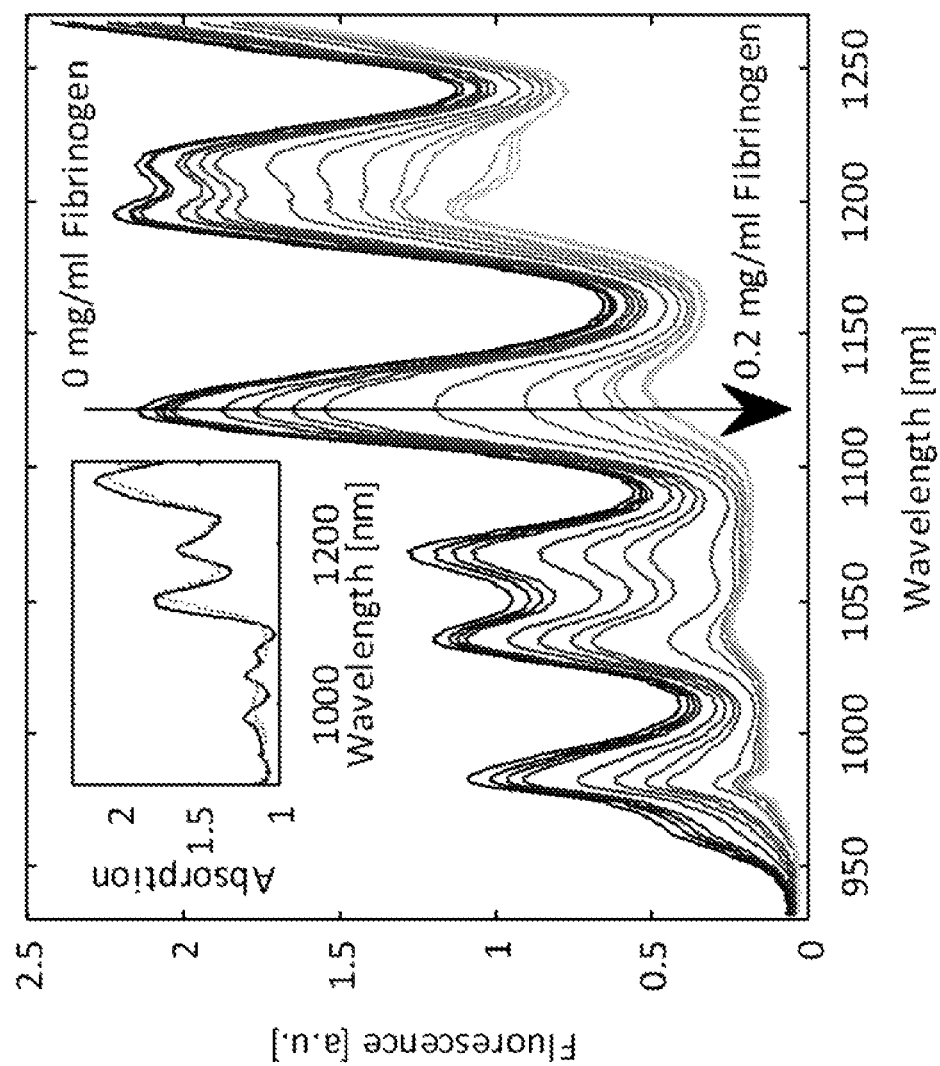
Figure 3C:
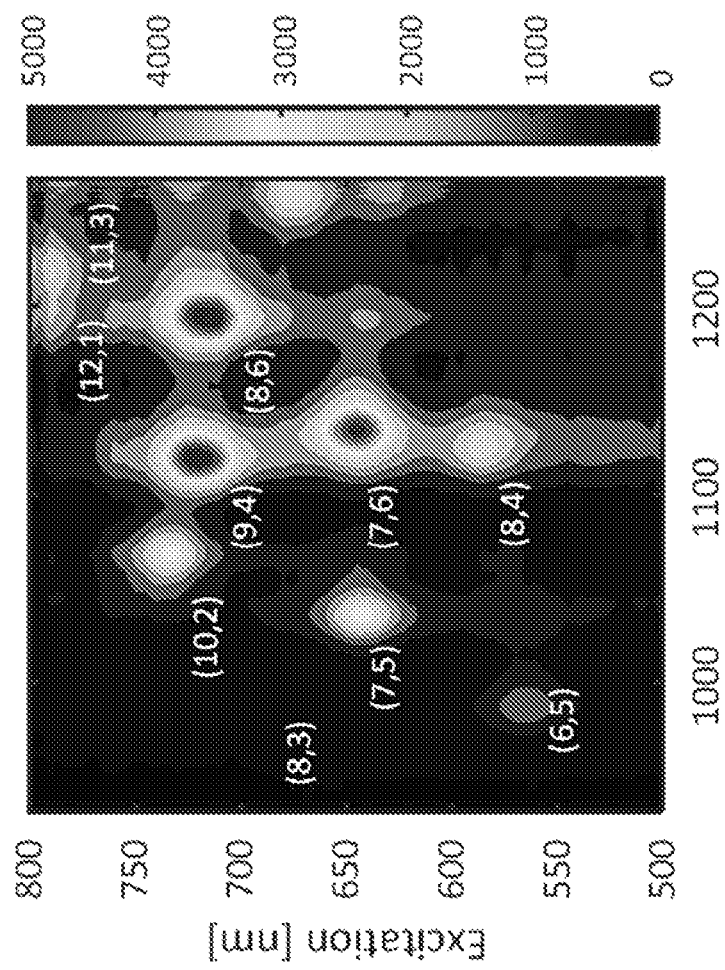
Figure 3D:
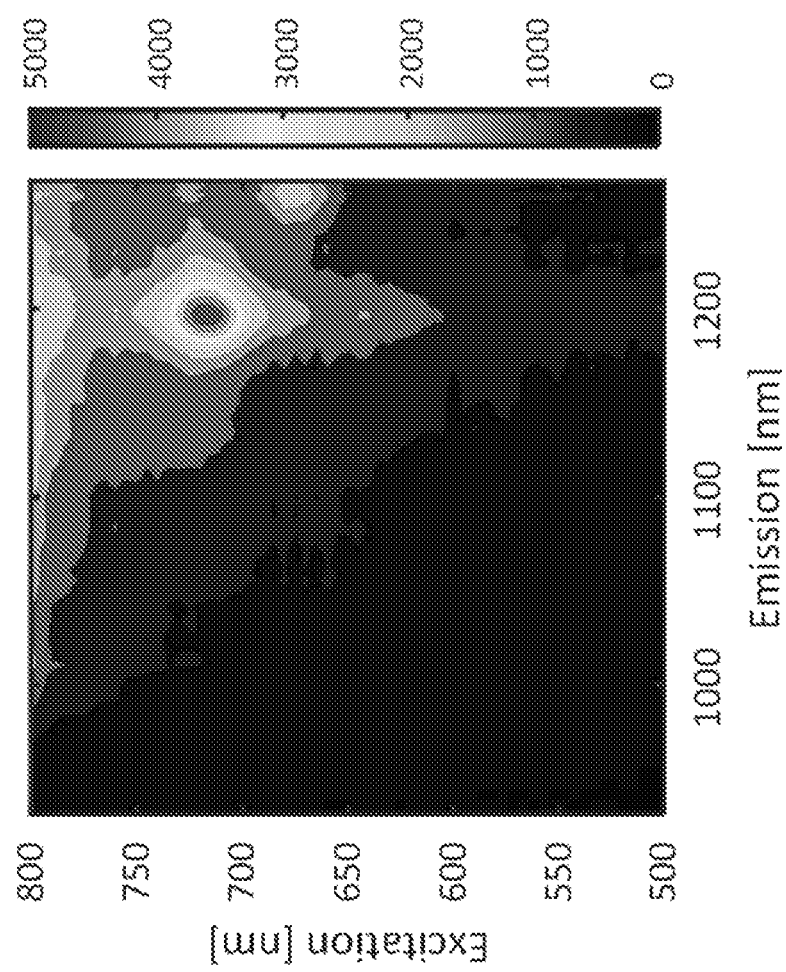

To support this mechanism, the fibrinogen concentration-dependent interaction was examined with the various SWCNT chiralities. See, Salem, D. P. et al. Chirality dependent corona phase molecular recognition of DNA-wrapped carbon nanotubes. *Carbon*, vol 97, February 2016, pp. 147-153. The fluorescent spectra of the DPPE-PEG(5000)-SWCNT was recorded with increasing concentrations of the protein, clearly observing a gradual decrease of the emission intensity, and a red shift of the emission peaks (FIG. 3B). The SWCNT absorption peaks height remains invariant to the addition of the fibrinogen, ruling out nanotube aggregation effects, while the absorption peak wavelength undergoes a modest redshift (FIG. 3B, inset), indicating an increase in the dielectric constant and higher water content in the close proximity of the nanotube surface. See, Hertel, T. et al. Spectroscopy of single- and double-wall carbon nanotubes in different environments. *Nano Lett* 5, 511-514, doi:Doi 10.1021/Nl050069a (2005), which is incorporated by reference in its entirety. The relative fluorescent response of the SWCNT with larger band gaps, corresponding to smaller diameters (see, Bachilo, S. M. et al. Structure-Assigned Optical Spectra of Single-Walled Carbon Nanotubes. *Science* 298, 2361-2366, doi:10.1126/science.1078727 (2002), which is incorporated by reference in its entirety), is more pronounced relative to the larger diameter nanotubes, manifested in the excitation emission profiles of the SWCNT sample before (FIG. 3C) compared to after (FIG. 3D) the addition of fibrinogen.

Figure 3E:
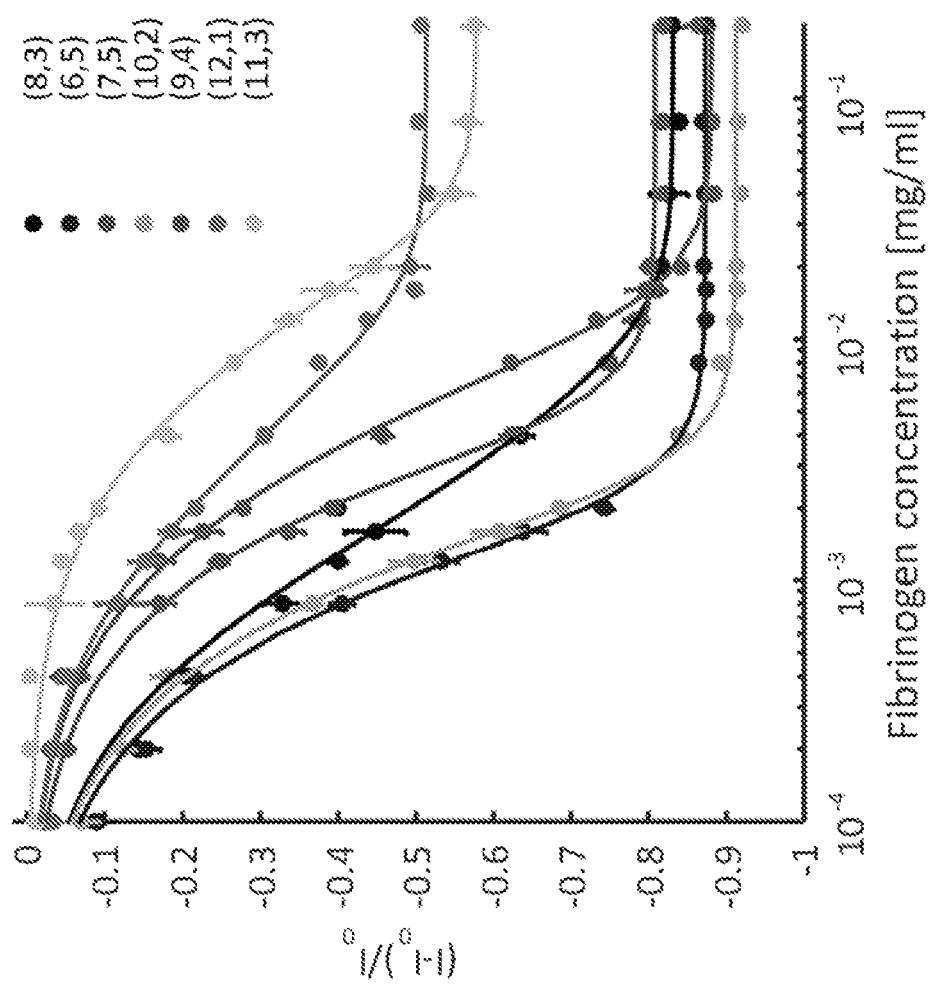

The fluorescent emission spectra in FIG. 3B were deconvoluted to the various SWCNT chiralities within the sample (FIG. 5) in order to analyze each chirality independently. The normalized fluorescent response of each nanotube species is plotted in FIG. 3E versus the fibrinogen concentration in the solution, yielding a calibration curve of the fibrinogen sensor. Following the three-step sequential binding hypothesis, the fibrinogen—DPPE-PEG(5000)-SWCNT interaction is modeled by the following reaction scheme (see Weiss, J. N. The Hill equation revisited: uses and misuses. *The FASEB Journal* 11, 835-841 (1997), which is incorporated by reference in its entirety):

$$\theta + 2D + E \xrightleftharpoons{K_{d1}} \theta D + D + E \xrightleftharpoons{K_{d2}} \theta D_2 + E \xrightleftharpoons{K_{d3}} \theta D_2 E \quad (5)$$

Where $\theta$ is an empty binding site on the SWCNT surface, D and E stand for a D- and E-regions of the fibrinogen, respectively, and $K_{d1}$, $K_{d2}$, and $K_{d3}$ are the corresponding dissociation constants. In order to simplify the picture, it is assumed that upon the initial binding of the first D-region, the fibrinogen molecule aligns with the SWCNT principle axis, and the remaining D- and E-regions bind instantaneously, and the last two steps of the reaction are combined as follows:

$$\theta + 2D + E \xrightleftharpoons{K_{d1}} \theta D + D + E \xrightleftharpoons{K_{d23}} \theta D_2 E \quad (6)$$

where $K_{d23} = K_{d2} K_{d3}$. For further simplicity, the two types of the fibrinogen domains are labeled by L, which now stands for a single nodule of the protein molecule:

$$\theta + 3L \xrightleftharpoons{K_{d1}} \theta L + 2L \xrightleftharpoons{K_{d23}} \theta L_3 \quad (7)$$

The total binding sites remains constant and thus fulfills the following equality:

$$[\theta]_{total} = [\theta] + [\theta L] + [\theta L_3] \quad (8)$$

where the brackets represent concentration of the relevant variable.

Figure 3F:
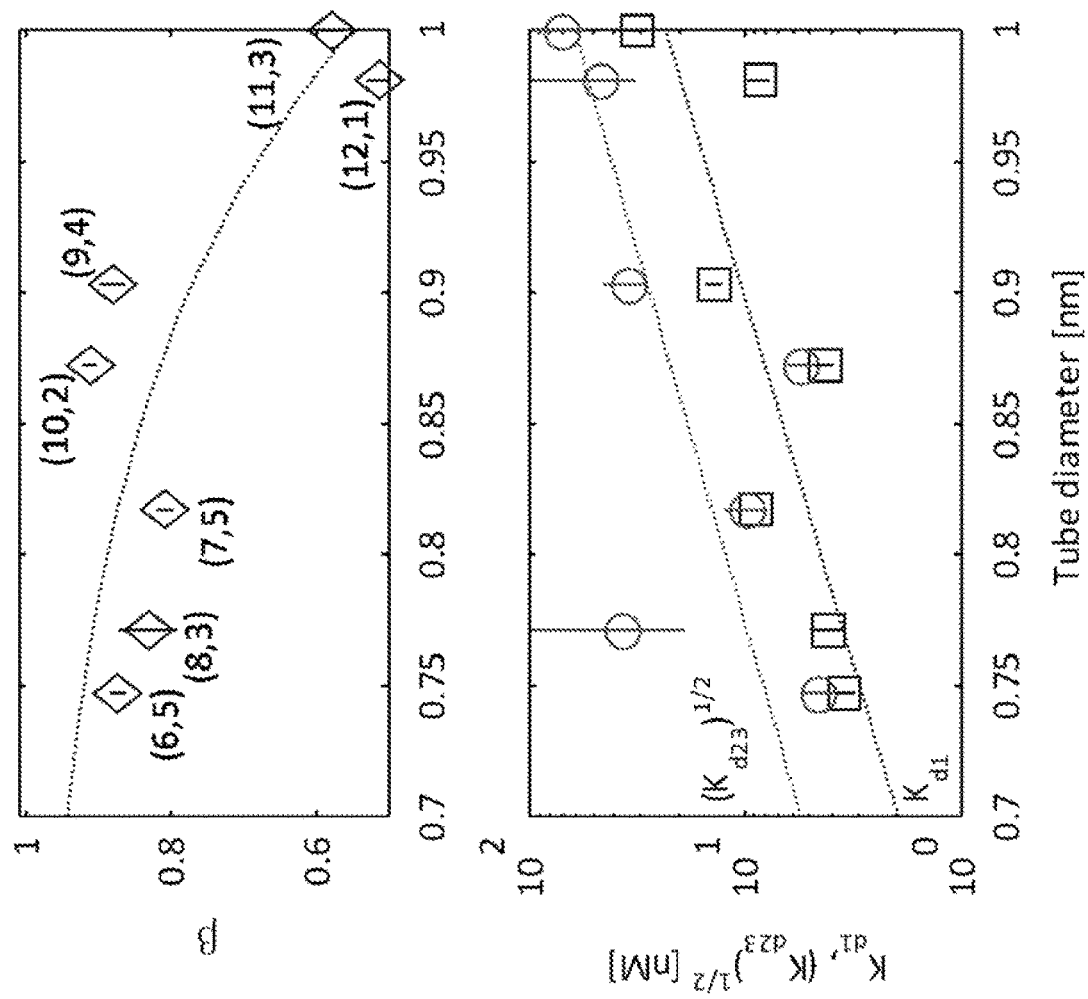

The normalized fluorescent intensity response is linearly proportional to the relative number of bound sites on the SWCNT surface:

$$\frac{I - I_0}{I_0} = \beta\left(1 - \frac{[\theta]}{[\theta]_{total}}\right) = \beta\left(1 - \frac{1}{1 + K_{d1}^{-1}[L] + (K_{d1} K_{d23})^{-1}[L]^3}\right) \quad (9)$$

where $I_0$ and I are the initial and final fluorescent intensity, and is the proportional factor. The fit to the data is plotted in FIG. 3E (solid lines), and the corresponding fit parameters, $\beta$, $K_{d1}$, and $(K_{d23})^{1/2}$ and their 95% confidence intervals are summarized in FIG. 3F (diamonds in the top panel, and blue squares and red circles in the bottom panel, respectively). Since $(K_{d23})^{1/2}$ is larger than $K_{d1}$, it can be concluded that there is no accumulation of the intermediate reactants, implying that once the first nodule of the fibrinogen is bound, the complete binding of rest of the molecule follows. See, Weiss, J. N. The Hill equation revisited: uses and misuses. *The FASEB Journal* 11, 835-841 (1997), which is incorporated by reference in its entirety.

Figure 3G:
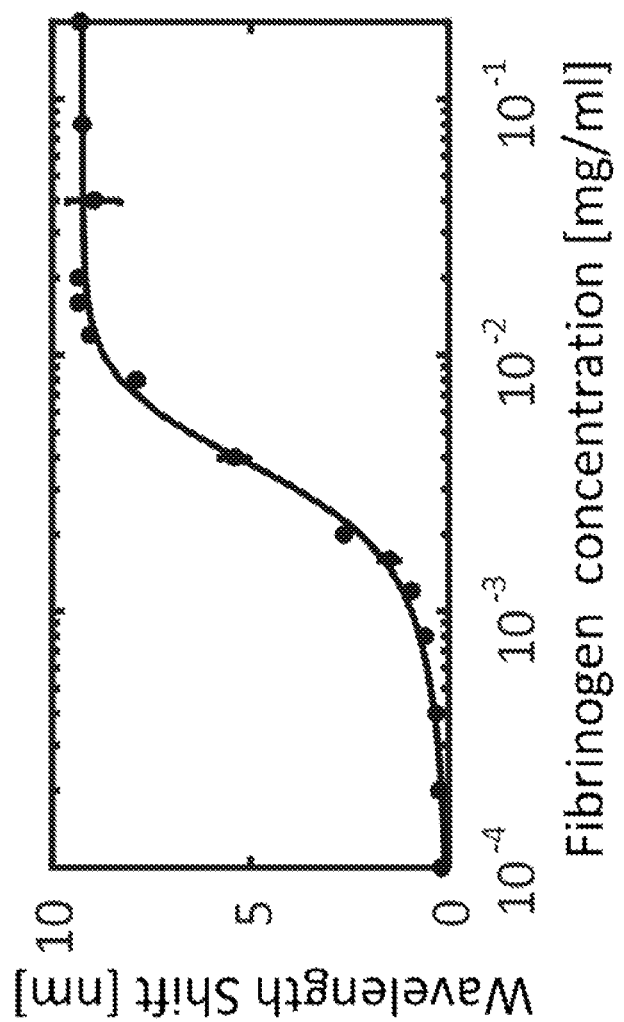

Based on the deconvolution data, the wavelength redshift of the (6,5) fluorescent emission peak versus the fibrinogen concentration in the solution was plotted, yielding an additional calibration curve for the fibrinogen sensor (FIG. 3G). The advantage of calibrating based on the wavelength shift, as opposed to the intensity modulation, is that the units in this case are not arbitrary and can be taken to be either the wavelength or the energy, eliminating the need for an internal standard or pre-calibration. The fit to the data points was achieved using the same model described above, yielding the fit parameters $K_{d1}=30.11$ nM, and $(K_{d23})^{1/2}=7.41$ nM, both within one order of magnitude of the fit parameters in the normalized intensity modulation calibration.

This observed solvatochromic shift corresponds to an increase of the dielectric constant in the close proximity of the SWCNT due to the adsorption of the fibrinogen molecules on the nanotubes' surface. See, Choi, J. H. & Strano, M. S. Solvatochromism in single-walled carbon nanotubes. *Applied Physics Letters* 90, 223114-223114-223113, doi: 10.1063/1.2745228 (2007), which is incorporated by reference in its entirety. Such an effect, explained by dielectric screening of repulsive Coulomb interactions (see Ohno, Y. et al. Excitonic transition energies in single-walled carbon nanotubes: Dependence on environmental dielectric constant. *physica status solidi* (b) 244, 4002-4005 (2007), which is incorporated by reference in its entirety), has been shown to induce a decrease in fluorescent emission intensity (see Gao, J., Gomulya, W. & Loi, M. A. Effect of medium dielectric constant on the physical properties of single-walled carbon nanotubes. *Chemical Physics* 413, 35-38 (2013), which is incorporated by reference in its entirety), and hence plays an important role in the underlying quenching mechanism in this case. Moreover, a quenching effect of SWCNT fluorescent emission was previously reported for proteins adsorbed directly onto the surface of the nanotubes in the work of Barone et al. for example, where a significant decrease in emission intensity was observed upon the exchange of a tightly packed sodium cholate wrapping with a glucose oxidase layer. See Barone, P. W., Baik, S., Heller, D. A. & Strano, M. S. Near-infrared optical sensors based on single-walled carbon nanotubes. *Nat Mater* 4, 86-92 (2005), which is incorporated by reference in its entirety.

Figure 3H:
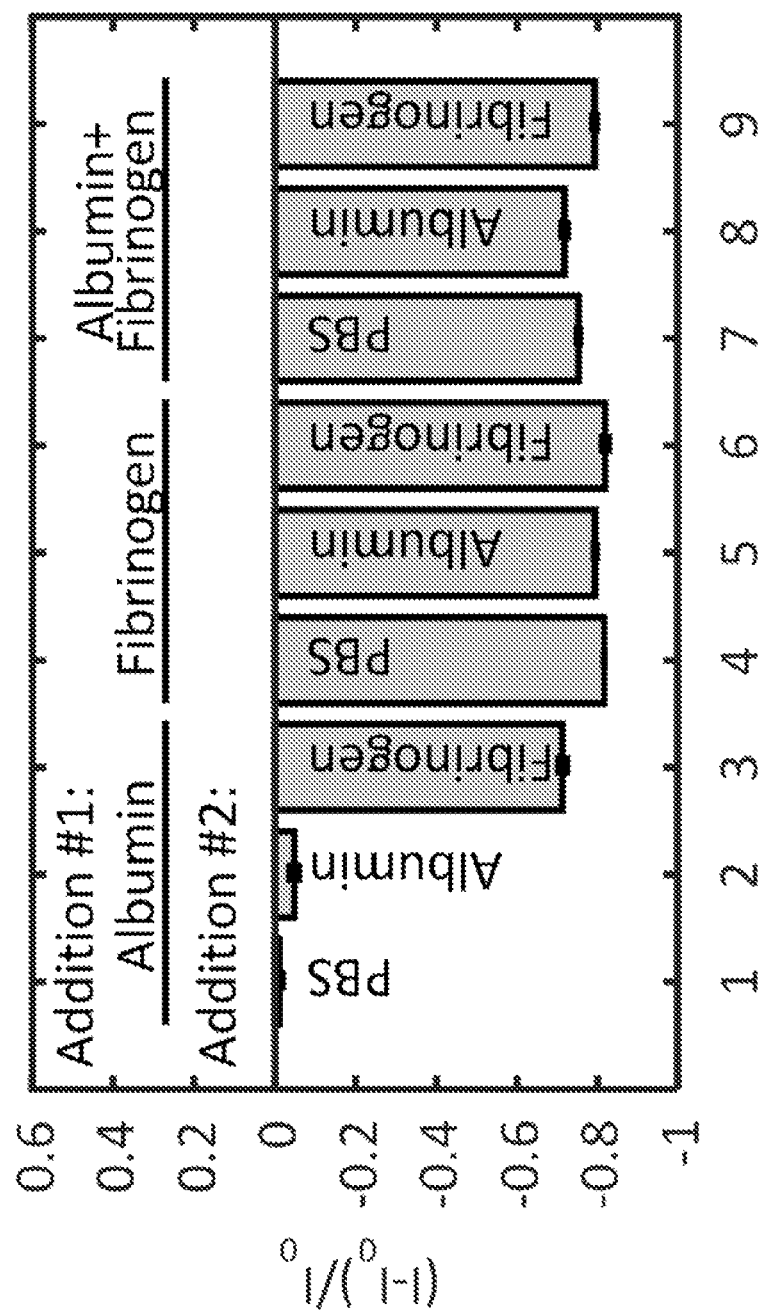
Figure 3I:
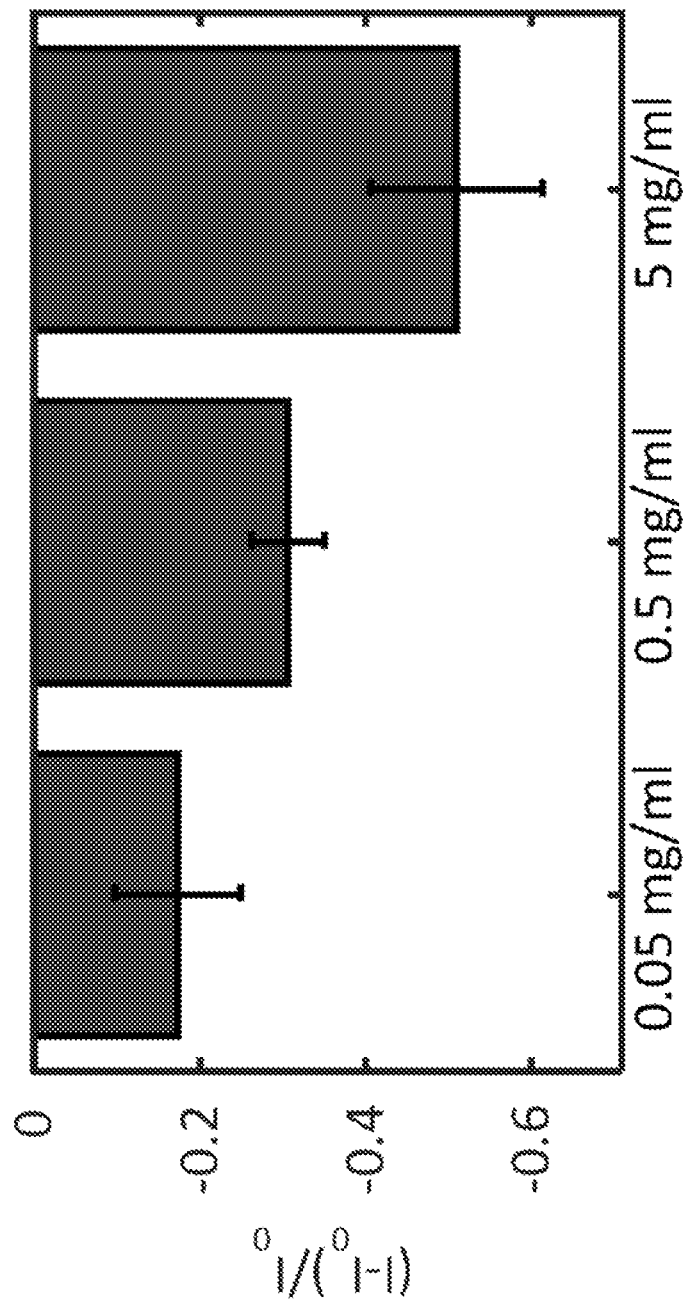

In order to assess the sensor performance in a complex environment, its response to fibrinogen was tested in the presence of albumin (FIG. 3H), which is the most abundant protein in the blood and constitutes about half of all the plasma proteins. See, Evans, T. W. Review article: albumin as a drug-biological effects of albumin unrelated to oncotic pressure. *Alimentary Pharmacology & Therapeutics* 16, 6-11 (2002), which is incorporated by reference in its entirety. A DPPE-PEG(5000)-SWCNT suspension was first incubated with either albumin (FIG. 3H, columns 1-3), fibrinogen (columns 4-6), or an equal mixture of both proteins (columns 7-9), followed by the addition of just buffer (PBS, columns 1, 4, 7), albumin (columns 2, 5, 8), or fibrinogen (columns 3, 6, 9). In contrast to the interaction with albumin, which produces little to no response (columns 1, 2), the addition of fibrinogen results in a significant fluorescence decrease (columns 3-9), regardless of the order of the addition of the proteins. Further, the response of the fibrinogen sensor was tested in serum environment by adding fibrinogen solution to DPPE-PEG(5000)-SWCNT suspension in 10% fetal bovine serum in PBS, to a final fibrinogen concentration of 0.05 mg ml$^{-1}$, 0.5 mg ml$^{-1}$, and 5 mg ml$^{-1}$ (FIGS. 3I and 10A). The normal fibrinogen concentrations in human blood are between 1.75 and 4.3 mg ml$^{-1}$, and are included in the tested range. The SWCNT sensor showed a significant signal quenching in response to fibrinogen of 17%, 31%, and 47% for the tested protein concentrations, respectively. Compared to the sensor response in PBS solution with similar conditions (90% quenching for 5 mg ml$^{-1}$ protein concentration, FIG. 10B), the response in serum is less pronounced, in agreement with previously published results (see, Gong, X., Sharma, A. K., Strano, M. S. & Mukhopadhyay, D. Selective Assembly of DNA-Conjugated Single-Walled Carbon Nanotubes from the Vascular Secretome. *ACS Nano* 8, 9126-9136 (2014), and Cherukuri, P. et al. Mammalian pharmacokinetics of carbon nanotubes using intrinsic near-infrared fluorescence. *Proceedings of the National Academy of Sciences* 103, 18882-18886 (2006), each of which is incorporated by reference in its entirety) showing that many serum components interact with SWCNT and can interfere with the interaction with the fibrinogen in this case.

An additional spectroscopy tool that can be utilized to determine the structure and conformation of proteins is circular dichroism (CD). The CD spectrum of fibrinogen shows two peaks, in 209 nm and 220 nm (FIG. 11, black solid curve), in agreement with previous findings, and is typical to the mostly alpha helical structure found in fibrinogen. See, McMillin, C. R. & Walton, A. G. A circular dichroism technique for the study of adsorbed protein structure. *Journal of Colloid and Interface Science* 48, 345-349 (1974), and Chen, Y.-H., Yang, J. T. & Chau, K. H. Determination of the helix and β form of proteins in aqueous solution by circular dichroism. *Biochemistry* 13, 3350-3359, doi:10.1021/bi00713a027 (1974), each of which is incorporated by reference in its entirety. The DPPE-PEG(5000)-SWCNT, however, has no characteristic CD signature (see Dukovic, G. et al. Racemic Single-Walled Carbon Nanotubes Exhibit Circular Dichroism When Wrapped with DNA. *Journal of the American Chemical Society* 128, 9004-9005, doi:10.1021/ja062095w (2006), and McNicholas, T. P. et al. Structure and Function of Glucose Binding Protein—Single Walled Carbon Nanotube Complexes. *Small* 8, 3510-3516, doi:10.1002/smll.201200649 (2012), each of which is incorporated by reference in its entirety) except for mild absorption (FIG. 11, dotted green curve). Comparing the CD spectra of fibrinogen with DPPE-PEG(5000)-SWCNT (FIG. 11, dashed blue curve) to a pure fibrinogen solution, the positions of the two major peaks remain invariant, indicating that the SWCNT corona phase did not catalytically denature the fibrinogen protein.

The Raman scattering spectrum of the DPPE-PEG(5000)-SWCNT also remains invariant to the interaction with fibrinogen, including the G-peak position and the G/D peak ratio (FIGS. 12A-12C), assuring that there is no covalent interaction between the fibrinogen molecule and the carbon lattice of the nanotube, which keeps its sp2 hybridization. See, Kruss, S. et al. Neurotransmitter Detection Using Corona Phase Molecular Recognition on Fluorescent Single-Walled Carbon Nanotube Sensors. *Journal of the American Chemical Society* 136, 713-724 (2013), which is incorporated by reference in its entirety. The net surface charge of both the fibrinogen and DPPE-PEG(5000)-SWCNT does not change upon their interaction, shown by constant zeta-potential values for all cases (FIG. 12D).

SWCNT—Fibrinogen Interaction Dynamics.

Figure 4A:
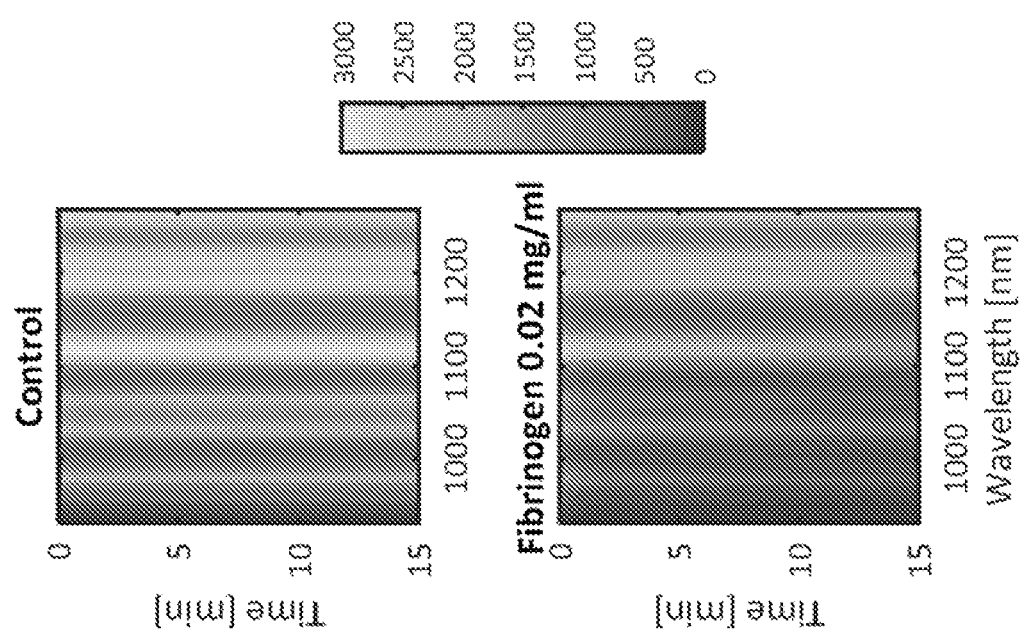
FIGS. 4A-4J show dynamics of the SWCNT-fibrinogen interaction.

The emission spectra of DPPE-PEG(5000)-SWCNT, to which either PBS or fibrinogen was added, were recorded every 2 seconds under continuous 785 nm laser excitation for 15 minutes (FIG. 4A). The fluorescent intensity of the DPPE-PEG(5000)-SWCNT suspension rapidly drops following the addition of fibrinogen, while the emission intensity of the control sample remains stable throughout the course of the experiment. This is manifested by tracking the (10,2) chirality peak, at 1069 nm, in both cases (FIG. 4B).

In order to fit the dynamic data, the rate equation resulting from the model in equation (9) was numerically integrated:

$$\frac{d}{dt}\left(\frac{[\theta L]}{[\theta]_{tot}}\right) = \\ k_{f1}[L]^3 - (k_{f1}[L]^3 + (k_{r1} + k_{f2})[L]^2)\frac{[\theta L]}{[\theta]_{tot}} + (k_{r2} - k_{f1}[L]^3)\frac{[\theta L_3]}{[\theta]_{tot}} \\ \frac{d}{dt}\left(\frac{[\theta L_3]}{\theta_{tot}}\right) = k_{f2}\frac{[\theta L]}{[\theta]_{tot}}[L]^2 - k_{r2}\frac{[\theta L_3]}{[\theta]_{tot}} \tag{10}$$

where $k_{f1}$, $k_{f2}$, and $k_{r1}$, $k_{r2}$ are the forward and the reverse rate constants of the first and second sequential steps in the association model, respectively, such that $K_{d1}=k_{r1}/k_{f1}$ and $K_{d23}=k_{r2}/k_{f2}$. The fit parameters resulted in $K_{d1}$=39.7 nM and $(K_{d23})^{1/2}$=42.7 nM, which is within one order of magnitude agreement with the dissociation contents of the (10,2) chirality peak calculated from the calibration curve fit (4.3 nM and 5.34 nM, respectively, FIG. 3E). A possible source for the difference is the additional data processing performed on the calibration data, which involved deconvoluting the spectra to find the individual fluorescent intensity contribution of the various nanotube chiralities in the sample.

Figure 4C:
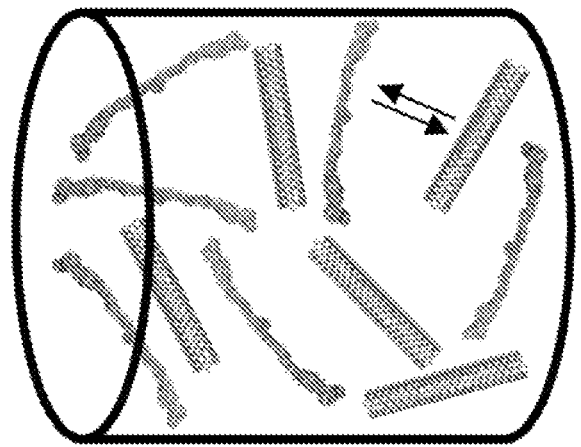
Figure 4B:
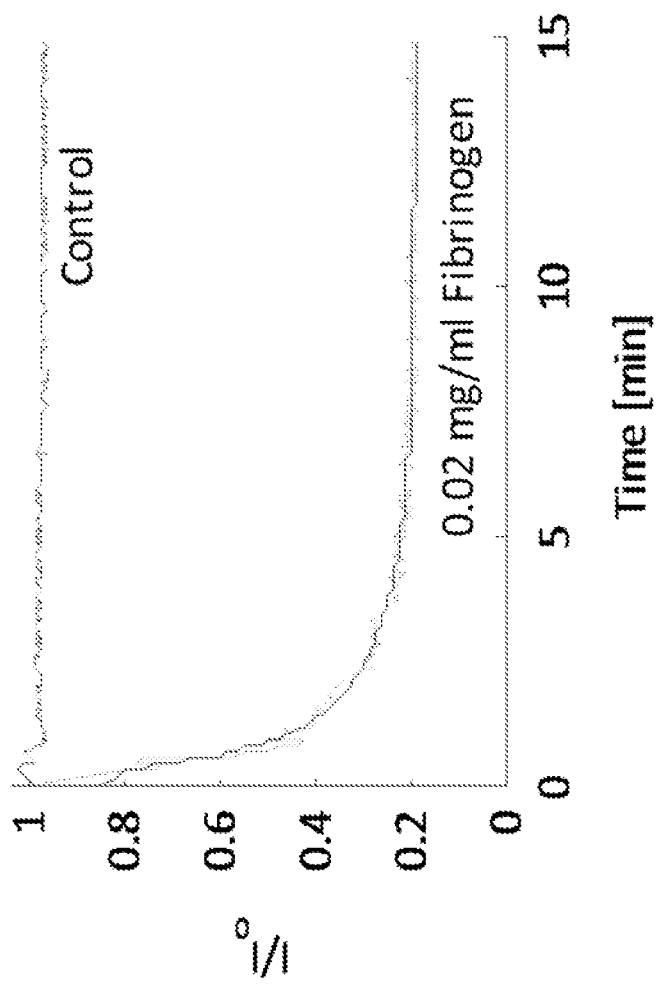
Figure 4D:
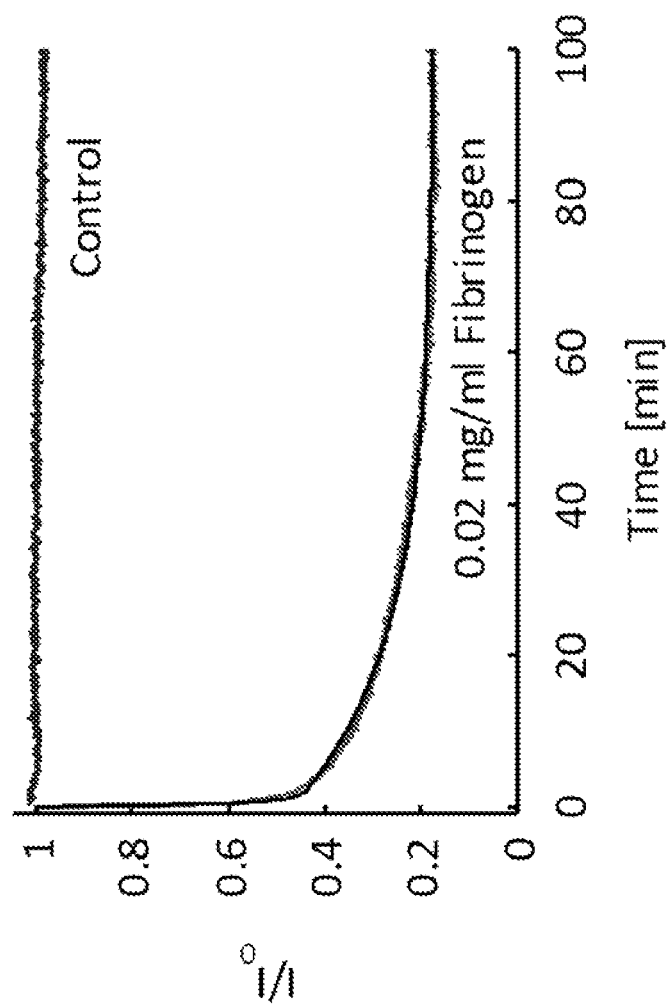
Figure 4E:
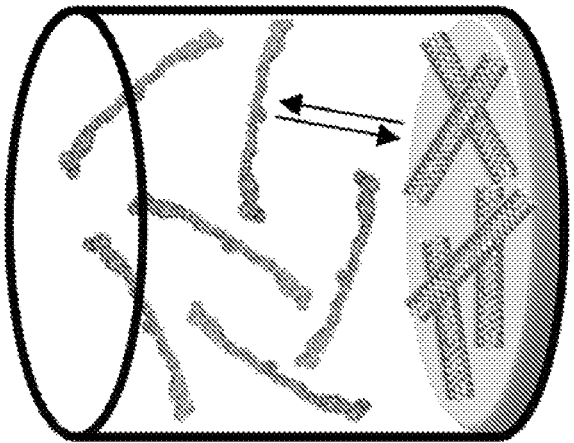

Given that this set of experiments was done in solution phase as illustrated in FIG. 4C, one can speculate about the role that free DPPE-PEG(5000) polymer plays in the interaction and signal transduction. To address this, the DPPE-PEG(5000)-SWCNT was immobilized on top of a thin agarose hydrogel bed (see Nelson, J. T. et al. Mechanism of Immobilized Protein A Binding to Immunoglobulin G on Nanosensor Array Surfaces. *Analytical Chemistry*, doi: 10.1021/acs.analchem.5b00843 (2015), which is incorporated by reference in its entirety), followed by exhaustive washing of any unbound SWCNT or polymer molecules. The fluorescent emission peak of the (6,5) SWCNT chirality was monitored over 100 minutes, where both a control sample and a sample to which fibrinogen was added showed similar behavior to the solution phase experiments, but on a longer time scale (FIG. 4D). This is expected based on the fact that only the fibrinogen molecules are mobile and can diffuse in the solution and the agarose hydrogel, while the SWCNT sensors are immobilized within the gel (FIG. 4E). Fitting the dynamic data with numerical integration of equation (10) results in $K_{d1}$=49.8 nM and $(K_{d23})^{1/2}$=33.7 nM, which is within approximately one order of magnitude agreement with the dissociation contents of the (6,5) chirality peak calculated from the calibration curve fit (3.5 nM and 4.4 nM, respectively, FIG. 3E). Similarly, a source for the difference is that the immobile sensor single channel detector integrates the fluorescent emission in the range of 950 nm to 1050 nm, whereas the calibration spectra were recorded with a nIR spectrometer and were deconvoluted to the various SWCNT chiralities in the suspension.

Figures 4F, 4G:
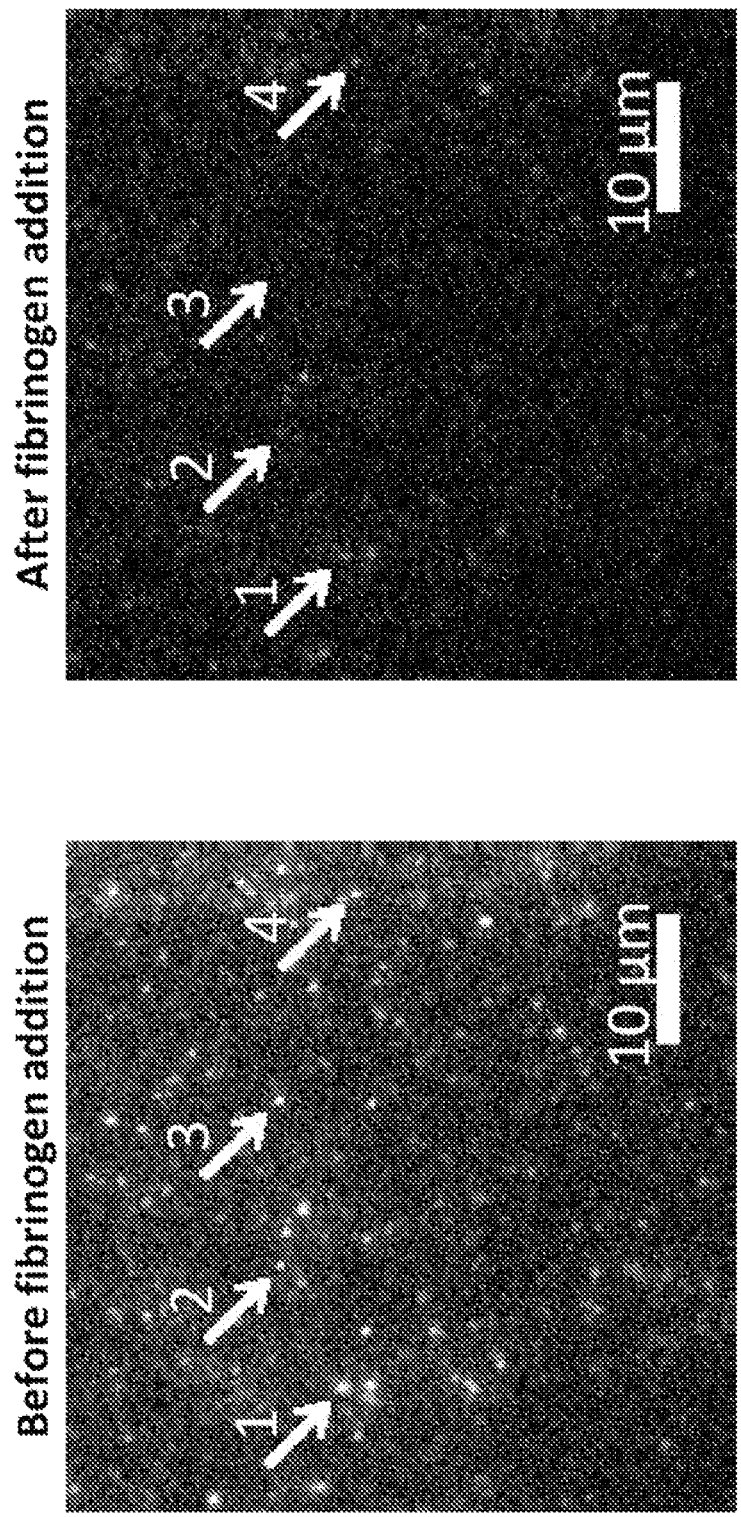
Figure 4H:
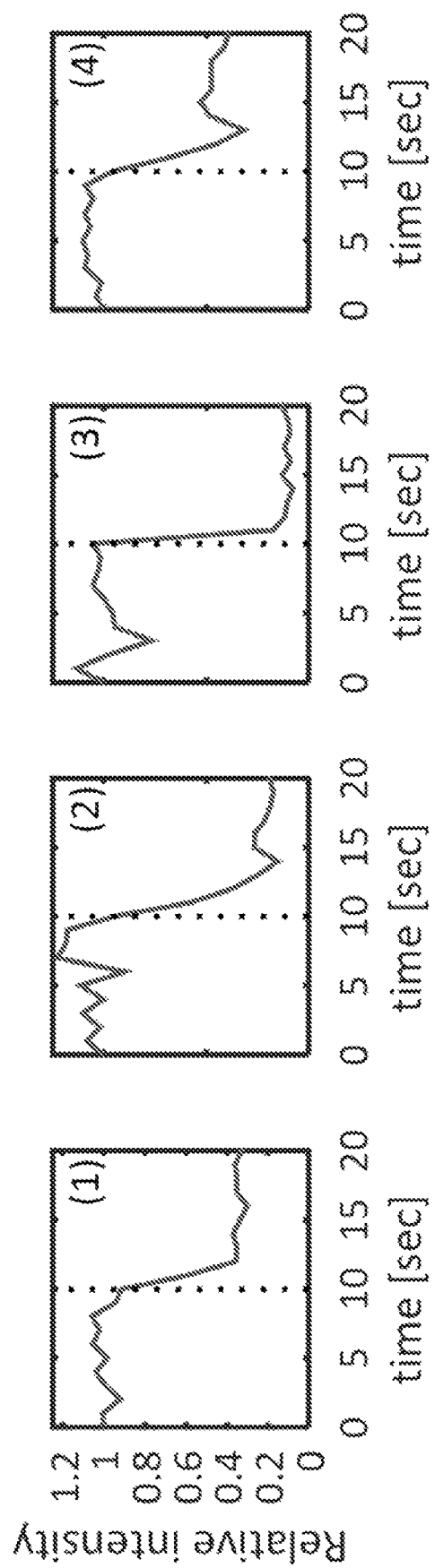

Further experiments were conducted with surface immobilized single SWCNT to conclusively demonstrate that nanoparticle aggregation is not responsible for the optical response. DPPE-PEG(5000)-SWCNT solution was deposited on a glass slide and was left to dry. Subsequently, the slide was extensively washed to remove any unbound nanotubes from the surface. The fluorescence of the individual nanotubes was imaged continuously using a 2D nIR camera attached to an inverted microscope, allowing the visualization of diffraction limited spots of single nanotubes (FIG. 4F). Following the addition of fibrinogen, the fluorescent emission intensity significantly decreases (FIG. 4G), as evident from the intensity traces over time (FIG. 4H). These results support the claim that the mechanism of emission intensity decrease does not involve nanotubes aggregation effects, since a similar decrease is observed when the SWCNT are either in solution phase, or immobilized within a hydrogel or on a glass slide, where they cannot aggregate.

Figure 4I:
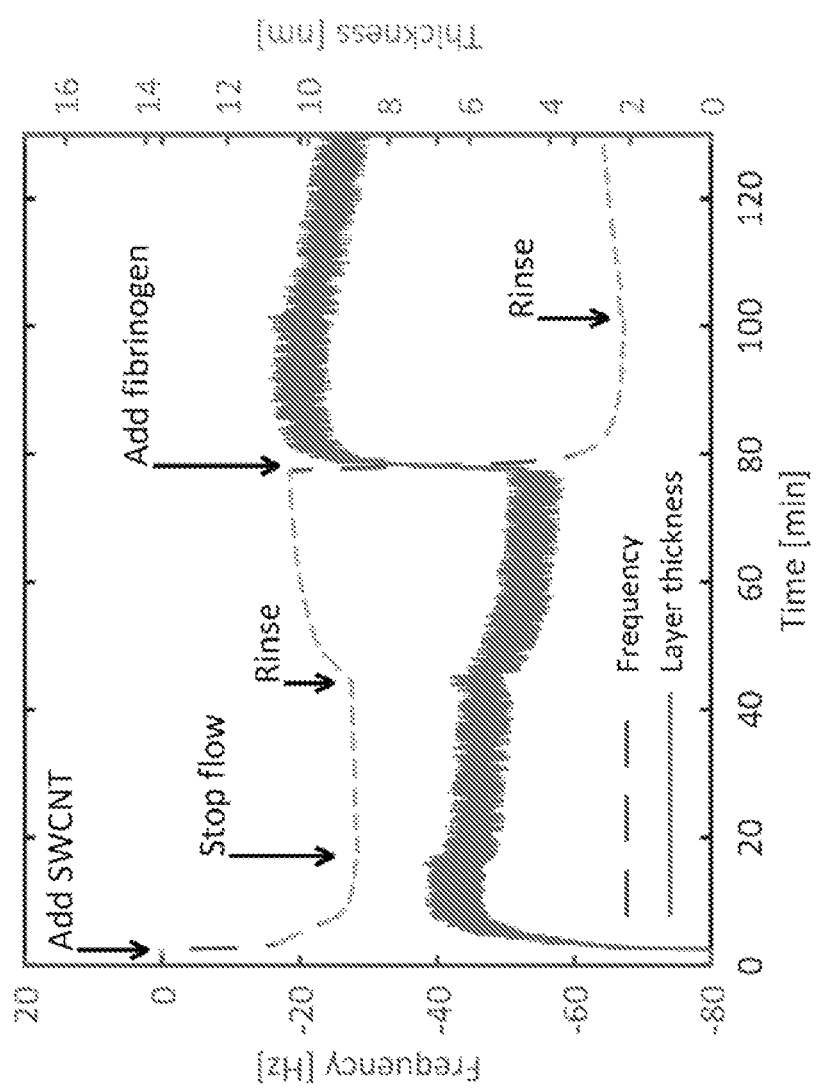
Figure 4J:
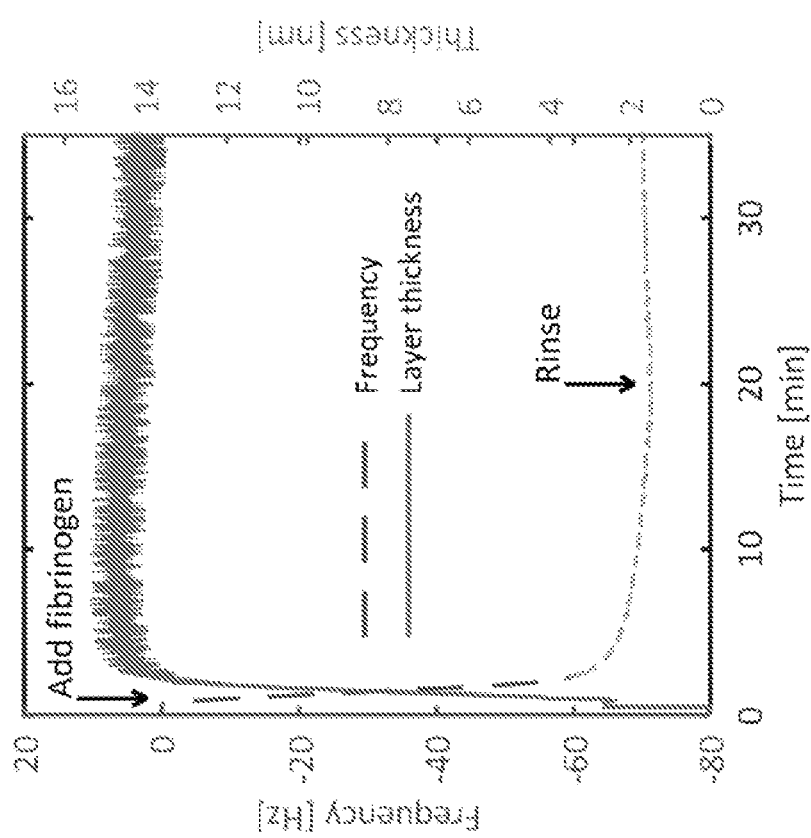

The gradual adsorption of the fibrinogen proteins to the DPPE-PEG(5000)-SWCNT was further verified by quartz crystal microbalance with dissipation (QCM-D) measurements. The QCM-D instrument (Q-sense E4) was used to gain additional insight on this process by monitoring the adsorption of the fibrinogen proteins onto a nanotube layer deposited on a gold coated crystal and calculating the resulting layers' thickness. Both of the adsorption steps demonstrated a gradual decrease in the frequency of the oscillating crystal, indicating a gradual increase in the layer thickness (FIG. 4I). The thickness of the SWCNT bottom layer was estimated as 4.4±0.1 nm, and the total thickness of both the SWCNT and the fibrinogen layers was estimated as 9.4±0.2 nm, yielding a protein layer of approximately 5 nm in thickness. In the case of SWCNT, the PBS wash resulted in the loss of approximately 20% of the layer thickness, whereas in the fibrinogen layer, the rinse resulted in the removal of approximately 25% of the layer. In contrast, when the fibrinogen solution was added directly to a gold coated quartz crystal surface, the final thickness of the protein layer was 14.2±0.1 nm (FIG. 4J), which is more than twice the thickness of the fibrinogen layer formed on top of the SWCNT layer. Previous studies of fibrinogen adsorption onto a gold surface using QCM-D technique have shown that the fibrinogen proteins form a monolayer on the surface (see Choukourov, A., Grinevich, A., Saito, N. & Takai, O. SPM analysis of fibrinogen adsorption on solid surfaces. *Surface Science* 601, 3948-3951 (2007), which is incorporated by reference in its entirety), in agreement with the widely accepted assumption of a monolayer surface-adsorption of proteins in general. See, Horbett, T. A. Principles underlying the role of adsorbed plasma proteins in blood interactions with foreign materials (Chapter 13). *Cardiovascular Pathology* 2, 137-148 (1993), which is incorporated by reference in its entirety. Taking into account the physical dimensions of the protein, these findings imply that the fibrinogen molecules mostly lay horizontally flat (side on) when adsorbed onto the DPPE-PEG(5000)-SWCNT, whereas when adsorbed directly onto the gold surface, they can adopt different configurations, including an end-on adsorption with the other unbound end sticking out into the aqueous solution. Previous studies of fibrinogen adoption onto various surfaces for hemocompatibility evaluation have reported monolayer thickness ranging between 2 to 37 nm, depending on the surface properties, where thickness values above 10 nm indicated an end-on adsorption[64,65]. See, Weber, N., Pesnell, A., Bolikal, D., Zeltinger, J. & Kohn, J. Viscoelastic Properties of Fibrinogen Adsorbed to the Surface of Biomaterials Used in Blood-Contacting Medical Devices. *Langmuir* 23, 3298-3304 (2007), and Doliška, A., Ribitsch, V., Stana Kleinschek, K. & Strnad, S. Viscoelastic properties of fibrinogen adsorbed onto poly(ethylene terephthalate) surfaces by QCM-D. *Carbohydrate Polymers* 93, 246-255 (2013), each of which is incorporated by reference in its entirety.

SWCNT—Fibrinogen Interaction Microscopy.

Figure 5A:
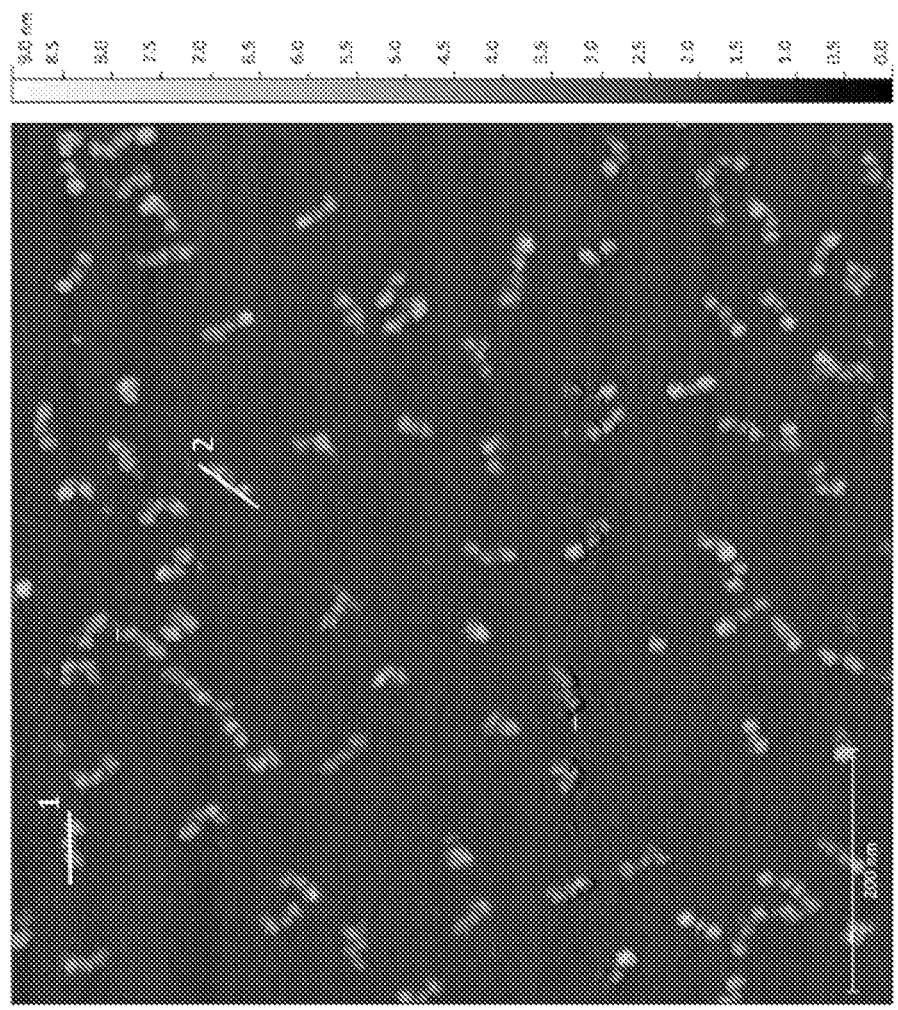
FIGS. 5A-5E show high resolutions microscopy of the SWCNT-fibrinogen interaction.

Fibrinogen molecules were imaged on a mica surface with tapping mode AFM, clearly showing the unique dumbbell structure of the fibrinogen (FIG. 5A). The fibrinogen molecules were scattered uniformly on the surface, randomly orientated, with each molecule being composed of three small spherical nodes. The height profiles along the principle axis of the fibrinogen (labeled as 1 and 2 in FIG. 5A) show characteristic three-peak traces (FIG. 5B, top panel), as expected from the tri-nodule structure of the protein and in agreement with previous findings. See, Yermolenko, I. S., Lishko, V. K., Ugarova, T. P. & Magonov, S. N. High-Resolution Visualization of Fibrinogen Molecules and Fibrin Fibers with Atomic Force Microscopy. *Biomacromolecules* 12, 370-379, doi: 10.1021/bm101122g (2010), which is incorporated by reference in its entirety.

Figure 5B:
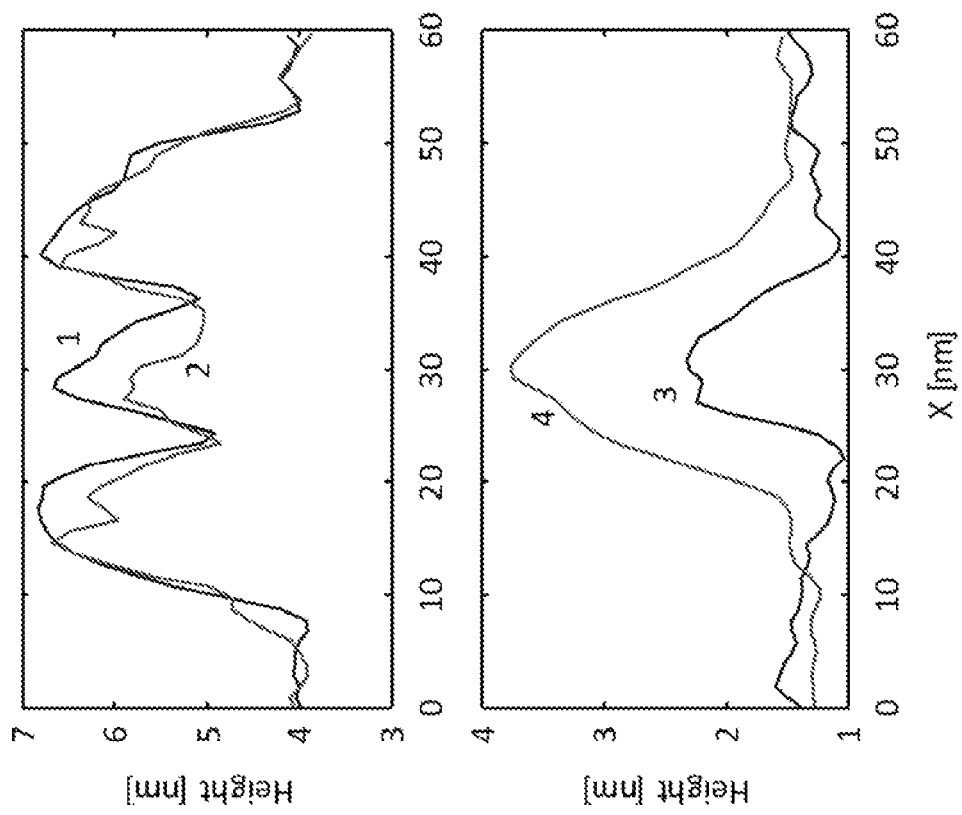
Figure 5C:
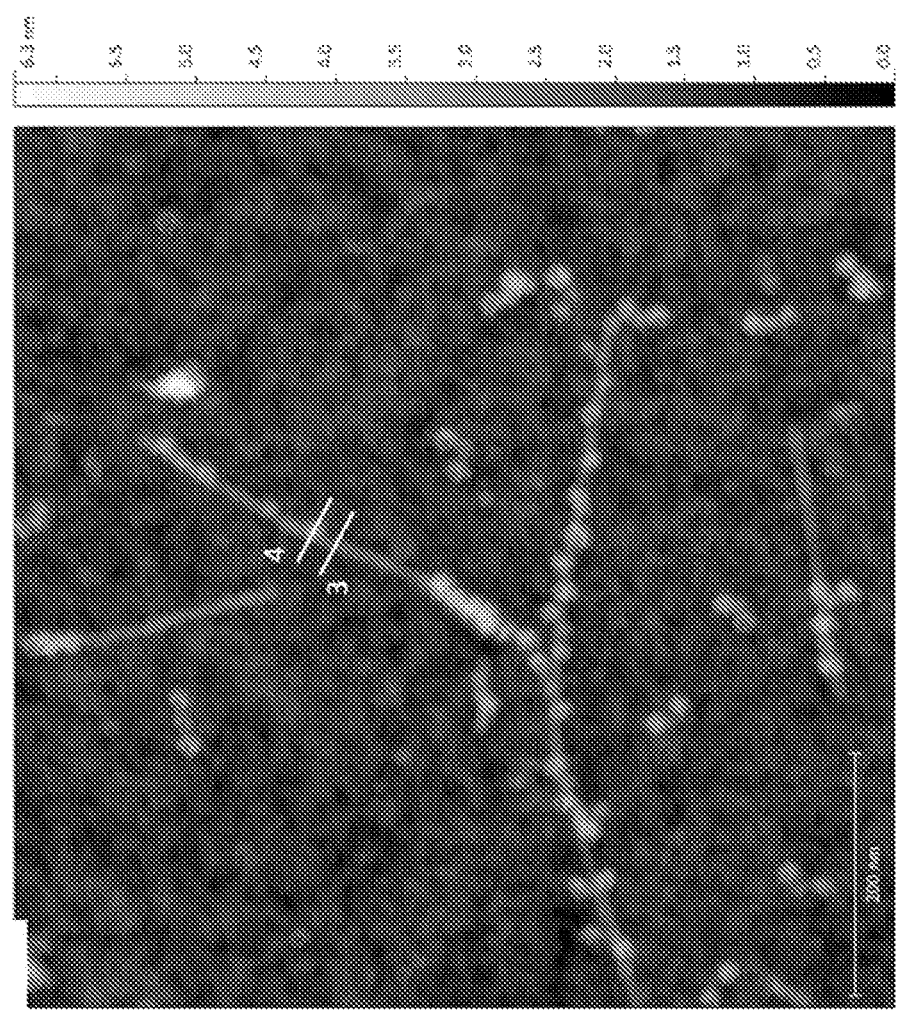
Figure 5D:
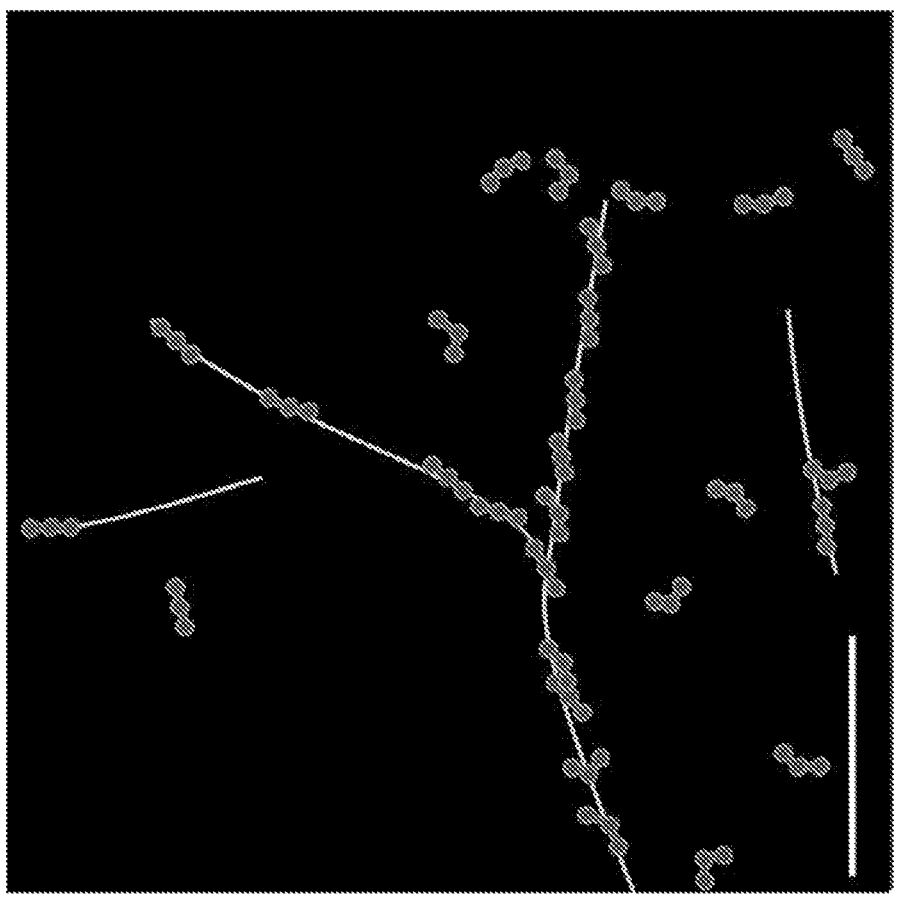

Following incubation with DPPE-PEG(5000)-SWCNT, most of the fibrinogen molecules appear to be bound to SWCNT (FIG. 5C), demonstrating the physical interaction between the two. Comparing the height profiles across a bare SWCNT and across a fibrinogen molecule that is bound to SWCNT (labeled as 3 and 4 in FIG. 5C), the fibrinogen molecule is stacked on top of the nanotube (FIG. 5B, bottom panel). The inter-molecular distance between the adsorbed fibrinogen molecules is 22 nm±20 nm, resulting in an average of 8-9 proteins per SWCNT. Furthermore, the fibrinogen orientation does not appear to be isotropically distributed, but rather the protein molecules seem to align along the axis of the nanotubes. In FIG. 5D, a schematic of the adsorbed fibrinogen constructed from the experimental AFM positions and orientations underscores this observation. This further supports the layer thickness of fibrinogen adsorbed onto SCWNT calculated from the QCM-D data, which indicate a monolayer adsorption of the protein molecules laying horizontally flat (side-on).

Figure 5E:
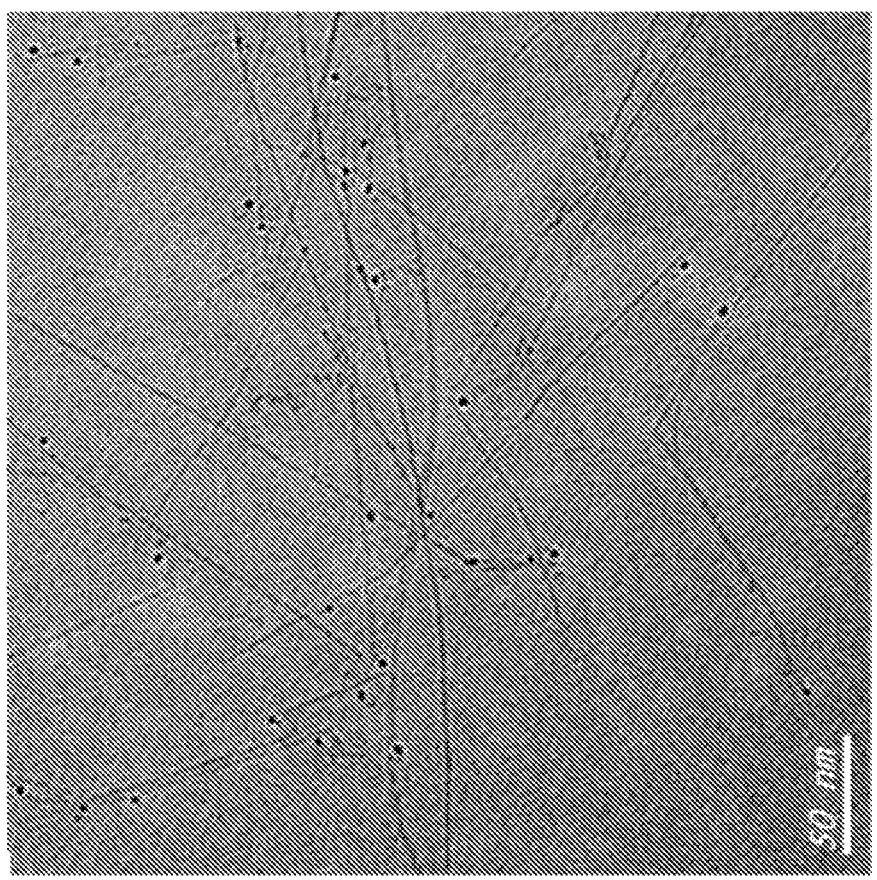

Cryo transmission electron microscopy (cryo-TEM) captures solution samples in their native hydrated environment and avoids artifacts of sample drying. See, Danino, D. Cryo-TEM of soft molecular assemblies. *Current Opinion in Colloid & Interface Science* 17, 316-329 (2012), which is incorporated by reference in its entirety. A sample of DPPE-PEG(5000)-SWCNT incubated with fibrinogen was rapidly frozen in liquid nitrogen and imaged with cryo-TEM. The resulting images show that the SWCNT remain individually suspended in the solution, and no aggregation occurs upon the interaction with the protein (FIG. 5E). This finding additionally confirms that nanoparticle aggregation is not the mechanism of the fibrinogen optical response.

Materials and Methods

DNA and RNA SWCNT Suspension.

Raw HiPCO (Unidym™, 0.8-1.2 nm in diameter with 1 nm mean diameter, and 100 nm-1 µm initial length) were processed by organic-aqueous phase separation followed by drying and homogenizing, as previously described. See, Tvrdy, K. et al. A Kinetic Model for the Deterministic Prediction of Gel-Based Single-Chirality Single-Walled Carbon Nanotube Separation. *ACS Nano* 7, 1779-1789, doi:10.1021/nn305939k (2013), which is incorporated by reference in its entirety. 2 mg of DNA or RNA (Integrated DNA Technologies, Inc.) were added to 1 mg of SWCNT in 1 ml of 0.1 M sodium chloride solution, and sonicated while in an ice bath with 3 mm probe tip (Cole Parmer) for 40 minutes at a power of 4 W. Subsequently, samples were bench-top centrifuged (Eppendorf) for 180 min at 16,100 RCF. The top 80% of the supernatant was carefully collected for further experimenting and the pellet was discarded. Successful suspensions were validated by recording their UV-visible-nIR absorption spectra (Shimadzu UV-3101PC).

Single-stranded DNA sequences used in this study were $(GT)_{15}$ (SEQ ID NO: 1), $(AT)_{30}$ (SEQ ID NO: 3), $(GC)_{30}$ (SEQ ID NO: 4), $(AT)_{15}$ (SEQ ID NO: 5), $(AAAT)_7$ (SEQ ID NO: 6), $(ATTT)_7$ (SEQ ID NO: 7), $(GGGT)_7$ (SEQ ID NO: 8), $(GTTT)_7$ (SEQ ID NO: 9), and the single-stranded RNA sequence used was $(GU)_{15}$ (SEQ ID NO: 2).

Phospholipid—PEG SWCNT Suspension.

SWCNT were first suspended in sodium cholate (SC), which was later removed by dialysis in the presence of phospholipid-poly(ethylene glycol) (phospholipid-PEG, Avanti Polar Lipids) as previously published. See, Zhang, J. et al. Molecular recognition using corona phase complexes made of synthetic polymers adsorbed on carbon nanotubes. *Nat Nano* 8, 959-968 (2013), which is incorporated by reference in its entirety. Briefly, 40 mg of SWCNT was added to 2 wt % sodium cholate solution to a final SWCNT concentration of 1 mg ml$^{-1}$ and was bath sonicated (Branson 2510) for 10 minutes, followed by 6 mm probe tip sonication for 60 min at a power of 12 W while in an ice bath. The resulting dark solution was ultracentrifuged in a SW32 Ti rotor (Beckman Coulter) at 150,000 RCF for 4 hours to remove SWCNT aggregates and impurities. The top 80% of the supernatant was carefully collected for further experimenting and the pellet was discarded (see FIG. 13 for scanning electron microscopy image of the SC-SWCNT suspension). The mean nanotube length following the initial processing was 550 nm.

A 5 mg ml$^{-1}$ solution of phospholipid-PEG in water was bath sonicated for 5 minutes to ensure complete dissolution. The phospholipid-PEG was diluted to a final concentration of 2 mg ml$^{-1}$ in 40 mg L$^{-1}$ of SC-SWCNT suspension and the mixture was dialyzed using 1 kDa molecular weight cutoff (MWCO) dialysis cartridge against water for a period of 4-5 days with multiple water changes to ensure the complete removal of SC from the SWCNT surface, allowing for the adsorption of the phospholipid-PEG instead.

Successful suspensions were validated by recording their UV-visible-nIR absorption spectra (Shimadzu UV-3101PC) in a 1 cm path length quartz cuvette (Starma). The absorption spectra showed a redshift relative to the initial SC-SWCNT suspension (FIG. 14), indicating the surfactant exchange. See, Welsher, K. et al. A route to brightly fluorescent carbon nanotubes for near-infrared imaging in mice. *Nat Nano* 4, 773-780 (2009), which is incorporated by reference in its entirety.

Phospholipid-PEG used in this study were DPPE-PEG (5000), DMPE-PEG(5000), DSPE-PEG(5000), DSPE-PEG (2000), DSPE-PEG(2000)-Cyanur, DSPE-PEG(2000)-CA, DSPE-PEG(2000)-Maleimide, DSPE-PEG(2000)-PDP, DSPE-PEG(2000)-Amine, DSPE-PEG(2000)-Biotin, and DSPE-PEG(350), where DPPE, DMPE, and DSPE stand for dipalmitoyl-, dimyristoyl-, and distearoyl-phosphatidyletanolamine, respectively, CA denotes carboxylic acid, and PDP denotes 3-(2-Pyridyldithio)-propionyl (see FIG. 1A). The number in parentheses is the molecular weight of the PEG chain in Daltons.

High Throughput nIR Photoluminescence Screening.

Human proteins were purchased from Sigma-Aldrich (USA) and were handled according to the supplier instructions. SWCNT suspensions were diluted in phosphate buffered saline (PBS) to 1 mg L$^{-1}$ concentration (0.036 absorption at 632 nm) and aliquots were added to a 96-well plate followed by the addition of 2 vol % of the test protein analytes to a final protein concentration of 2 μg ml$^{-1}$. Following 1 hour incubation on a tabletop orbital shaker, the fluorescent spectra of the SWCNT were recorded using a custom made nIR microscope array. Briefly, the 96-well plate was placed on top of a motorized stage of a Zeiss AxioVision inverted microscope, and the samples were excited by a 785 nm photodiode laser (B&W Tek Inc.) with 80 mW at the sample plane focused by 20× objective for 10 seconds exposure time. The resulting fluorescent light was collected by a coupled nitrogen-cooled Princeton Instruments InGaAs 1D detector through a PI Acton SP2500 spectrometer (FIGS. 15A-15B).

For testing the fluorescence response in serum, the SWCNT suspension was diluted in fetal bovine serum (FBS, 10 vol % in PBS) to 5 mg L$^{-1}$ concentration. Samples of 100 μl fibrinogen solution in PBS were added to 100 μl of SWCNT in FBS, in a 96-well plate, to a final protein concentration of 0.05, 0.5, and 5 mg ml$^{-1}$. Following 1 hour incubation, the fluorescent spectra of the SWCNT were recorded using the custom made nIR microscope array, as described above.

Excitation Emission Profile.

A white light source coupled to a monochromator was used for the excitation of SWCNT samples that were placed on the stage of the nIR array described above (FIG. 15A). The corresponding fluorescence of the sample was collected for excitation wavelength range of 400 nm-800 nm in 5 nm steps with 90 seconds exposure time.

Zeta Potential.

Samples were measured in a zeta potential analyzer (Zeta PALS, Brookhaven Instruments Corporation) with 10 runs of 20 cycles each, following one hour incubation. All samples were kept in PBS at pH 7.4.

Circular Dichroism.

Samples were analyzed, following one hour incubation, in a circular dichroism spectrometer (Aviv Model 202) in the wavelength range of 190-260 nm in 1 nm intervals, using a 1 mm path length quartz cuvette (Hellma). Signal from a reference sample of the PBS buffer was subtracted from the results.

Raman Spectroscopy.

Raman spectra were acquired with a confocal Raman spectrometer HR-800 (Horiba J Y) using a 633 nm laser source focused with a 10× objective on the sample plane. Light was collected for 10 seconds with 5 accumulations. Samples of 300 μl fibrinogen and SWCNT in PBS were measured in a 96-well plate on top of the microscope stage, following one hour incubation.

Continuous Fluorescent Emission Monitoring.

Fluorescent emission was collected using the custom made nIR microscope array as described above, with continuous laser excitation of a sample within a 96-well plate, and spectra acquisition every 2 seconds. The fibrinogen was added to the SWCNT solution while on the microscope stage during a 10 seconds break in laser illumination utilizing the microscope port shutter. The shutter was opened immediately after analyte addition enabling laser excitation resumption.

Immobilized Sensors Fluorescent Monitoring.

Agarose solution (0.2 wt % in water) was heated on top of a hot stirring plate until completely dissolved. The resulting clear solution was allowed to cool for 10 minutes, following which 50 µl aliquots were cast into the wells of a 96-well plate which was kept in a humidified environment for 30 minutes for the solution to gel. SWCNT solution (20 µl of 20 mg L$^{-1}$) was spotted on top of each gel and the plate was placed in a humidified incubator at 37° C. for 30 minutes to allow for the incorporation of the SWCNT within the top layer of the agarose gel that was partially melted. Subsequently, the gels were washed with PBS to remove any unbound materials, and the well plate was kept in a humidified environment at room temperature for additional 30 minutes for cooling and equilibrating before testing.

The fluorescent emission of the immobilized SWCNT on top of the agarose hydrogel was analyzed using a custom made portable nIR detector. Briefly, high power 565 nm light-emitting diode (LED) was focused on the sample, and the emitted fluorescence was collected by a single channel InGaAs detector (Thorlabs) through a 900 nm long pass dichroic mirror, followed by a 1050 nm short pass filter, and a 950 nm long pass filter (FIG. 15B), which isolated the fluorescent emission of the (6,5) SWCNT chirality.

2-Dimensional nIR Fluorescence Microscopy.

Single SWCNT fluorescence data were collected by a Zeiss AxioVision inverted microscope coupled to a nitrogen-cooled InGaAs 2D detector (Princeton Instruments), with 250 mW, 785 nm, laser excitation (Invictus™, Kaiser Optical Systems), through 100× objective (Zeiss, Apochromat, oil immersion). For surface immobilization of single SWCNT, a droplet of 50 µl of 1 mg L$^{-1}$ SWCNT solution was deposited on a microscope slide and left to dry. Subsequently, the slide was extensively washed with PBS to remove any unbound nanotubes. The slide was placed on top of the microscope stage and imaged continuously with 1 second acquisition time. Fibrinogen was added by carefully dropping 20 µl of 0.1 mg ml$^{-1}$ on top of the glass slide, without changing the imaging focal plane.

Quartz Crystal Microbalance with Dissipation.

Quartz crystal microbalance with dissipation (QCM-D) measurements were conducted with a Q-Sense E4 instrument (Q-Sense, Sweden) on a gold coated quartz crystal substrate mounted within a flow module. Both frequency and dissipation responses of 6 overtones of the crystal were monitored throughout the experiment. All the experiments were conducted at a fixed temperature of 25° C. The crystal was first equilibrated under continuous flow of PBS (150 µl min$^{-1}$) before introducing the SWCNT suspension (5 mg L$^{-1}$ in PBS, 150 µl min$^{-1}$), which was then allowed to adsorb under no flow. Afterwards, the flow cell was washed with PBS to remove unbound material. Subsequently, the protein solution (0.1 mg ml$^{-1}$ in PBS, 150 µl min$^{-1}$) was introduced into the flow chamber, followed by PBS wash. In a control experiment, only the protein solution was introduced into the flow cell and washed with PBS afterwards. Owing to the large dissipation response, indicating that the adsorbed layers do not behave as rigid materials (see, Hillman, A. R. in *Encyclopedia of Electrochemistry* (Wiley-VCH Verlag GmbH & Co. KGaA, 2007), which is incorporated by reference in its entirety), the data were fitted by the viscoelastic-Voigt model for the SWCNT and the protein layers (see, Voinova, M. V., Rodahl, M., Jonson, M. & Kasemo, B. Viscoelastic Acoustic Response of Layered Polymer Films at Fluid-Solid Interfaces: Continuum Mechanics Approach. *Physica Scripta* 59, 391 (1999), which is incorporated by reference in its entirety) in two steps with the QTools software (Q-Sense, Sweden), in order to calculate the layers' thickness over time. The density of the SWCNT layer was estimated as 1.6 g cm$^{-3}$ according to the manufacture (Unidym™), whereas the density of the protein layer (see, Hook, F. et al. A comparative study of protein adsorption on titanium oxide surfaces using in situ ellipsometry, optical waveguide lightmode spectroscopy, and quartz crystal microbalance/dissipation. *Colloids and Surfaces B: Biointerfaces* 24, 155-170 (2002), which is incorporated by reference in its entirety) was taken to be 1.3 g cm$^{-3}$.

AFM.

Silicon wafers were washed by isopropanol and water, and were blown dry by a nitrogen gun. Samples of 147 µl of 1 mg L$^{-1}$ SWCNT were mixed with 3 µl of 0.1 mg ml$^{-1}$ fibrinogen in PBS, and following one hour incubation, 40 µl of the mixture was pipetted onto the wafer. In addition, 40 µl of 0.1 mg ml$^{-1}$ fibrinogen in PBS was pipetted on top of a freshly cleaved mica (Grade V-1 Muscovite, SPI Supplies, Structure Probe, Inc.). The substrates were allowed to dry for 10 minutes in the fume hood and were washed again with water before imaging with Asylum Research MFP-3D atomic force microscope (AFM) in tapping mode.

Hydrophobicity Maps.

The three dimensional structure of the proteins was visualized with Pymol Molecular Graphics System software (Version 1.7.1.3, Schrodinger LLC), using the corresponding protein data bank (PDB) files. The protein panel includes the following proteins: albumin, IgG, fibrinogen, α1-antitrypsin, Transferrin, Haptoglobin, α2-macroglobolin, IgA, IgM, α2-acid-glycoprotein, apopoliprotein A-I, insulin, human chorionic gonadotropin (hCG), and C-reactive protein (CRP). The corresponding protein data bank (PDB) files used for the visualization of the hydrophobicity maps are found in the following references: see, Schönfeld, D. L., Ravelli, R. B. G., Mueller, U. & Skerra, A. The 1.8-Å Crystal Structure of α1-Acid Glycoprotein (Orosomucoid) Solved by UV RIP Reveals the Broad Drug-Binding Activity of This Human Plasma Lipocalin. *Journal of Molecular Biology* 384, 393-405 (2008), Sugio, S., Kashima, A., Mochizuki, S., Noda, M. & Kobayashi, K. Crystal structure of human serum albumin at 2.5 Å resolution. *Protein Engineering* 12, 439-446, doi:10.1093/protein/12.6.439 (1999), Saphire, E. O. et al. Crystal Structure of a Neutralizing Human IgG Against HIV-1: A Template for Vaccine Design. *Science* 293, 1155-1159, doi:10.1126/science.1061692 (2001), Kollman, J. M., Pandi, L., Sawaya, M. R., Riley, M. & Doolittle, R. F. Crystal Structure of Human Fibrinogen. *Biochemistry* 48, 3877-3886, doi:10.1021/bi802205g (2009), Hyun Kyu, S., Kee Nyung, L., Ki-Sun, K., Myeong-Hee, Y. & Se Won, S. Crystal structure of an uncleaved α1-antitrypsin reveals the conformation of its inhibitory reactive loop. *FEBS Letters* 377, 150-154 (1995), Yang, N., Zhang, H., Wang, M., Hao, Q. & Sun, H. Iron and bismuth bound human serum transferrin reveals a partially-opened conformation in the N-lobe. *Sci. Rep.* 2 (2012), Andersen, C. B. F. et al. Structure of the haptoglobin-haemoglobin complex. *Nature* 489, 456-459 (2012), Doan, N. & Gettins, P. G. W. Human α2-macroglobulin is composed of multiple domains, as predicted by homology with complement component C3. *Biochem J* 407, 23-30, doi:10.1042/bj20070764 (2007), Bonner, A., Furtado, P. B., Almogren, A., Kerr, M. A. & Perkins, S. J. Implications of the Near-Planar Solution Structure of Human Myeloma Dimeric IgA1 for Mucosal Immunity and IgA Nephropathy. *The Journal of Immunology* 180, 1008-1018, doi:10.4049/jimmunol.180.2.1008 (2008), Perkins, S. J., Nealis, A. S., Sutton, B. J. & Feinstein, A. Solution structure of human and mouse immunoglobulin M by synchrotron X-ray scattering and molecular graphics modelling: A possible mechanism for complement activation. *Journal of Molecular Biology* 221, 1345-1366 (1991), Ajees, A. A., Anantharamaiah, G. M., Mishra, V. K., Hussain, M. M. & Murthy, H. M. K. Crystal structure of human apolipoprotein A-I: Insights into its protective effect against cardiovascular diseases. *Proceedings of the National Academy of Sciences of the United States of America* 103, 2126-2131, doi:10.1073/pnas.0506877103 (2006), Fávero-Retto, M. P., Palmieri, L. C., Souza, T. A. C. B., Almeida, F. C. L. & Lima, L. M. T. R. Structural meta-analysis of regular human insulin in pharmaceutical formulations. *European Journal of Pharmaceutics and Biopharmaceutics* 85, 1112-1121 (2013), Lapthorn, A. J. et al. Crystal structure of human chorionic gonadotropin. *Nature* 369, 455-461 (1994), and Shrive, A. K. et al. Three dimensional structure of human C-reactive protein. *Nature Structural & Molecular Biology* 3, 346-354 (1996), each of which is incorporated by reference in its entirety.

The hydrophobicity was visualized by a color map from white (hydrophilic) to red (hydrophobic), according to a normalized scale. See, Eisenberg, D., Schwarz, E., Komaromy, M. & Wall, R. Analysis of membrane and surface protein sequences with the hydrophobic moment plot. *Journal of Molecular Biology* 179, 125-142 (1984), which is incorporated by reference in its entirety. The hydrophobic surface area was obtained by calculating the solvent accessible surface area of the hydrophobic amino acids relative to the total area.

Cryo-TEM.

A sample droplet (4 µl) was placed on top of a support film (lacey former/carbon on 200 mesh grid), which was then mounted on a Gatan 626 cryo-holder. The specimen was cooled by liquid nitrogen and was subsequently loaded onto a high-resolution analytical Cryo-Transmission Electron Microscope (Cryo-TEM, JEOL 2100 FRG) for imaging, operating at acceleration voltage of 200 kV, with magnification range between 10,000 and 60,000. Images were recorded with a Gatan 2k×2k UltraScan CCD camera.

Scanning Electron Microscopy (SEM).

A droplet of 20 µl of 10 mg $L^{-1}$ SC-SWCNT was placed on top of an aluminum slab and was left in a fume hood to dry overnight. The sample was imaged with JEOL 6700F Scanning Electron Microscope, using 5 kV accelerating voltage and the secondary electrons detector.

II. Insulin Recognition

Insulin is a peptide hormone, synthesized and secreted by the pancreas, responsible for stimulating glucose uptake from the blood and the synthesis of lipids, as well as inhibiting proteins, glycogen, and lipids breakdown, glucose generation, and ketone bodies production. See Sonksen, P.; Sonksen, J., Insulin: understanding its action in health and disease. *British Journal of Anaesthesia* 2000, 85 (1), 69-79, which is incorporated by reference in its entirety. Insulin deficiency and/or insulin resistant characterize the chronic disease diabetes mellitus, of which more than 400 million people suffer world-wide. Pankaj, M., Diabetes Beyond Insulin: Review of New Drugs for Treatment of Diabetes Mellitus. *Current Drug Discovery Technologies* 2007, 4 (1), 39-47, and Global report on diabetes. *World Health Organization, Geneva* 2016, each of which is incorporated by reference in its entirety. In type I disease, the body cannot produce insulin due to a complete destruction of the insulin producing cells, and patients must rely on external sources of insulin. See, Daneman, D., Type 1 diabetes. *The Lancet* 2006, 367 (9513), 847-858, which is incorporated by reference in its entirety. The best course of treatment for glycemic control in this case includes a continuous glucose monitoring device and an insulin infusion pump, where the ultimate goal is a closed-loop artificial pancreas system. See, Choudhary, P.; Ramasamy, S.; Green, L.; Gallen, G.; Pender, S.; Brackenridge, A.; Amiel, S. A.; Pickup, J. C., Real-Time Continuous Glucose Monitoring Significantly Reduces Severe Hypoglycemia in Hypoglycemia-Unaware Patients With Type 1 Diabetes. *Diabetes Care* 2013, 36 (12), 4160-4162, Jacobi, J.; Bircher, N.; Krinsley, J.; Agus, M.; Braithwaite, S. S.; Deutschman, C.; Freire, A. X.; Geehan, D.; Kohl, B.; Nasraway, S. A., Guidelines for the use of an insulin infusion for the management of hyperglycemia in critically ill patients. *Critical care medicine* 2012, 40 (12), 3251-3276, Doyle, E. A.; Weinzimer, S. A.; Steffen, A. T.; Ahern, J. A. H.; Vincent, M.; Tamborlane, W. V, A randomized, prospective trial comparing the efficacy of continuous subcutaneous insulin infusion with multiple daily injections using insulin glargine. *Diabetes Care* 2004, 27 (7), 1554-1558, Steil, G. M.; Panteleon, A. E.; Rebrin, K., Closed-loop insulin delivery—the path to physiological glucose control. *Advanced Drug Delivery Reviews* 2004, 56 (2), 125-144, Breton, M.; Farret, A.; Bruttomesso, D.; Anderson, S.; Magni, L.; Patek, S.; Dalla Man, C.; Place, J.; Demartini, S.; Del Favero, S., Fully integrated artificial pancreas in type 1 diabetes. *Diabetes* 2012, 61 (9), 2230-2237, and Kovatchev, B.; Tamborlane, W. V.; Cefalu, W. T.; Cobelli, C., The artificial pancreas in 2016: a digital treatment ecosystem for diabetes. *Diabetes Care* 2016, 39 (7), 1123-1126, each of which is incorporated by reference in its entirety.

Due to the fear of hypoglycemia occurrence, insulin dosing is on the conservative side and treatment protocols tend to under-dose insulin drugs. See, Maynard, G.; Wesorick, D. H.; O'Malley, C.; Inzucchi, S. E.; Force, S. o. H. M. G. C. T., Subcutaneous insulin order sets and protocols: effective design and implementation strategies. *J Hosp Med* 2008, 3 (5 Suppl), 29-41, which is incorporated by reference in its entirety. One of the reasons is the lack of information regarding the circulating insulin already present in blood before the administration of external source of insulin. See, Bisker, G.; Iverson, N. M.; Ahn, J.; Strano*, M. S., A Pharmacokinetic Model of a Tissue Implantable Insulin Sensor. *Advanced Healthcare Materials* 2015, 4 (1), 87-97, which is incorporated by reference in its entirety. Unlike glucose, whose blood levels can be monitored continuously or on demand fairly easily by the patient, insulin levels are not as accessible and require a blood test and laboratory equipment for analysis. See, Newman, J. D.; Turner, A. P., Home blood glucose biosensors: a commercial perspective. *Biosensors and bioelectronics* 2005, 20 (12), 2435-2453, and Katz, A.; Nambi, S. S.; Mather, K.; Baron, A. D.; Follmann, D. A.; Sullivan, G.; Quon, M. J., Quantitative Insulin Sensitivity Check Index: A Simple, Accurate Method for Assessing Insulin Sensitivity In Humans. *The Journal of Clinical Endocrinology & Metabolism* 2000, 85 (7), 2402-2410, each of which is incorporated by reference in its entirety. This gives rise to the need for new technological solutions for measuring insulin concentrations in blood, aiming for better glycemic control, as well as improved algorithm for a closed-loop system.

One of the most prominent bottlenecks in detecting and monitoring bio-analytes in vivo is the actual molecular recognition of the target. See, Iqbal, S. S.; Mayo, M. W.; Bruno, J. G.; Bronk, B. V.; Batt, C. A.; Chambers, J. P., A review of molecular recognition technologies for detection of biological threat agents. *Biosensors and bioelectronics* 2000, 15 (11), 549-578, Rebek, J., Molecular recognition with model systems. *Angewandte Chemie International Edition in English* 1990, 29 (3), 245-255, and Brooijmans, N.; Kuntz, I. D., Molecular recognition and docking algorithms. *Annual review of biophysics and biomolecular structure*

2003, 32 (1), 335-373, each of which is incorporated by reference in its entirety. In the case of insulin, nature has provided us with some natural recognizing options, including the insulin receptor, insulin antibody, insulin binding aptamer, and insulin binding peptide. The insulin receptor (IR) is a transmembrane tyrosine kinase receptor which is composed of two α-subunits and two β-subunits. See, Ullrich, A.; Bell, J. R.; Chen, E. Y.; Herrera, R.; Petruzzelli, L. M.; Dull, T. J.; Gray, A.; Coussens, L.; Liao, Y. C.; Tsubokawa, M.; et al., Human insulin receptor and its relationship to the tyrosine kinase family of oncogenes. *Nature* 1985, 313 (6005), 756-61, which is incorporated by reference in its entirety. It is activated upon the binding of insulin to the IR's α-subunit, leading to a cascade of biochemical events that result in multiple effects including the promotion of glucose influx. See, Kasuga, M.; Karlsson, F. A.; Kahn, C. R., Insulin stimulates the phosphorylation of the 95,000-dalton subunit of its own receptor. *Science* 1982, 215 (4529), 185-7, which is incorporated by reference in its entirety. Insulin antibodies, on the other hand, should not be found in the blood of healthy individuals and their production is often the result of exogenous insulin treatment. See, Schernthaner, G., Immunogenicity and allergenic potential of animal and human insulins. *Diabetes Care* 1993, 16 *Suppl* 3, 155-65, which is incorporated by reference in its entirety. The presence of such antibodies may cause insulin resistance or hypoglycemia and in other cases can indicate an early diabetic stage or allergy to insulin. See, Hattori, N.; Duhita, M. R.; Mukai, A.; Matsueda, M.; Shimatsu, A., Development of insulin antibodies and changes in titers over a long-term period in patients with type 2 diabetes. *Clin Chim Acta* 2014, 433, 135-8, Yalow, R. S.; Berson, S. A., Plasma Insulin Concentrations in Nondiabetic and Early Diabetic Subjects: Determinations by a New Sensitive Immuno-assay Technic. *Diabetes* 1960, 9 (4), 254-260, and Fineberg, S. E.; Kawabata, T. T.; Finco-Kent, D.; Fountaine, R. J.; Finch, G. L.; Krasner, A. S., Immunological responses to exogenous insulin. *Endocr Rev* 2007, 28 (6), 625-52, each of which is incorporated by reference in its entirety. The insulin-binding peptide (IBP) [Cys-Val-Glu-Glu-Ala-Ser (SEQ ID NO: 10)] was designed by translating the complimentary sequence of the gene that codes for the IR binding insulin region, and was shown to interact with the carboxyl terminus of the insulin β-chain. See, Knutson, V. P., Insulin-binding peptide. Design and characterization. *Journal of Biological Chemistry* 1988, 263 (28), 14146-14151, which is incorporated by reference in its entirety. Aptamers, which are oligonucleotide with a unique three-dimensional conformation that allows for strong interactions with a target protein, are usually discovered by in vitro combinatorial evolution (Systematic evolution of ligands by exponential enrichment, or SELEX). See, Stoltenburg, R.; Reinemann, C.; Strehlitz, B., SELEX—a (r) evolutionary method to generate high-affinity nucleic acid ligands. *Biomolecular engineering* 2007, 24 (4), 381-403, which is incorporated by reference in its entirety. A natural aptamer for insulin was found in the insulin gene promoter region that regulates insulin transcription (see Connor, A. C.; Frederick, K. A.; Morgan, E. J.; McGown, L. B., Insulin Capture by an Insulin-Linked Polymorphic Region G-Quadruplex DNA Oligonucleotide. *Journal of the American Chemical Society* 2006, 128, 4986-4991, which is incorporated by reference in its entirety), suggesting that insulin regulated its own transcription. This region, referred to as the insulin-linked polymorphic region (ILPR) has repeats of a G-rich sequence that was shown to have strong affinity towards the insulin protein. Based on this finding, further in vitro selection process has led to the discovery of additional insulin aptamers with even stronger affinity. See Yoshida, W.; Mochizuki, E.; Takase, M.; Hasegawa, H.; Morita, Y.; Yamazaki, H.; Sode, K.; Ikebukuro, K., Selection of DNA aptamers against insulin and construction of an aptameric enzyme subunit for insulin sensing. *Biosens Bioelectron* 2009, 24, 1116-1120, which is incorporated by reference in its entirety.

The main shortcomings of natural systems include their high cost and limited lifetime. See, Vlatakis, G.; Andersson, L. I.; Müller, R.; Mosbach, K., Drug assay using antibody mimics made by molecular imprinting. 1993, Wulff, G., Molecular imprinting in cross-linked materials with the aid of molecular templates—a way towards artificial antibodies. *Angewandte Chemie International Edition in English* 1995, 34 (17), 1812-1832, and Mosbach, K.; Ramström, O., The emerging technique of molecular imprinting and its future impact of biotechnology. *Bio/technology* 1996, 14 (2), 163-170, each of which is incorporated by reference in its entirety. Synthetic systems[31], on the other hand, can benefit from both chemical and thermal stability, enabling detection in harsh environments, including in vivo. See, Schirhagl, R.; Latif, U.; Podlipna, D.; Blumenstock, H.; Dickert, F. L., Natural and Biomimetic Materials for the Detection of Insulin. *Analytical Chemistry* 2012, 84 (9), 3908-3913, and Iverson, N. M.; Barone, P. W.; Shandell, M.; Trudel, L. J.; Sen, S.; Sen, F.; Ivanov, V.; Atolia, E.; Farias, E.; McNicholas, T. P.; Reuel, N.; Parry, N. M. A.; Wogan, G. N.; Strano, M. S., In vivo biosensing via tissue-localizable near-infrared-fluorescent single-walled carbon nanotubes. *Nat Nano* 2013, 8 (11), 873-880, each of which is incorporated by reference in its entirety. Recently, the concept of corona phase molecular recognition, or CoPhMoRe has been introduced. See, Zhang, J.; Landry, M. P.; Barone, P. W.; Kim, J.-H.; Lin, S.; Ulissi, Z. W.; Lin, D.; Mu, B.; Boghossian, A. A.; Hilmer, A. J.; Rwei, A.; Hinckley, A. C.; Kruss, S.; Shandell, M. A.; Nair, N.; Blake, S.; Sen, F.; Sen, S.; Croy, R. G.; Li, D.; Yum, K.; Ahn, J.-H.; Jin, H.; Heller, D. A.; Essigmann, J. M.; Blankschtein, D.; Strano, M. S., Molecular recognition using corona phase complexes made of synthetic polymers adsorbed on carbon nanotubes. *Nature Nanotechnology* 2013, 8 (12), 959-968, and Landry, M.; Kruss, S.; Nelson, J.; Bisker, G.; Iverson, N.; Reuel, N.; Strano, M., Experimental Tools to Study Molecular Recognition within the Nanoparticle Corona. Sensors 2014, 14 (9), 16196-16211, each of which is incorporated by reference in its entirety. In this approach, a hetero-polymer is used to suspend fluorescent nanoparticles, such that its pinned configuration around the nanoparticles, referred to as the corona phase, enables the selective recognition of a target analyte. Single-walled carbon nanotubes (SWNTs) were used as the underlying nanoparticles owing to their high photo-stability, lack of photo-bleaching, and bright fluorescent emission in the near-infrared (nIR) part of the spectrum, which overlaps with the tissue transparency window. See, Barone, P. W.; Baik, S.; Heller, D. A.; Strano, M. S., Near-infrared optical sensors based on single-walled carbon nanotubes. *Nat Mater* 2005, 4 (1), 86-U16, Boghossian, A. A.; Zhang, J. Q.; Barone, P. W.; Reuel, N. F.; Kim, J. H.; Heller, D. A.; Ahn, J. H.; Hilmer, A. J.; Rwei, A.; Arkalgud, J. R.; Zhang, C. T.; Strano, M. S., Near-Infrared Fluorescent Sensors based on Single-Walled Carbon Nanotubes for Life Sciences Applications. *Chemsuschem* 2011, 4 (7), 848-863, Kruss, S.; Hilmer, A. J.; Zhang, J.; Reuel, N. F.; Mu, B.; Strano, M. S., Carbon nanotubes as optical biomedical sensors. *Advanced Drug Delivery Reviews* 2013, 65 (15), 1933-1950, and Iverson, N. M.; Bisker, G.; Farias, E.; Ivanov, V.; Ahn, J.; Wogan, G. N.; Strano, M. S., Quantitative Tissue Spectroscopy of Near Infrared Fluorescent Nanosensor Implants. *Journal of Biomedical Nanotechnology* 2016, 12 (5), 1035-1047, each of which is incorporated by reference in its entirety. Further, SWNT can be rendered bio-compatible and thus can be used for in vivo applications. See, Giraldo, J. P.; Landry, M. P.; Faltermeier, S. M.; McNicholas, T. P.; Iverson, N. M.; Boghossian, A. A.; Reuel, N. F.; Hilmer, A. J.; Sen, F.; Brew, J. A.; Strano, M. S., Plant nanobionics approach to augment photosynthesis and biochemical sensing. *Nat Mater* 2014, 13 (4), 400-408, and Oliveira, S. F.; Bisker, G.; Bakh, N. A.; Gibbs, S. L.; Landry, M. P.; Strano, M. S., Protein functionalized carbon nanomaterials for biomedical applications. *Carbon* 2015, 95, 767-779, each of which is incorporated by reference in its entirety.

CoPhMoRe was first demonstrated for small molecules detection such as, riboflavin, L-thyroxine, estradiol, and dopamine. See, Zhang, J.; Landry, M. P.; Barone, P. W.; Kim, J.-H.; Lin, S.; Ulissi, Z. W.; Lin, D.; Mu, B.; Boghossian, A. A.; Hilmer, A. J.; Rwei, A.; Hinckley, A. C.; Kruss, S.; Shandell, M. A.; Nair, N.; Blake, S.; Sen, F.; Sen, S.; Croy, R. G.; Li, D.; Yum, K.; Ahn, J.-H.; Jin, H.; Heller, D. A.; Essigmann, J. M.; Blankschtein, D.; Strano, M. S., Molecular recognition using corona phase complexes made of synthetic polymers adsorbed on carbon nanotubes. *Nature Nanotechnology* 2013, 8 (12), 959-968, and Kruss, S.; Landry, M. P.; Vander Ende, E.; Lima, B. M. A.; Reuel, N. F.; Zhang, J.; Nelson, J.; Mu, B.; Hilmer, A.; Strano, M., Neurotransmitter Detection Using Corona Phase Molecular Recognition on Fluorescent Single-Walled Carbon Nanotube Sensors. *Journal of the American Chemical Society* 2013, 136 (2), 713-724, each of which is incorporated by reference in its entirety. Subsequently, the CoPhMoRe concept was extended to larger biological macromolecules, and the detection of the protein fibrinogen was successfully demonstrated. See, Bisker, G.; Dong, J.; Park, H. D.; Iverson, N. M.; Ahn, J.; Nelson, J. T.; Landry, M. P.; Kruss, S.; Strano, M. S., Protein-targeted corona phase molecular recognition. *Nature Communications* 2016, 7, which is incorporated by reference in its entirety. Selective CoPhMoRe phases have been discovered in a high-throughput screening process of testing libraries of wrapping polymers against libraries of analytes. The optical signal of the SWNT enables immediate feedback by monitoring the fluorescent emission, where a binding event of an analyte to the corona phase is translated to a modulation of the fluorescent intensity or a shift in the peak emission wavelength. See, Landry, M.; Kruss, S.; Nelson, J.; Bisker, G.; Iverson, N.; Reuel, N.; Strano, M., Experimental Tools to Study Molecular Recognition within the Nanoparticle Corona. *Sensors* 2014, 14 (9), 16196-16211, which is incorporated by reference in its entirety. The interaction between a target molecule and the SWNT at the surface of the corona phase is extremely complex and is affected by multiple factors such as the wrapping polymer composition, the nanotube chirality, the valency of the corona phase, and the redox-potential of the target. See, Landry, M. P.; Vuković, L.; Kruss, S.; Bisker, G.; Landry, A. M.; Islam, S.; Jain, R.; Schulten, K.; Strano, M. S., Comparative Dynamics and Sequence Dependence of DNA and RNA Binding to Single Walled Carbon Nanotubes. *The Journal of Physical Chemistry C* 2015, 119 (18), 10048-10058, Salem, D. P.; Landry, M. P.; Bisker, G.; Ahn, J.; Kruss, S.; Strano, M. S., Chirality dependent corona phase molecular recognition of DNA-wrapped carbon nanotubes. *Carbon* 2016, 97, 147-153, Nelson, J. T.; Kim, S.; Reuel, N. F.; Salem, D. P.; Bisker, G.; Landry, M. P.; Kruss, S.; Barone, P. W.; Kwak, S.; Strano, M. S., Mechanism of Immobilized Protein A Binding to Immunoglobulin G on Nanosensor Array Surfaces. *Analytical Chemistry* 2015, 87 (16), 8186-8193, and Polo, E.; Kruss, S., Impact of Redox-Active Molecules on the Fluorescence of Polymer-Wrapped Carbon Nanotubes. *The Journal of Physical Chemistry C* 2016, 120 (5), 3061-3070, each of which is incorporated by reference in its entirety. The inverse problem of CoPhMoRe design for a given target molecules have been addressed theoretically for helically wrapped SWNT (see Bisker, G.; Ahn, J.; Kruss, S.; Ulissi, Z. W.; Salem, D. P.; Strano, M. S., A Mathematical Formulation and Solution of the CoPhMoRe Inverse Problem for Helically Wrapping Polymer Corona Phases on Cylindrical Substrates. *The Journal of Physical Chemistry C* 2015, 119 (24), 13876-13886, which is incorporated by reference in its entirety), whereas experimental demonstration will be the subject of a future research.

In this work an extended protein CoPhMoRe screen was implemented with a library of PEGylated lipids wrappings aiming for insulin recognition. The new library of nanotube suspensions were screened against a protein panel, constructed from abundant and clinically significant proteins (see, Bisker, G.; Dong, J.; Park, H. D.; Iverson, N. M.; Ahn, J.; Nelson, J. T.; Landry, M. P.; Kruss, S.; Strano, M. S., Protein-targeted corona phase molecular recognition. *Nature Communications* 2016, 7, which is incorporated by reference in its entirety) and found a specific C16 PEG2000 Ceramide—SWNT complex that detects insulin with high specificity. With this wrapping, N-palmitoyl-sphingosine-1-{succinyl[methoxyPEG2000]}, the (10,2) chirality shows over 60% decrease in the fluorescence emission intensity upon the interaction with 20 μg/ml insulin. According to isothermal titration calorimetry (ITC) measurements, the insulin has no affinity to the wrapping itself, but rather to its pinned configuration when wrapped around the nanotube. The response is not correlated to the protein molecular weight, hydrophobicity, or isoelectric point. Further, the insulin response is not correlated to the solvatochromic characterization of the fluorescent emission of the nanotubes with the various corona phases, however, larger end groups attached to the PEG-chain were shown to hinder the fluorescence response. Testing the insulin sensor against long fragments of its two chains resulted in reduced affinity, whereas shorted peptides were not detected at all, manifesting the specificity of the recognition. Finally, the local insulin concentration can be inferred from the fluorescence response both in buffer and in serum environment, opening the exciting possibility of continuous insulin monitoring in vivo.

SWNT Suspension and Initial Characterization.

HiPCO SWNT were initially suspended with sodium cholate (SC) using direct sonication followed by ultracentrifugation to separate the individually suspended nanotubes from aggregates and other impurities. See Moore, V. C.; Strano, M. S.; Haroz, E. H.; Hauge, R. H.; Smalley, R. E.; Schmidt, J.; Talmon, Y, Individually Suspended Single-Walled Carbon Nanotubes in Various Surfactants. *Nano Lett* 2003, 3 (10), 1379-1382, which is incorporated by reference in its entirety. Subsequently, the SC-SWNT suspensions were mixed with PEGylated-lipids (FIG. 22) and dialyzed against water with multiple water exchange, such that the PEG-lipid derivatives exchanged the nanotube wrapping by adsorbing onto the nanotube surface and replacing the small surfactant molecules. See Welsher, K.; Liu, Z.; Sherlock, S. P.; Robinson, J. T.; Chen, Z.; Daranciang, D.; Dai, H., A route to brightly fluorescent carbon nanotubes for near-infrared imaging in mice. *Nature Nanotechnology* 2009, 4 (11), 773-780, which is incorporated by reference in its entirety. The library of PEGylated-lipids included 18:1 PEG2000-PE, $C_{16}$-PEG2000-Ceramide, 14:0 PEG5000-PE, 14:0 PEG2000-PE, C16 PEG5000-Ceramide, 16:0 PEG2000-PE, 18:0 PEG2000-PE, 18:0 PEG2000 PE-Azide, 18:0 PEG2000 PE-dibenzocyclooctyl (DBCO), 18:0 PEG2000 PE-Cyanur, 18:0 PEG2000 PE-Maleimide, 16:0 PEG5000-PE, where additional PEGylated-lipids were included in the analysis from a previous study, including 18:0 PEG5000-PE, 18:0 PEG2000 PE-carboxylic acid, 18:0 PEG2000 PE-[3-(2-Pyridyldithio)-propionyl] (PDP), 18:0 PEG2000 PE-Amine, and 18:0 PEG2000 PE-Biotin, 18:0 PEG350-PE. PE stands for phosphorylethanolamine, the number adjacent to PEG is its molecular weight in Daltons, and the preceding numbers stand for the ratio between saturated to unsaturated carbon bonds.

Following the dialysis, the suspensions were first characterized by their absorption spectra, where successful suspensions demonstrated distinct absorption peaks ranging from the ultraviolet (UV) to the near-infrared (nIR) (FIG. 23). Further, all the suspension showed bright fluorescence with distinct emission peaks in the nIR (FIG. 18A).

The emission peak wavelengths vary between the various suspension, an effect referred to as a solvatochromism shift, owing to the different dielectric environment experienced by the underlying fluorescent nanoparticle.[50] The semi-empirical functional form that related this shift to the diameter of the nanotube is given by[42]:

$$(E_{11})^2 \Delta E_{11} = -Lk \left[ \frac{2(\varepsilon - 1)}{2\varepsilon + 1} - \frac{2(n^2 - 1)}{2n^2 + 1} \right] \frac{1}{d^4} = \frac{C}{d^4} \quad (11)$$

Where $E_{11}$ is the optical transition energy, $\Delta E_{11}$ is the energy difference between the optical transition of the wrapped-nanotubes and the optical transition of a bare nanotube in air. L is a fluctuation factor, k is a scaling constant, £ is the dielectric constant, n is the refractive index, d is the nanotube diameter, and C is a constant gathering all the parameters corresponding to a specific diameter (chirality).

The solvatochromism shift factor $(E_{11})^2 \Delta E_{11}$, which is the left hand side of Eq. 1 (11), is plotted against $d^{-4}$ in FIG. 18B, where the straight line is a linear fit to the data. The various suspensions are ranked order according to the slope of the fit, C (FIG. 18C).

Protein Library Screening.

The protein library disclosed above was used. Briefly, 14 proteins were selected due to their high abundance or clinical significance in the human blood, including albumin, Immunoglobulin G (IgG), fibrinogen, α 1-antitrypsin, transferrin, haptoglobin, α 2-macroglobulin, IgA, IgM, α 1-acidglycoprotein, apolipoprotein A-I, insulin, human chorionic gonadotropin (hCG), and C-reactive protein (CRP). The fluorescence of the various suspensions at 1 mg/L concentration was measured following 30 minutes of incubation with the proteins at 20 µg/ml in phosphate buffered saline (PBS) followed by the deconvolution of the data to the different chiralities as described in previous studies. See, Zhang, J.; Landry, M. P.; Barone, P. W.; Kim, J.-H.; Lin, S.; Ulissi, Z. W.; Lin, D.; Mu, B.; Boghossian, A. A.; Hilmer, A. J.; Rwei, A.; Hinckley, A. C.; Kruss, S.; Shandell, M. A.; Nair, N.; Blake, S.; Sen, F.; Sen, S.; Croy, R. G.; Li, D.; Yum, K.; Ahn, J.-H.; Jin, H.; Heller, D. A.; Essigmann, J. M.; Blankschtein, D.; Strano, M. S., Molecular recognition using corona phase complexes made of synthetic polymers adsorbed on carbon nanotubes. *Nature Nanotechnology* 2013, 8 (12), 959-968, and Bisker, G.; Dong, J.; Park, H. D.; Iverson, N. M.; Ahn, J.; Nelson, J. T.; Landry, M. P.; Kruss, S.; Strano, M. S., Protein-targeted corona phase molecular recognition. *Nature Communications* 2016, 7, each of which is incorporated by reference in its entirety. The results for the (10,2) chirality are presented in FIG. 19A as a heat-map, with yellow-red color for fluorescence intensity increase, and green-white color for fluorescence intensity decrease. The PEGylated lipids in the heat-map are ranked order according to their response towards insulin. The strongest insulin response (-74%) was observed for the 18:0 PEG (2000)-carboxylic acid wrapping, however, this suspension showed a comparable response to fibrinogen (-79%), and a smaller response to albumin (-24%). The second strongest response was observed for $C_{16}$-PEG(2000 kDa)-Ceramide (-62%), in which case no other protein induced an intensity decrease of over 5%, and only a single protein, apolipoprotein A-I, induced an intensity increase of (+25%). Hence, the $C_{16}$-PEG(2000 kDa)-Ceramide was chosen for further study as an insulin sensor.

Examining the response towards insulin versus the solvatochromism slope, C, from Eq. 1 (11), no correlation is found between these two parameters (FIG. 19B). However, a statistically significant correlation of 0.52 (p<0.05) is found between the insulin response and the molecular weight of the end group attached to the PEG chain. This means that larger end group hinders interaction of the proteins with the nanotube surface and thus prevents fluorescence modulation. Still, the insulin response induced by the wrappings with no side group at all, among which is the insulin sensor $C_{16}$-PEG(2000 kDa)-Ceramide, ranges between -62% to +2%.

Inspecting simple protein parameters such as their hydrophobicity (FIG. 19C) or isoelectric point (FIG. 19D) yields no correlation to the fluorescent response of the $C_{16}$-PEG (2000 kDa)-Ceramide—SWNT conjugate, and the response to insulin appears to be an outlier in these plots. As a side note, having a larger data set than the previous study, an anti-correlation of -0.67 (p<0.05) was found between the molecular weight of the PEG chain, and the response towards fibrinogen (FIG. 24).

In order to rule out the possibility that the $C_{16}$-PEG(2000 kDa)-Ceramide—SWNT simply detects the smallest protein in the library, which is insulin, the response of the insulin sensor was tested to insulin-fragments peptides of a much smaller molecular weight. Insulin is composed of two chains, a and β, linked by two disulfide bonds (FIG. 20A). See, Timofeev, V. I.; Chuprov-Netochin, R. N.; Samigina, V. R.; Bezuglov, V. V.; Miroshnikov, K. A.; Kuranova, I. P., X-ray investigation of gene-engineered human insulin crystallized from a solution containing polysialic acid. *Acta Crystallographica Section F* 2010, 66 (3), 259-263, which is incorporated by reference in its entirety. The α-chain is of 21 amino acids and the β-chain has 30 amino acids. To construct a peptide panel, the insulin chains were first divided into 9 peptides of 7 amino acids: GIVEQCC (SEQ ID NO: 11), TSICSLY (SEQ ID NO: 12), QLENYCN (SEQ ID NO: 13), FVNQHLC (SEQ ID NO: 14), GSHLVEA (SEQ ID NO: 15), LYLVCGE (SEQ ID NO: 16), RGFFYTP (SEQ ID NO: 17), FFYTPKT (SEQ ID NO: 18) (FIG. 20B). In addition, a short sequence of an insulin binding peptide was included (see Knutson, V. P., Insulin-binding peptide. Design and characterization. Journal of Biological Chemistry 1988, 263 (28), 14146-14151, which is incorporated by reference in its entirety), CVEEAS (SEQ ID NO: 10), two amino acid sequences that were showed to induce insulin fibrillation (see Chiang, H.-L.; Ngo, S. T.; Chen, C.-J.; Hu, C.-K.; Li, M. S., Oligomerization of Peptides LVEALYL (SEQ ID NO: 19) and RGFFYT (SEQ ID NO: 20) and Their Binding Affinity to Insulin. PLoS ONE 2013, 8 (6), e65358, which is incorporated by reference in its entirety), LVEALYL (SEQ ID NO: 19) and RGFFYT (SEQ ID NO: 20), and finally, 2 longer fragments of the insulin: GIVEQCCTSICSL (SEQ ID NO: 21) (α-chain 1-13), and SHLVEALYLVCGERG (SEQ ID NO: 22) (β-chain 9-23). Besides the 1-13 amino acids of the α-chain and the 9-23 amino acids of the β-chain, that induced responses of −33% and −39% decrease in the fluorescence intensity, respectively, the rest of the peptides showed negligible to no response, compared to the response of the intact insulin protein (FIG. 20C). Hence there is no correlation between the molecular weight of the analyte and the fluorescent modulation of the insulin sensor (FIG. 20D). The two outliers, insulin and apoliporprotein-AI are identified in FIG. 20D. These results also rule out the possibility that the $C_{16}$-PEG(2000 kDa)-Ceramide—SWNT recognize a particular amino acid sequence along the insulin protein, and the recognition mechanism is a more complex one in this case. Further checking the circular dichroism (CD) of the peptides testes, there is not a structure motif that appears (FIG. 25), and the signals represent mostly random coil structures. See Greenfield, N. J.; Fasman, G. D., Computed circular dichroism spectra for the evaluation of protein conformation. *Biochemistry* 1969, 8 (10), 4108-4116, which is incorporated by reference in its entirety. The insulin CD spectrum matches the one that was reported in literature. See Pocker, Y.; Biswas, S. B., Conformational dynamics of insulin in solution. Circular dichroic studies. *Biochemistry* 1980, 19 (22), 5043-5049, which is incorporated by reference in its entirety. Based on these findings, the 3-dimensional conformation of the intact native protein is crucial for the molecular recognition.

Insulin Calibration Curve.

The response of the $C_{16}$-PEG(2000 kDa)-Ceramide—SWNT to a range of insulin concentration was tested. Subsequently, the fluorescence spectra were deconvoluted to the various chiralities in the mixture, such that each chirality can be analyzed independently. The normalized fluorescent response of the (6,5), (7,5), (10,2), and (9,4) chiralities are plotted in FIG. 21A against the insulin concentration. Assuming the relative fluorescent response is linearly proportional to the relative coverage of binding sites on the nanotube surface (see Zhang, J.; Landry, M. P.; Barone, P. W.; Kim, J.-H.; Lin, S.; Ulissi, Z. W.; Lin, D.; Mu, B.; Boghossian, A. A.; Hilmer, A. J.; Rwei, A.; Hinckley, A. C.; Kruss, S.; Shandell, M. A.; Nair, N.; Blake, S.; Sen, F.; Sen, S.; Croy, R. G.; Li, D.; Yum, K.; Ahn, J.-H.; Jin, H.; Heller, D. A.; Essigmann, J. M.; Blankschtein, D.; Strano, M. S., Molecular recognition using corona phase complexes made of synthetic polymers adsorbed on carbon nanotubes. *Nature Nanotechnology* 2013, 8 (12), 959-968, Kruss, S.; Landry, M. P.; Vander Ende, E.; Lima, B. M. A.; Reuel, N. F.; Zhang, J.; Nelson, J.; Mu, B.; Hilmer, A.; Strano, M., Neurotransmitter Detection Using Corona Phase Molecular Recognition on Fluorescent Single-Walled Carbon Nanotube Sensors. *Journal of the American Chemical Society* 2013, 136 (2), 713-724, Bisker, G.; Dong, J.; Park, H. D.; Iverson, N. M.; Ahn, J.; Nelson, J. T.; Landry, M. P.; Kruss, S.; Strano, M. S., Protein-targeted corona phase molecular recognition. *Nature Communications* 2016, 7, Nelson, J. T.; Kim, S.; Reuel, N. F.; Salem, D. P.; Bisker, G.; Landry, M. P.; Kruss, S.; Barone, P. W.; Kwak, S.; Strano, M. S., Mechanism of Immobilized Protein A Binding to Immunoglobulin G on Nanosensor Array Surfaces. *Analytical Chemistry* 2015, 87 (16), 8186-8193, each of which is incorporated by reference in its entirety), the data were fitted using the Hill isotherm model:

$$\frac{I - I_0}{I_0} = -\beta\frac{\theta_{bound}}{\theta_{total}} = -\beta\frac{(K_{eq}C)^n}{1 + (K_{eq}C)^n} \quad \#2$$

where $I_0$ and $I$ are the initial and final fluorescent intensity respectively, is a proportional factor, $\theta_{total}$ and $\theta_{bound}$ are the concentration of the total and occupied binding sites respectively, $K_{eq}$ is the equilibrium constant, C is the insulin concentration, and n is the cooperativity Hill coefficient. See Foo, K. Y.; Hameed, B. H., Insights into the modeling of adsorption isotherm systems. *Chemical Engineering Journal* 2010, 156 (1), 2-10, which is incorporated by reference in its entirety.

The 3 fit-parameters and their 95% confidence intervals can be seen in FIG. 26. The equilibrium constant ranges between $10^6$-$10^7$ M$^{-1}$, the Hill coefficients are smaller than 1 for all the chirality indicating negative cooperativity, and the proportional factor ranges between 0.28 to 0.69 indicating the maximal relative fluorescent response in saturation. For comparison, calibrating the insulin sensor response against various concentrations of the insulin α-chain (1-13), and the insulin β-chain (9-23) resulted in equilibrium constant of $8.0\times10^{-4}$ M$^{-1}$ and $3.7\times10^{-4}$ M$^{-1}$ respectively, indicating weaker affinity (FIG. 27).

In order to challenge the sensor in a complex environment, the sensor response to insulin was tested in serum environment (10% Fetal bovine serum, FBS, in PBS) (FIG. 21B). Similar analysis procedure produced a good calibration for two of the chiralities (6,5) and (10,2). Here the equilibrium constants were smaller, ranging between $8\times10^{-4}$-$8.4\times10^{-4}$ M$^{-1}$, indicative of the weaker affinity in serum environment, the Hill coefficients were 0.95 and 1.4 respectively, indicating either small negative cooperativity or positive cooperativity respectively, and the proportional factor reduced to 0.26 for both chiralities as expected due to screening by other factors in the serum.

Insulin and Corona Phase Affinity.

The binding affinity between insulin and the $C_{16}$-PEG (2000 kDa)-Ceramide was tested using isothermal titration calorimetry (ITC). See Freire, E.; Mayorga, O. L.; Straume, M., Isothermal titration calorimetry. *Analytical Chemistry* 1990, 62 (18), 950A-959A, which is incorporated by reference in its entirety. The ITC instrument (MicroCal VP-ITC, Malvern) monitors the heat changes during a series of consecutive injections of 10 μl of 5 mg/ml of $C_{16}$-PEG(2000 kDa)-Ceramide in PBS, into 2.5 ml of 0.5 mg/ml insulin in PBS (FIG. 21C), or just PBS for control (FIG. 21D). According to the binding isotherms, which are calculated by integrating the heat pulses of each injection with respect to time (FIG. 21E), the heat changes of the $C_{16}$-PEG(2000 kDa)-Ceramide injections into an insulin solution almost overlaps with the heat changes of the $C_{16}$-PEG(2000 kDa)-Ceramide injections into PBS, indicating negligible to no binding between the $C_{16}$-PEG(2000 kDa)-Ceramide and insulin. See Velázquez-Campoy, A.; Ohtaka, H.; Nezami, A.; Muzammil, S.; Freire, E., Isothermal titration calorimetry. *Current Protocols in Cell Biology* 2004, 17.8. 1-17.8. 24, and Leavitt, S.; Freire, E., Direct measurement of protein binding energetics by isothermal titration calorimetry. *Current opinion in structural biology* 2001, 11 (5), 560-566, each of which is incorporated by reference in its entirety. These finding support the scheme of CoPhMoRe, i.e., only the pinned configuration of the $C_{16}$-PEG(2000 kDa)-Ceramide corona adopted when adsorbed around the nanotube scaffold can successfully detect the insulin protein.

In summary, a synthetic, non-biological, antibody analog of insulin. Using the corona phase molecular recognition (CoPhMoRe) approach, it was revealed a complex of a fluorescent single-walled carbon nanotube suspended by a PEGylated lipid amphiphilic hetero-polymer that recognizes insulin, manifested by a concentration-calibrated fluorescence intensity response. Detailed analysis shed light on the importance of the 3-dimensional confirmation of the insulin protein, which is the underlying mechanism of the recognition. There nanosensors can be implanted by encapsulation in a bio-compatible hydrogel for precise positioning, and can be excited and queried non-invasively from an external device. See Bisker, G.; Iverson, N. M.; Ahn, J.; Strano*, M. S., A Pharmacokinetic Model of a Tissue Implantable Insulin Sensor. *Advanced Healthcare Materials* 2015, 4 (1), 87-97, Iverson, N. M.; Barone, P. W.; Shandell, M.; Trudel, L. J.; Sen, S.; Sen, F.; Ivanov, V; Atolia, E.; Farias, E.; McNicholas, T. P.; Reuel, N.; Parry, N. M. A.; Wogan, G. N.; Strano, M. S., In vivo biosensing via tissue-localizable near-infrared-fluorescent single-walled carbon nanotubes. *Nat Nano* 2013, 8 (11), 873-880, Barone, P. W.; Baik, S.; Heller, D. A.; Strano, M. S., Near-infrared optical sensors based on single-walled carbon nanotubes. *Nat Mater* 2005, 4 (1), 86-U16, Kruss, S.; Hilmer, A. J.; Zhang, J.; Reuel, N. F.; Mu, B.; Strano, M. S., Carbon nanotubes as optical biomedical sensors. *Advanced Drug Delivery Reviews* 2013, 65 (15), 1933-1950, Iverson, N. M.; Bisker, G.; Farias, E.; Ivanov, V.; Ahn, J.; Wogan, G. N.; Strano, M. S., Quantitative Tissue Spectroscopy of Near Infrared Fluorescent Nanosensor Implants. *Journal of Biomedical Nanotechnology* 2016, 12 (5), 1035-1047, Giraldo, J. P.; Landry, M. P.; Faltermeier, S. M.; McNicholas, T. P.; Iverson, N. M.; Boghossian, A. A.; Reuel, N. F.; Hilmer, A. J.; Sen, F.; Brew, J. A.; Strano, M. S., Plant nanobionics approach to augment photosynthesis and biochemical sensing. *Nat Mater* 2014, 13 (4), 400-408, and Giraldo, J. P.; Landry, M. P.; Kwak, S.-Y.; Jain, R. M.; Wong, M. H.; Iverson, N. M.; Ben-Naim, M.; Strano, M. S., A Ratiometric Sensor Using Single Chirality Near-Infrared Fluorescent Carbon Nanotubes: Application to In Vivo Monitoring. *Small* 2015, 11 (32), 3973-3984, each of which is incorporated by reference in its entirety. This discovery leads the way to continuous monitoring of insulin in vivo, owing to the high stability of the synthetic recognition system, and the optical signal transduction in the near infrared part of the spectrum, which enables deep tissue detection. See, Iverson, N. M.; Bisker, G.; Farias, E.; Ivanov, V.; Ahn, J.; Wogan, G. N.; Strano, M. S., Quantitative Tissue Spectroscopy of Near Infrared Fluorescent Nanosensor Implants. *Journal of Biomedical Nanotechnology* 2016, 12 (5), 1035-1047, and Tao, Z.; Hong, G.; Shinji, C.; Chen, C.; Diao, S.; Antaris, A. L.; Zhang, B.; Zou, Y.; Dai, H., Biological imaging using nanoparticles of small organic molecules with fluorescence emission at wavelengths longer than 1000 nm. *Angewandte Chemie International Edition* 2013, 52 (49), 13002-13006, each of which is incorporated by reference in its entirety.

Materials and Methods

SWNT Suspensions.

HiPCO SWNT were initially suspended in sodium cholate (SC), by probe-tip sonication of 1 mg/ml SWNT in 2 weight % SC solution (12 W, 60 minutes) followed by ultracentrifugation (150,000 RCF, 4 hours) to remove nanotubes bundles and other impurities. See, Bisker, G.; Dong, J.; Park, H. D.; Iverson, N. M.; Ahn, J.; Nelson, J. T.; Landry, M. P.; Kruss, S.; Strano, M. S., Protein-targeted corona phase molecular recognition. *Nature Communications* 2016, 7, which is incorporated by reference in its entirety. Subsequently, a solution of 40 mg/L SC-SWNT with 2 mg/ml PEGylated-lipid was dialyzed against water for 5 days with multiple water exchanges, such that the PEGylated-lipid exchange the SC wrapping around that nanotubes.

The library of PEGylated-lipid included 18:1 PEG2000-PE, C16-PEG2000-Ceramide, 14:0 PEG5000-PE, 14:0 PEG2000-PE, C16 PEG5000-Ceramide, 16:0 PEG2000-PE, 18:0 PEG2000-PE, 18:0 PEG2000 PE-Azide, 18:0 PEG2000 PE-dibenzocyclooctyl (DBCO), 18:0 PEG2000 PE-Cyanur, 18:0 PEG2000 PE-Maleimide, 16:0 PEG5000-PE, where additional PEGylated-lipids was included in the analysis from a previous study, 25 including 18:0 PEG5000-PE, 18:0 PEG2000 PE-carboxylic acid, 18:0 PEG2000 PE-[3-(2-Pyridyldithio)-propionyl] (PDP), 18:0 PEG2000 PE-Amine, and 18:0 PEG2000 PE-Biotin, 18:0 PEG350-PE, where PE stands for phosphorylethanolamine, the number adjacent to PEG is its molecular weight in Daltons, and the preceding numbers stand for the ratio between saturated to unsaturated carbon bonds.

CoPhMoRe Screening.

A solution of 1 mg/L SWNT suspended with PEGylated-lipid was added to the wells of 96-well plate, to which the proteins analytes were added to a final concentration of 2 μg/ml in PBS. The fluorescent spectra of the various samples were acquired following 1-hour incubation using an inverted near-infrared (nIR) fluorescent microscope coupled to a nitrogen-cooled InGaAs detector through an Acton SP2500 spectrometer (Princeton Instruments). A 785 nm photodiode laser (B&W Tek Inc.) was used for fluorescent excitation.

Isothermal Titration Calorimetry.

Samples of PEGylated lipids (5 mg/ml) were injected into an isothermal titration calorimetry cell (VP-ITC MicroCalorimeter, MicroCal) containing either an insulin solution (0.5 mg/ml) or phosphate-buffered saline (PBS) for control. The temperature of the experimental cell was kept constant at 25° C., and the experiment consisted on serial injections, of 10 μl volume each, every 4 minutes into α 2.5 ml volume cell. The data were analyzed using the MicroCal Analysis software.

Circular Dichroism.

Samples were analyzed in the wavelength range of 190-260 nm (Aviv Model 202) in 1 nm intervals, using α 1 mm path length quartz cuvette (Hellma).

Other embodiments are within the scope of the following claims.

What is claimed is:

1. A composition, comprising:
a complex, wherein the complex includes:
a nanostructure that is a single-walled carbon nanotube (SWCNT); and
a polymer including a PEG derivative,
the polymer adsorbed on the nanostructure forming a corona phase and the polymer being free from selective binding to an analyte in the absence of being adsorbed on the nanostructure, wherein the polymer is a heteropolymer including a hydrophobic region and a hydrophilic region including a phospholipid and a poly(ethylene oxide); and
such that a combination of the corona phase formed by the polymer forms a selective binding site for a unique three dimensional conformation of a fibrinogen or insulin protein.

2. The composition of claim 1, wherein the nanostructure is a photoluminescent nanostructure.

3. The composition of claim 1, wherein the polymer includes a polysaccharide.

4. The composition of claim 3, wherein the polysaccharide includes dextran, a functionalized dextran, phenoxy functionalized dextran, or boronic acid functionalized phenoxy dextran.

5. The composition of claim 1, wherein the polymer includes a polynucleotide.

6. The composition of claim 5, wherein the polynucleotide has an ordered sequence, or is poly(AT), poly(GU), poly(GT), poly(CT), poly(AG), poly(GC), poly(AC), poly(AAAT), poly(ATTT), poly(GGGT), or poly(GTTT).

7. The composition of claim 1, wherein the polymer includes a polypeptide.

8. The composition of claim 7, wherein the polypeptide includes a mastoparan, mastoparan 7, or mastoparan X.

9. The composition of claim 1, wherein the polymer includes a polylipid.

10. The composition of claim 9, wherein the polylipid includes a phospholipid, a palmitoyl phospholipid, 1,2-dipalmitoyl-sn-glycero-3-phosphoethanolamine-N-(lauroyl), dipalmitoyl-phosphatidylethanolamine, dimyristoyl-phosphatidylethanolamine or distearoyl-phosphatidylethanolamine.

11. The composition of claim 1, wherein the polymer includes polyvinylpyrrolidone, poly(ethylene oxide)-poly (propylene oxide)-poly(ethylene oxide) block co-polymer, a poly(ethylene oxide), poly(N-isopropyl acrylamide), polyethyleneimine, polyacrylamide, polyvinyl alcohol or collagen.

12. The composition of claim 1, wherein the polymer includes a dye conjugate or a branched polymer.

13. The composition of claim 1, wherein the phospholipid is dipalmitoyl-phosphatidylethanolamine, dimyristoyl-phosphatidylethanolamine or distearoyl-phosphatidylethanolamine.

14. The composition of claim 1, wherein the heteropolymer is ceramide-$C_{16}$-PEG(2000 kDa).

15. The composition of claim 1, wherein the complex includes a selective binding site for an analyte that is fibrinogen.

16. The composition of claim 1, wherein the heteropolymer is dipalmitoyl-phosphatidylethanolamine (DPPE)-PEG (5000).

17. The composition of claim 1, wherein the complex includes a selective binding site for an analyte that is insulin.

18. A system comprising:
   the composition of claim 1;
   an electromagnetic radiation source having an excitation wavelength directed at the composition; and
   a detector configured to receive an emission wavelength from the composition.

* * * * *